United States Patent
Bordenstein et al.

(10) Patent No.: US 11,268,100 B2
(45) Date of Patent: Mar. 8, 2022

(54) PHAGE-MEDIATED MANIPULATION OF WOLBACHIA

(71) Applicant: VANDERBILT UNIVERSITY, Nashville, TN (US)

(72) Inventors: Sarah R. Bordenstein, Nashville, TN (US); Seth R. Bordenstein, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 451 days.

(21) Appl. No.: 16/093,808

(22) PCT Filed: Apr. 14, 2017

(86) PCT No.: PCT/US2017/027678
§ 371 (c)(1),
(2) Date: Oct. 15, 2018

(87) PCT Pub. No.: WO2017/181043
PCT Pub. Date: Oct. 19, 2017

(65) Prior Publication Data
US 2019/0136244 A1 May 9, 2019

Related U.S. Application Data

(60) Provisional application No. 62/323,099, filed on Apr. 15, 2016.

(51) Int. Cl.
*C12N 15/74* (2006.01)
*C12N 15/86* (2006.01)

(52) U.S. Cl.
CPC ............. *C12N 15/74* (2013.01); *C12N 15/86* (2013.01); *C12N 2795/10022* (2013.01); *C12N 2795/10043* (2013.01); *C12N 2800/30* (2013.01); *C12N 2800/40* (2013.01)

(58) Field of Classification Search
None
See application file for complete search history.

(56) References Cited

U.S. PATENT DOCUMENTS

2005/0054106 A1 3/2005 Ow et al.

FOREIGN PATENT DOCUMENTS

WO 2004/018635 3/2004

OTHER PUBLICATIONS

Kent, B.N., et al. 2011 PLoS ONE 6(9): e24984; pp. 1-6. (Year: 2011).*
Julien, B. "Characterization of the Integrase Gene and Attachment Site for the Myxococcus xanthus Bacteriophage Mx9", Journal of Bacteriology, Nov. 2003, pp. 6325-6330.
Extended EP Search Report dated Oct. 11, 2019, from related EP application No. 17783259.9, 10 pages.
Wang et al. "Multiple Horizontal Transfers of Bacteriophage WO and Host *Wolbachia* in Fig Wasps in a Closed Community", Frontiers in Microbiology, Feb. 2016, vol. 7, Article 136, pp. 1-10.
Tanaka et al. "Complete WO Phage Sequences Reveal Their Dynamic Evolutionary Trajectories and Putative Functional Elements Required for Integration into the *Wolbachia* Genome", Applied and Environmental Microbiology, Sep. 2009, vol. 75, No. 17, pp. 5676-5686.
Fish et al. "Creating transgenic *Drosphila* by microinjecting the site-specific oC31 integrase mRNA and a transgene-containing donor plasmid", Nature Protocols, vol. 2, No. 10, 2007, pp. 2235-2331.
Fujii et al. "Isolation and characterization of the bacteriophage WO from *Wolbachia*, an arthropod endosymbiont", Biochemical and Biophysical Research Communications, 317 (2004) 1183-1188.
Slatko et al. "Wolbachia endosymbionts and human disease control", Molecular & Biochemical Prasitology 195 (2014) 88-95.
Baldridge et al. "The Wolbachia WO bacteriophage proteome in the Aedes albopictus C/wStrl cell line: evidence for lytic activity?", In Vitro Cell. Dev. Biol.—Animal (2016) 52:77-88.
Champer et al. "Cheating evolution: engineering gene drives to manipulate the fate of wild populations", Nature Reviews, Genetics, 2016, 14 pages.
International Search Report and Written Opinion dated Sep. 8, 2017, from International Application No. PCT/US17/27678, 14 pages.
Kent, B.N. et al. "Phage WO of Wolbachia: lambda of the endosymbiont world", Trends in Microbiology, vol. 18, No. 4, Apr. 1, 2010, pp. 173-181.
Communication pursuant to Article 94(3) EPC dated Jun. 19, 2020, from related EP application No. 17783259.9, 4 pages.
Communication pursuant to Article 94(3) EPC dated Feb. 3, 2021, from related EP application No. 17783259.9, 5 pages.

* cited by examiner

*Primary Examiner* — Marsha Tsay
(74) *Attorney, Agent, or Firm* — Meunier Carlin & Curfman LLC

(57) ABSTRACT

The invention relates to systems, methods, and compositions for the genetic modification of *Wolbachia*.

Figures 1A, 1B, 1C, 1D:
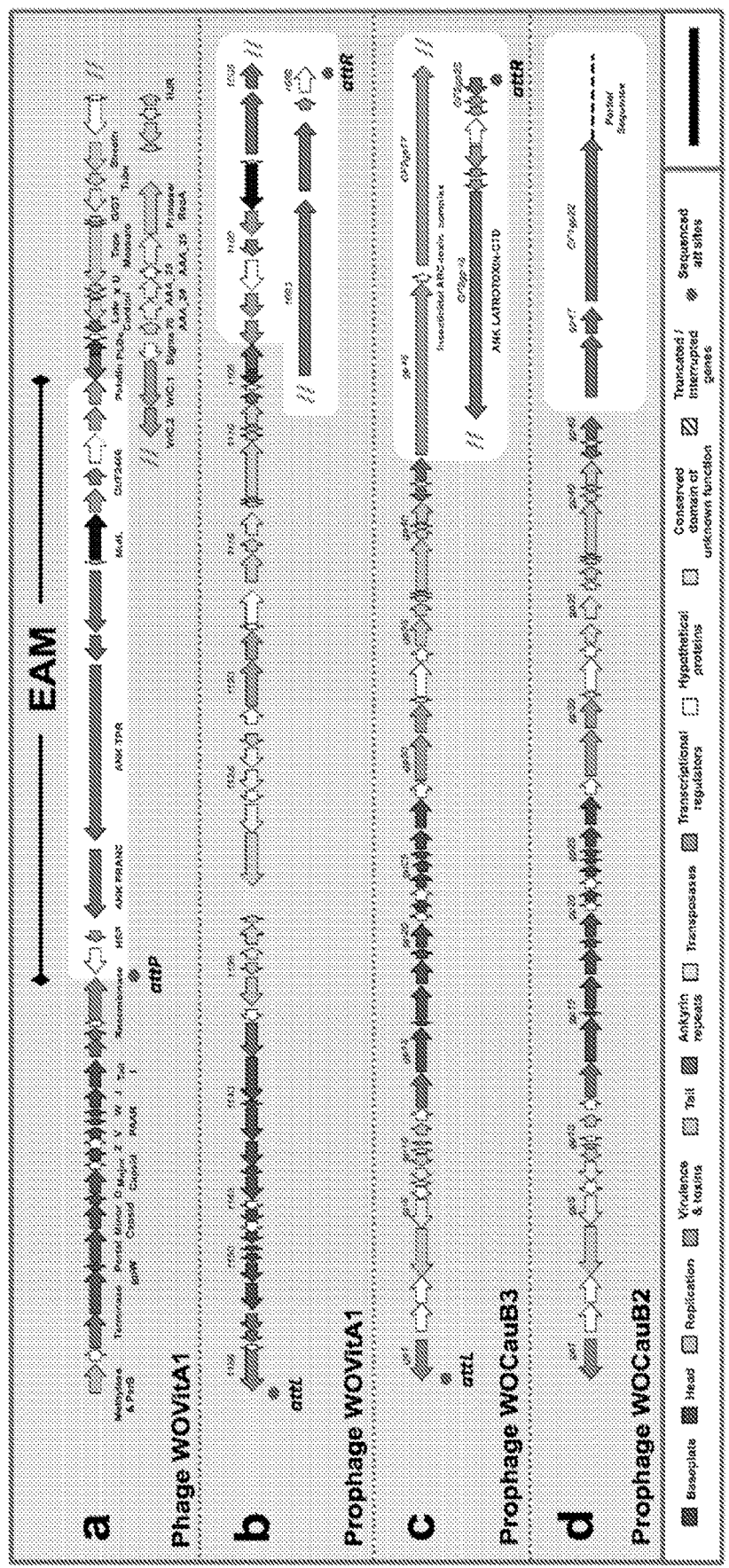

18 Claims, 23 Drawing Sheets
Specification includes a Sequence Listing.

FIGS. 3A

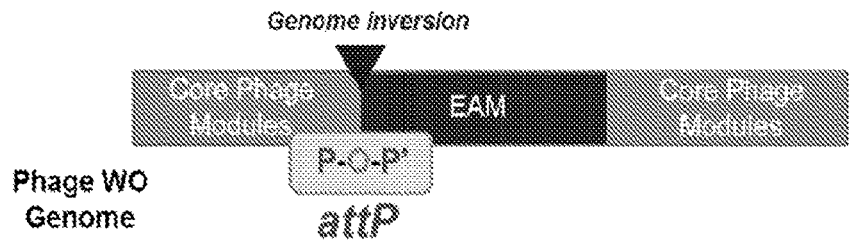
FIG. 7A
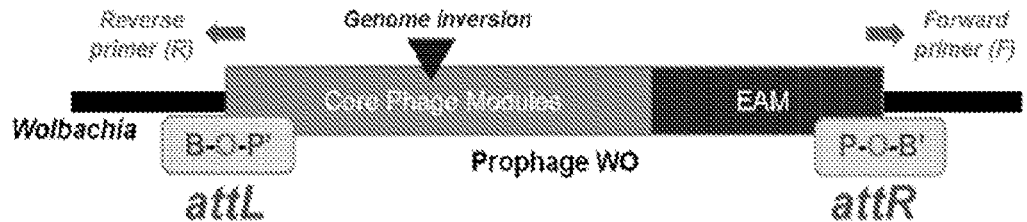
FIG. 7B
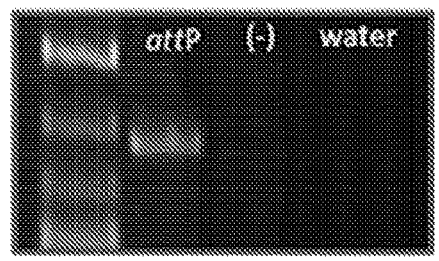
FIG. 7C
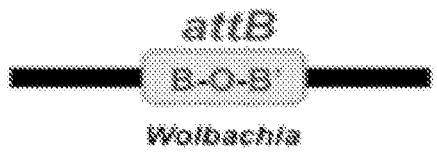
FIG. 7D
attL - B  GCAAATACAATAGCTTCACTGTT ATGACGTCCAGTACAATGTTGCAA  P'
attR  P  TTTTTGTAACATTGTTATACACATC ATGA TAAGGGGGCTGGCGGAGTTT  B
attP - P  TTTTTGTAACATTGTTATACACATC ATGACGTCCAGTACAATGTTGCAA  P'
attB* - B  GCAAATACAATAGCTTCACTGTT ATGA TAAGGGGGCTGGCGGAGTTT  B
FIG. 7E

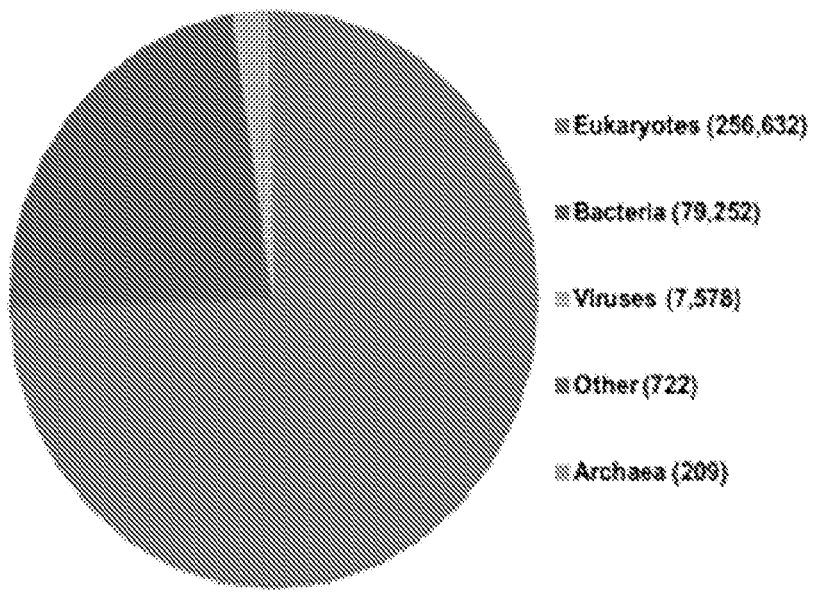
FIG. 8A
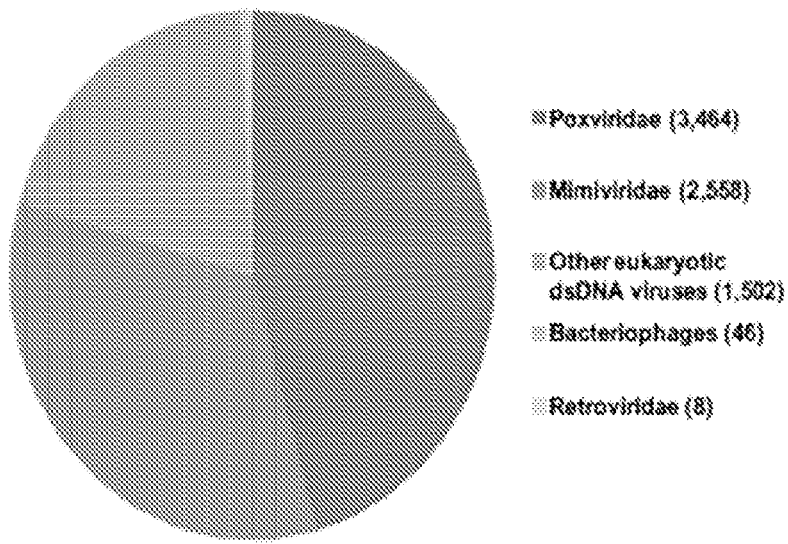
FIG. 8B
| Bacteriophages | # Ankyrin-containing protein records in NCBI | Length (# aa residues) |
|---|---|---|
| Phage WO | 29 | 148-2474 |
| *Campylobacter* phage | 4 (identical) | 95 |
| *Gordonia* phage | 2 (identical) | 102 |
| *Lactococcal* phage | 3 (identical) | 169 |
| *Leptospira* phage | 2 (identical) | 260 |
| *Salmonella* phage | 3 | 69-103 |
| Uncultured Mediterranean phage uvMED | 3 | 173-191 |
FIG. 8C

FIG. 21

PHAGE-MEDIATED MANIPULATION OF WOLBACHIA

CROSS REFERENCE TO RELATED APPLICATIONS

This application is a national stage application filed under 35 U.S.C. § 371 of PCT/US2017/027678 filed Apr. 14, 2017, which claims the benefit of U.S. Provisional Patent Application Ser. No. 62/323,099 filed Apr. 15, 2016, the disclosures of which are is expressly incorporated herein by reference.

STATEMENT REGARDING FEDERALLY SPONSORED RESEARCH

This invention was made with Government Support under Grant No. R01GM085163 awarded by the National Institutes of Health. The Government has certain rights to the invention.

FIELD

The invention relates to systems, methods, and compositions for the genetic modification of *Wolbachia*.

REFERENCE TO SEQUENCE LISTING

The Sequence Listing submitted Mar. 2, 2021 as a text file named "10644-023US1_2021_03_02_Revised_Sequence_Listing.txt," created on Dec. 20, 2018, and having a size of 9,000 bytes is hereby incorporated by reference pursuant to 37 C.F.R. § 1.52(e)(5).

BACKGROUND

*Wolbachia pipientis* is an obligate, intracellular α-proteobacteria and a member of the Rickettsiales family. These gram-negative bacteria are not culturable outside of host cells and, as a result, knowledge on *Wolbachia* symbiosis has only surged in the last two decades owing to readily available molecular techniques. Once considered an obscure bacterium in a few insect species, the most recent meta-analysis estimates that ~40% of all arthropod species are infected with *Wolbachia* as well as 47% of the Onchocercidae family of filarial nematodes.

One of the greatest limitations in *Wolbachia* research is the inability to successfully transform these bacteria. Until the *Wolbachia* genome can be manipulated, it is unlikely that fundamental questions regarding the mechanism or applications of cytoplasmic instability (CI) and other aspects of *Wolbachia* biology will be definitively addressed. Thus, there is an unmet need for compositions and methods for genetically modifying *Wolbachia*.

The systems, methods, and compositions disclosed herein address these and other needs.

SUMMARY

Disclosed herein are systems, methods, and compositions for the genetic modification of *Wolbachia*. Previously, there has been no way to stably transform *Wolbachia* bacteria and thus no method for genetically modifying *Wolbachia*. The inventors have identified the phage attachment sequences and serine recombinase in the WO phage from *Wolbachia* that can be used for the genetic modification of *Wolbachia*. These compositions and methods allow the introduction of heterologous genes into the *Wolbachia* genome.

In one aspect of the invention, provided herein is a WO phage transformation system that can be used to stably transform *Wolbachia*. In one aspect of the invention, disclosed herein is a WO phage transformation system, said system comprising:
a) a first DNA vector comprising a gene encoding a protein with WO phage integrase activity operably linked to a first promoter active in a host cell, and
b) a second DNA vector comprising an attachment site (attP) recognized by the WO phage integrase protein.

In one embodiment, the second DNA vector further comprises a heterologous gene.

In one aspect of the invention, disclosed herein is a WO phage transformation system, said system comprising:
a) a protein with WO phage integrase activity, and
b) a DNA vector comprising an attachment site (attP) recognized by the WO phage integrase protein.

In one aspect of the invention, disclosed herein is a WO phage vector, said vector comprising:
a) a gene encoding a protein with WO phage integrase activity operably linked to a first promoter active in a host cell;
b) a second attachment site (attP) recognized by the WO phage integrase protein, and
c) a heterologous gene.

In another aspect, disclosed herein is a genetically modified *Wolbachia* cell, wherein said *Wolbachia* cell is a symbiont of an insect, wherein the *Wolbachia* cell is transformed to express a heterologous gene, wherein the expression of the heterologous gene either decreases the ability of the insect to transmit a pathogen or reduces the reproductive potential of the insect population.

In a further aspect of the invention, disclosed herein is a method for the genetic modification of DNA of a *Wolbachia* cell comprising in its genome a first attachment site (attB) recognized by a protein with WO phage integrase activity, comprising introducing a WO phage transformation system into the cell, said system comprising:
a) a first DNA vector comprising a gene encoding a protein with WO phage integrase activity operably linked to a first promoter active in the *Wolbachia* cell, and
b) a second DNA vector comprising a second attachment site (attP) recognized by the integrase protein.

In a further aspect of the invention, disclosed herein is a method for the genetic modification of a DNA of a *Wolbachia* cell comprising in its genome a first attachment site (attB) recognized by a protein with WO phage integrase activity, comprising introducing a WO phage transformation system into the cell, said system comprising:
a) a protein with WO phage integrase activity, and
b) a DNA vector comprising a second attachment site (attP) recognized by the WO phage integrase protein.

In one aspect, disclosed herein is a method for the genetic modification of a DNA of a *Wolbachia* cell comprising in its genome a first attachment site (attB) recognized by a protein with WO phage integrase activity, comprising introducing a WO phage vector, said vector comprising:
a) a gene encoding a protein with WO phage integrase activity operably linked to a first promoter active in a host cell;
b) a second attachment site (attP) recognized by the WO phage integrase protein, and
c) a heterologous gene.

In another aspect, provided herein is a method for treating a filarial nematode infection in a host, comprising the steps: administering a WO phage vector to the host, said vector comprising:

a) a gene encoding a protein with WO phage integrase activity operably linked to a first promoter active in the host cell, and b) an attachment site (attP) recognized by the WO phage integrase protein;

wherein delivery of the WO phage vector into a *Wolbachia* cell causes lysis or inhibits the growth of the *Wolbachia* cell.

BRIEF SUMMARY OF THE DRAWINGS

The accompanying figures, which are incorporated in and constitute a part of this specification, illustrate several aspects described below.

FIGS. 1A-ID. The complete phage WO genome for (a) WOVitA1 was sequenced directly from purified viral particles using high throughput, metagenomic sequencing. The prophage (b) WOVitA1, (c) WOCauB3 and (d) WOCauB2 genomes were reannotated based on sequencing reads obtained from purified phage WO particles; complete genomes of WOCauB3 and WOCauB2 were not obtained. Each genome consists of a bacteriophage-like region (recombinase to patatin) and EAM highlighted in white. Grey slash marks indicate illustrative continuation of the genome. Dark dots indicate the discovery of the attL and attR sites of the prophage, which adjoin in the packaged WO genome to form attP. Numbers above the open reading frames indicate locus tags. Scale bar, 5,000 base pairs.

FIGS. 2A-2B. Eukaryotic-like EAM genes are enriched in prophage WO regions in the *Wolbachia* chromosome. EAM genes with (a) eukaryotic homology are most likely to be associated with prophage WO while those with (b) bacterial homology are both phage-associated and found scattered throughout the *Wolbachia* chromosome. (*) The two chromosomal latrotoxin-CTD domains (wNo_10650 and wHa_05390) are located within phage-associated genes and transposases, indicating a potential genomic rearrangement. (†) SecA represents one "domain type" but is listed separately because phage WO contains two different homologs (i.e., wHa_3920 and wHa_3930). Putative functional categories are: anti-eukaryotic toxins (Latrotoxin-CTD, ABC toxin); host-microbe interactions (PRANC, Ulp1, OTU); host cell suicide (NACHT, NB-ARC); secretion of virulence factors (SecA1, SecA2); and unknown (gwv_1093, Octomom-NTD). Octomom refers to WD0513 of the wMel genome.

FIGS. 3A-3D. Latrotoxin-CTD phylogeny and protein architecture reveal lateral genetic transfers between black widow spiders and bacteriophage WO. (a) Phylogeny of phage WO latrotoxin-CTD protein domains and their eukaryotic homologs was constructed by Bayesian analysis of 74 amino acids using the JTT model of evolution. Consensus support values are shown at the nodes. Comparative protein architecture shows that spider venom (b) vertebrate-specific alpha-latrotoxins and (c) invertebrate-specific alpha- and delta-latrotoxins are highly conserved, whereas (d) phage WO are not. Bolded nomenclature in (d) denotes the specific phage WO haplotype (listed as WO). Genome locus tags are listed in parentheses. Predicted furin cleavage sites, listed in Table 2, are illustrated with gray triangles. (*) A second *L. hesperus* sequence represents a recently-described downstream paralog with unknown toxin activity[81]. (†) wNo_10650 is located within phage-associated genes and transposases, indicating a potential genomic rearrangement of a phage region. (‡) Architecture is not shown for sequences on incomplete contigs (WOBol1-b, WOAlbB, WOCit, WOPipMol, WOVitB) because complete peptide information and specific phage association are unknown.

FIGS. 4A-4C. A conserved TPR and ankyrin-repeat protein horizontally transferred from eukaryotes to bacteriophage WO. (a) An 800-aa BLASTp query of WOVitA1's gwv_1093 N-terminus reveals homologs throughout mosquitoes, ants, beetles, a mealybug and one obligate intracellular gammaproteobacteria. Bayesian phylogenetic trees were constructed based on (b) a 137-aa alignment of all homologs with E-value less than $e^{-40}$ using the LG+G model of evolution. (c) To resolve taxa closest to phage WO, trees were reconstructed based on a 627-aa alignment of all homologs with an E-value of 0 using the JTT+I+G model of evolution. Isoforms were removed from each alignment. Both trees are unrooted. Consensus support values are shown at the nodes. Chromosomal neighborhood analyses of available animal genome sequences indicate that animal homologs to the phage WO protein are on contigs with other animal genes.

FIGS. 5A-5C. The programmed cell death domain, NACHT, horizontally transferred from eukaryotes to bacteriophage WO. (a) A 450-aa BLASTp query of phage WO's NACHT region reveals homologs throughout arthropods and crustaceans. (b) Bayesian phylogenetic trees were constructed based on a 271-aa alignment of all homologs with E-value less than $e^{-15}$ and coverage greater than 70% using the cpREV+G model of evolution. To resolve taxa closest to phage WO, all *Daphnia* sequences were removed from the alignment and clusters of highly divergent residues (i.e., 5 or more sequential residues with less than 15% pairwise identity) were trimmed. Trees were reconstructed based on this 262-aa alignment using the LG+G model of evolution. Consensus support values are shown at the nodes. Both trees are unrooted. Chromosomal neighborhood analyses of available animal genome sequences indicate that animal homologs to the phage WO protein are on contigs with other animal genes. (c) Schematic and alignment of domains from proteins containing the programmed cell death domain, NACHT.

FIGS. 6A-6D. DNA transfer between eukaryotes and bacteriophages. (a) The eukaryotic cell can harbor multiple microbes capable of horizontal gene transfer. Genetic transfers between eukaryotes and bacteriophages can, in theory, occur (b) directly between eukaryotic chromosomes and phage genomes; (c) indirectly between eukaryotic and *Wolbachia* chromosomes; or (d) indirectly between eukaryotic chromosomes and intermediary entities, such as eukaryotic viruses and other intracellular bacteria.

FIGS. 7A-7E. Sequencing reveals the phage, prophage and bacterial att sites for WOVitA1. (a) The entire prophage WO genome, including all core phage modules and the EAM, is integrated into the *Wolbachia* chromosome. Attachment sites are designated as BOP' (attL) and POB' (attR) with B representing 'bacterial' and P representing 'phage'-associated nucleotides. Gray arrows indicate the direction of PCR primers used to amplify the (b) phage attachment (attP) site, designated as POP' in the (c) circular WOVitA1 genome. (d) The bacterial attachment site (attB) is designated as BOB' on the *Wolbachia* chromosome. (e) All four att sites share a common region, O. Underlined nucleotides represent an inverted repeat region. *The attB site was predicted based on the attL and attR sequences. A BLASTN search of this sequence identified the putative attB site as a non-coding, repetitive sequence in closely related *Wolba-*

*chia* taxa lacking the WOVitA1 infection (e.g., wAu, wMel, and wRi). Sequences referred to in FIG. 7 include: SEQ ID NO:3, attL, GCAAATACAATAGCTTCACTGT-TATGACGTCCAGTACAATGTTGCAA; SEQ ID NO:4, attR, TTTTTGTAACATTGTTATACACATCATGA-TAAGGGGGCTGGCGGAGTTT; SEQ ID NO:5, attP, TTTTTGTAACATTGTTATACACAT-CATGACGTCCAGTACAATGTTGCAA; SEQ ID NO:6, attB, GCAAATACAATAGCTTCACTGTTATGA-TAAGGGGGCTGGCGGAGTTT.

FIGS. 8A-8C. Ankyrin repeat domain distribution. (a) Ankyrin repeat domain distribution across eukaryotes, bacteria, viruses, archaea, and other groups. (b) Ankyrin repeat domain distribution across viral groups. (c) Ankyrin repeat domain distribution in bacteriophages.

Figure 9A:
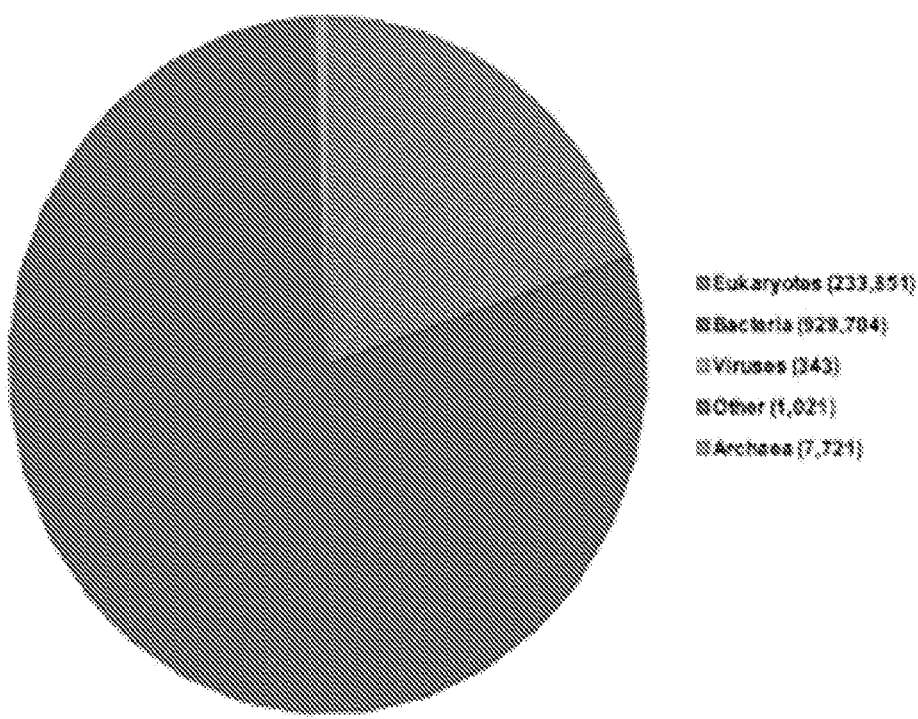
Figure 9B:
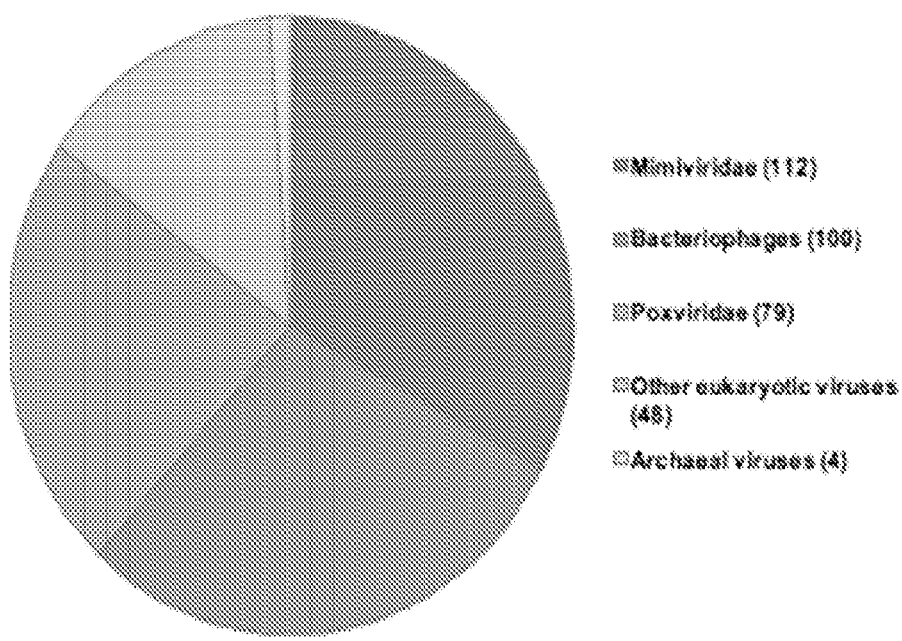

FIGS. 9A-9B. Tetratricopeptide repeat (TPR) domain distribution. (a) TPR repeat domain distribution across eukaryotes, bacteria, viruses, archaea, and other groups. (b) TPR repeat domain distribution across viral groups.

Figure 10A:
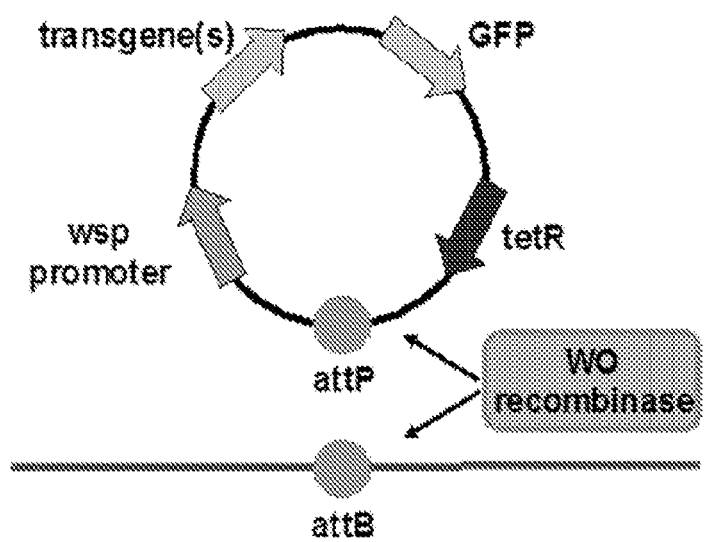
Figure 10B:
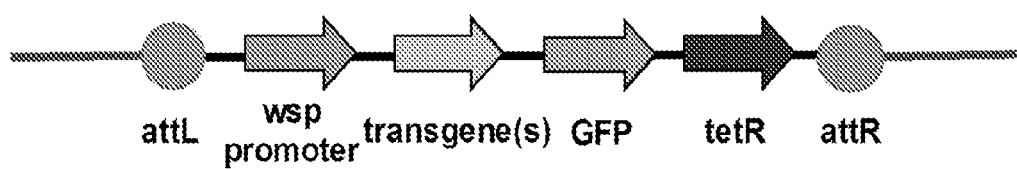
Figure 11:
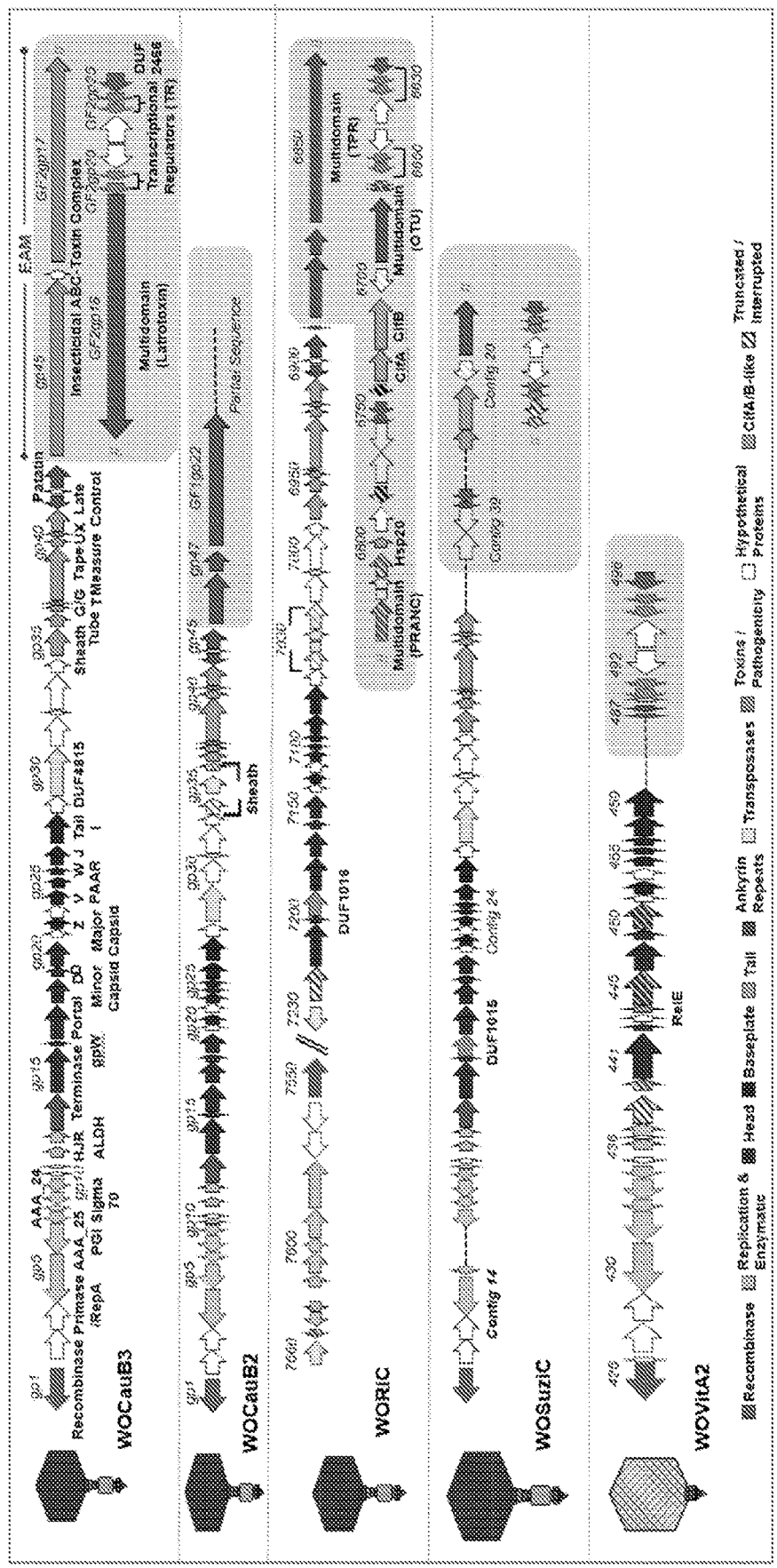

FIGS. 10A-10B. An overview of phage WO-mediated transformation. (a) The phage WO serine recombinase mediates recombination between the phage (attP) and bacterial (attB) attachment sites. (b) All genes on the attP-containing plasmid are unidirectionally incorporated into the bacterial chromosome. wsp—*Wolbachia* surface protein; GFP—green fluorescent protein; tetR—tetracycline resistance FIG. 11. Family 1 prophage genomes are categorized based on nucleotide sequence homology of their recombinase genes and the following module organization: recombinase, replication and enzymatic, head, baseplate, tail, patatin, and eukaryotic association module (EAM). WORiC and WOSuziC contain cifA and cifB genes for Type II cytoplasmic incompatibility factors. Images to the left of the prophage WO genomes are genome-enabled predictions of the physical structure of the phage WO particles.

Figure 12:
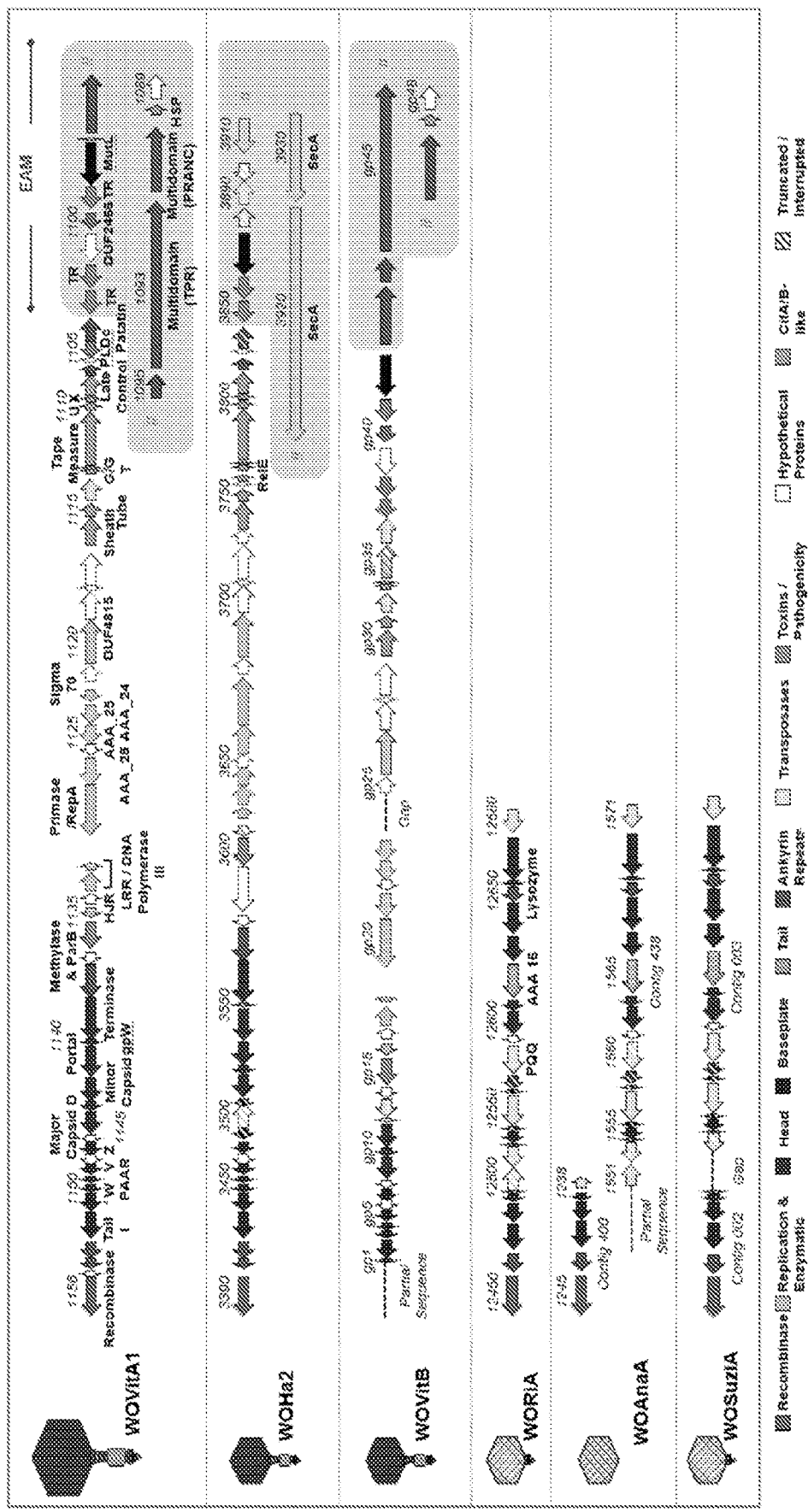

FIG. 12. Family 2 prophage genomes are categorized based on nucleotide sequence homology of their recombinase genes and the following module organization: recombinase, baseplate, head, replication and enzymatic, tail, patatin, and EAM. WORiA, WOAnaA, and WOSuziA contain a fully intact recombinase and head module, but lack most other modules. These haplotypes also encode a lysozyme and AAA16. Images to the left of the prophage WO genomes are genome-enabled predictions of the physical structure of the phage WO particles.

Figure 13:
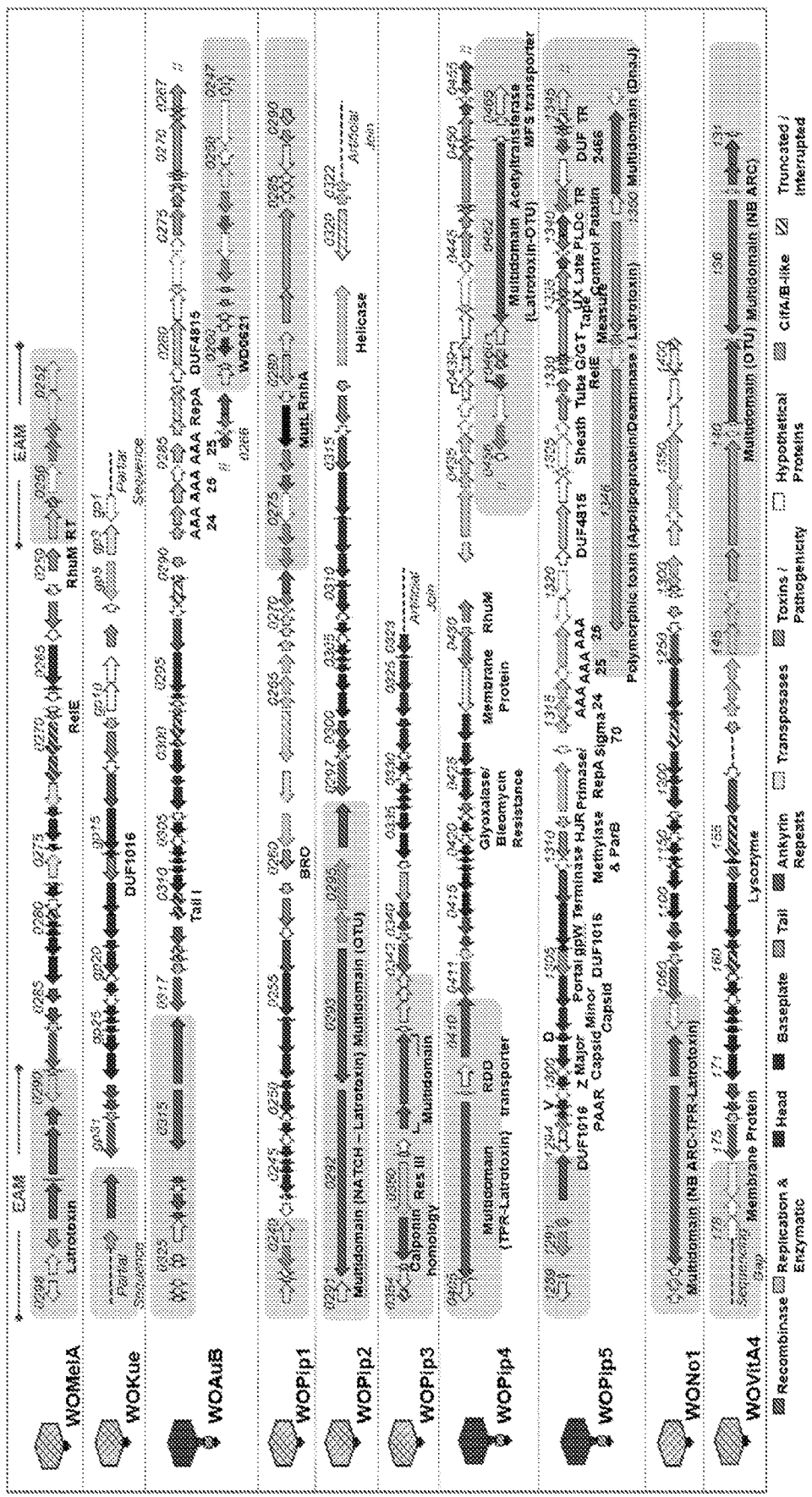

FIG. 13. Family 3 prophage genomes are highly variable. They are categorized based on sequence homology of their recombinase genes and the presence of both 5' and 3' flanking transposases. They generally contain a baseplate, head, and EAM with only a few genomes encoding a complete tail. Prophages in this family often contain Type I cifA/cifB. Images to the left of the prophage WO genomes are genome-enabled predictions of the the structure of the phage WO particles.

Figure 14:
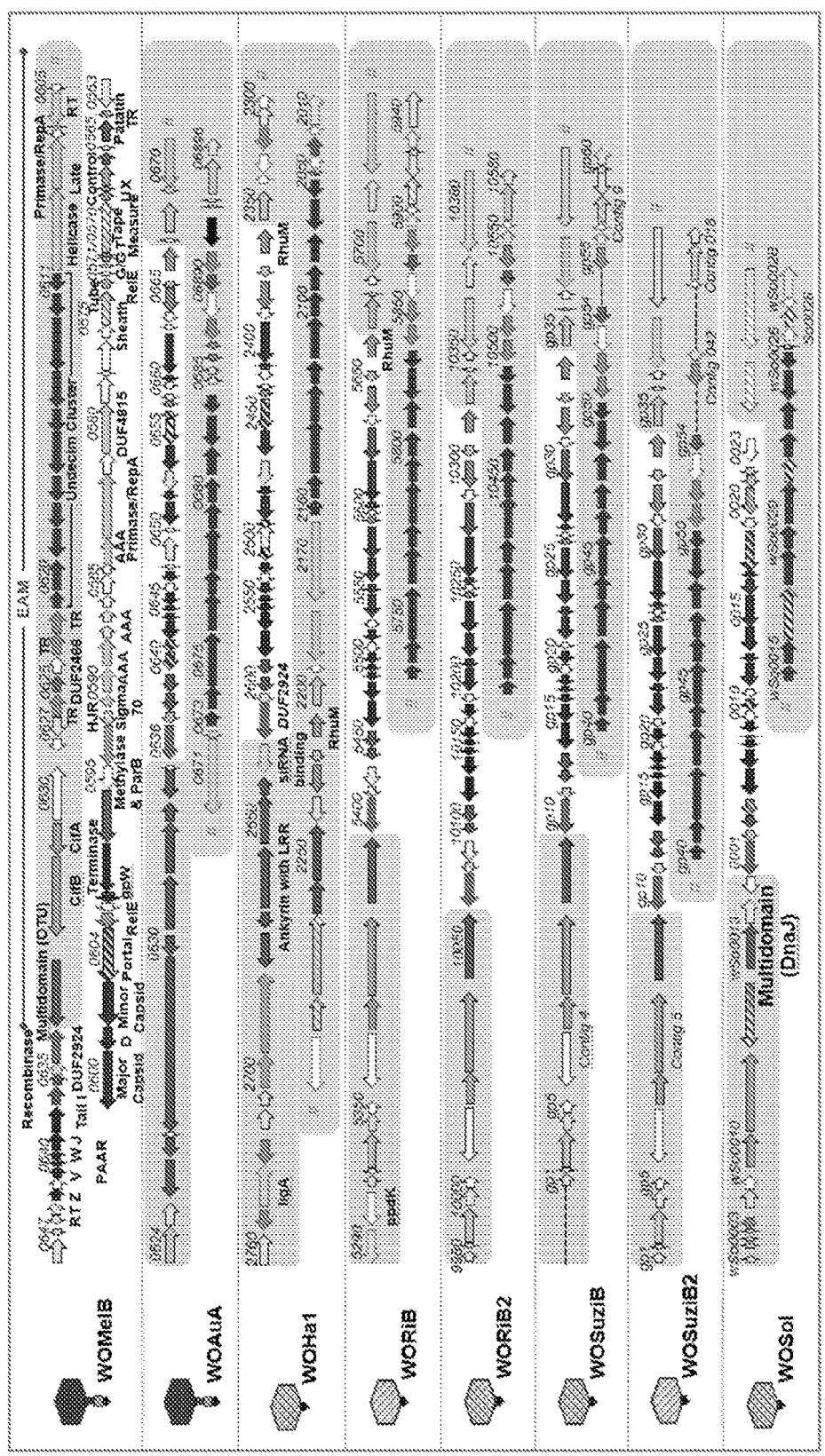

FIG. 14. A subset of Family 3 prophages is further categorized by the presence of a highly conserved WD0611-WD0621 like region. All of these genomes, except WOAuA, contain Type I cifA/cifB. Images to the left of the prophage WO genomes are genome-enabled predictions of the the structure of the phage WO particles.

Figure 15:
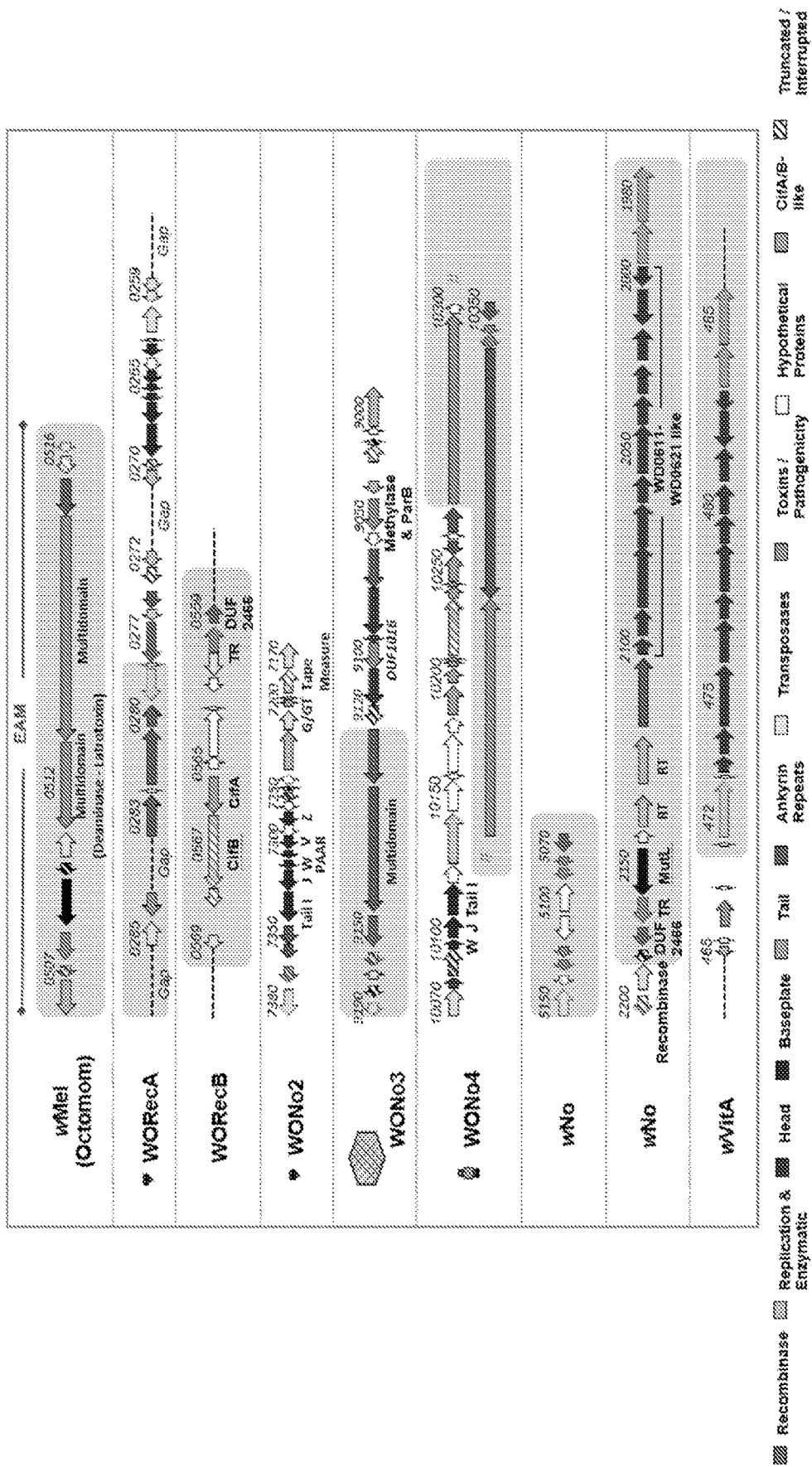

FIG. 15. Clusters of prophage-related genes can be found throughout the *Wolbachia* genome and are referred to as "WO-like Islands." These regions contain only one structural module and/or group of WO-related genes. Some WO-like Islands, such as wNo and wVitA, contain Type III cifA/cifB. Images to the left of the WO-like Islands are genome-enabled predictions of the structure for each region.

Figure 16:
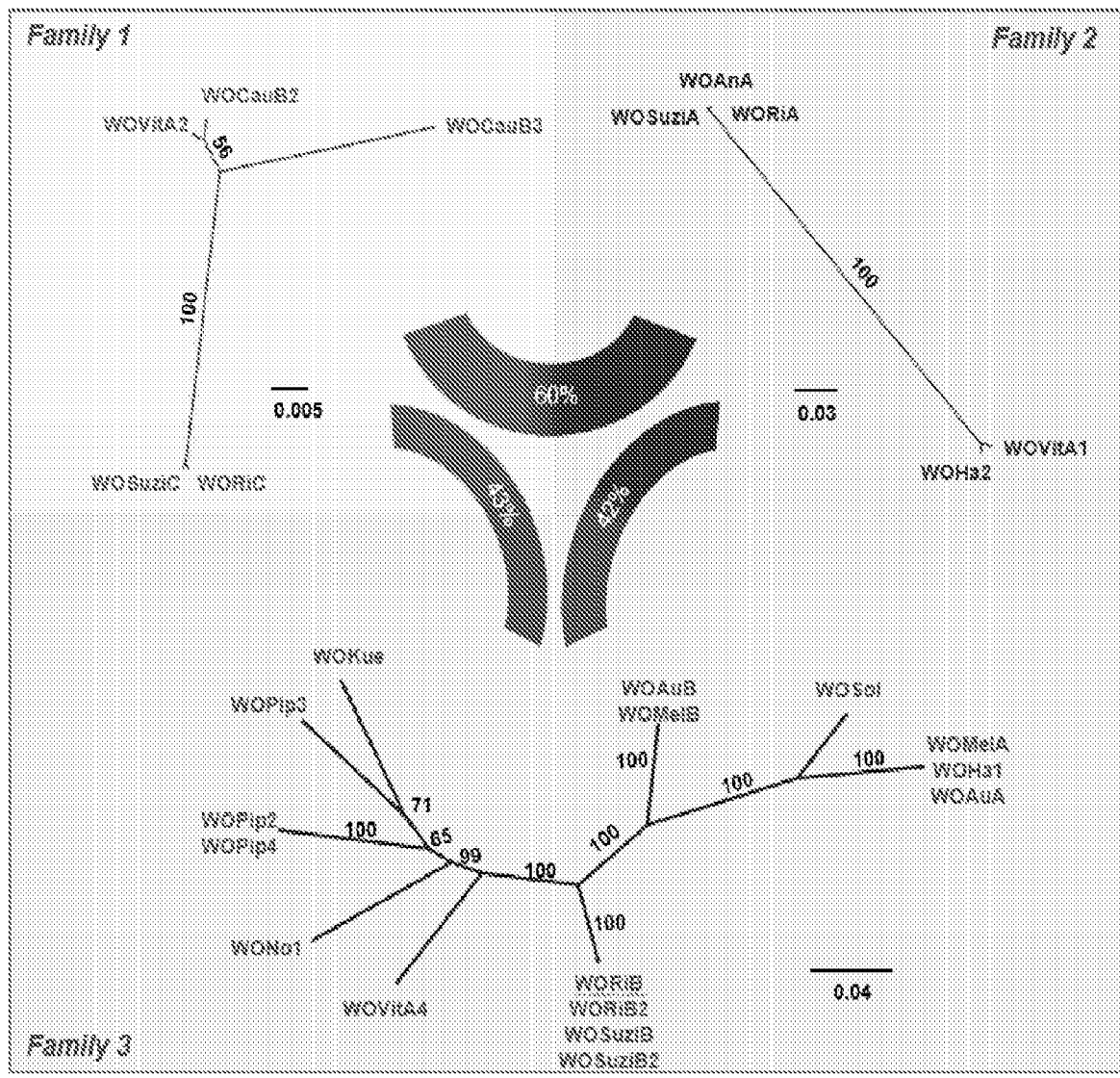

FIG. 16. Each phage WO Family is associated with a unique recombinase sequence. Within each Family, the evolutionary phylogeny of the recombinase sequence correlates with overall sequence homology of the prophage region. Family 1 and Family 2 recombinases are more closely related to each other (60% nucleotide identity) than to Family 3 (43% and 42%, respectively). The percent nucleotide identity is based on an alignment of all recombinase sequences within each of the two representative families.

Figure 17:
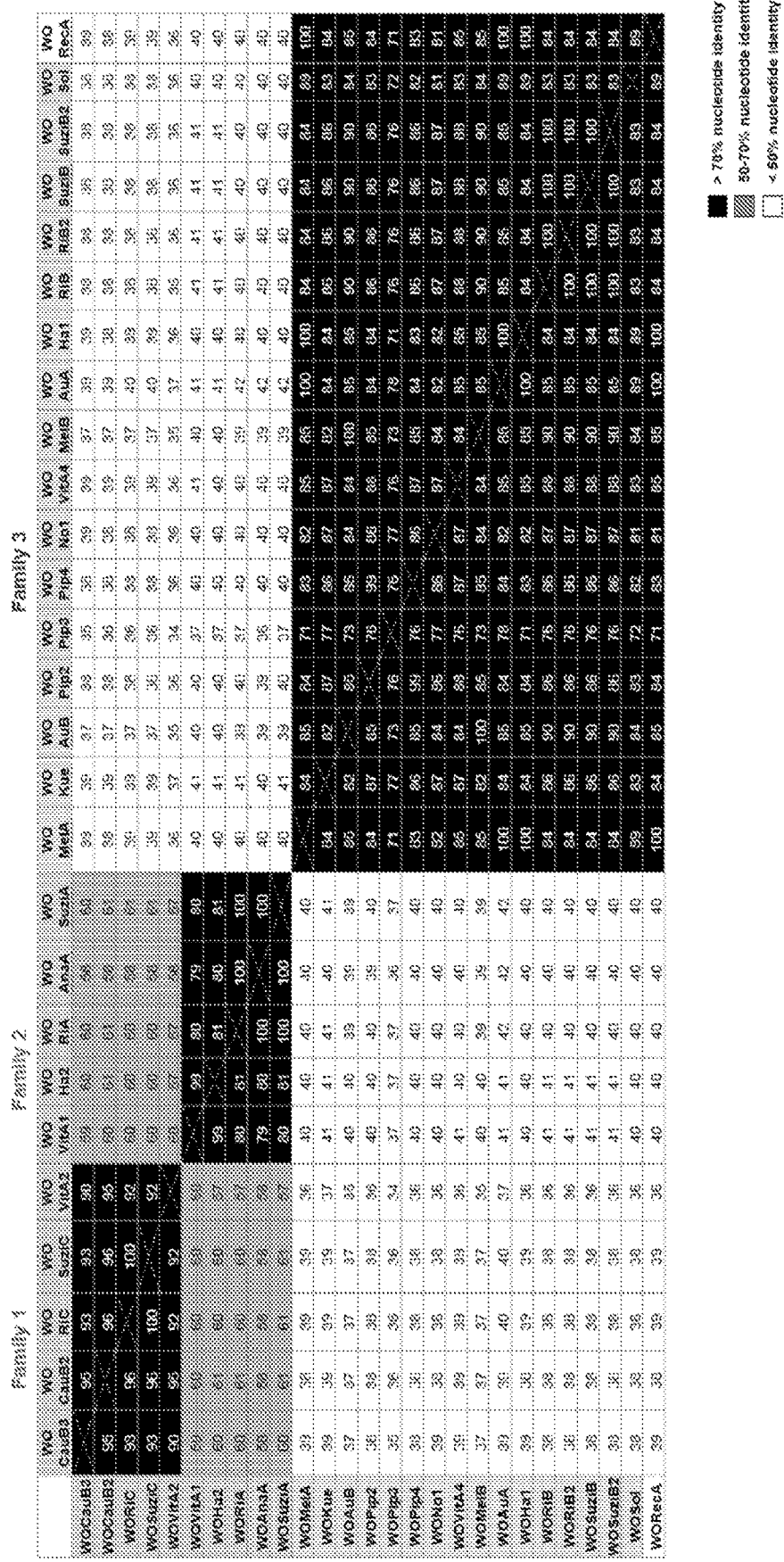

FIG. 17. Prophages within the same Family contain similar (>70% nucleotide identity) recombinase sequences. This table shows the % nucleotide identity of recombinase sequences based on a global alignment.

Figure 18:
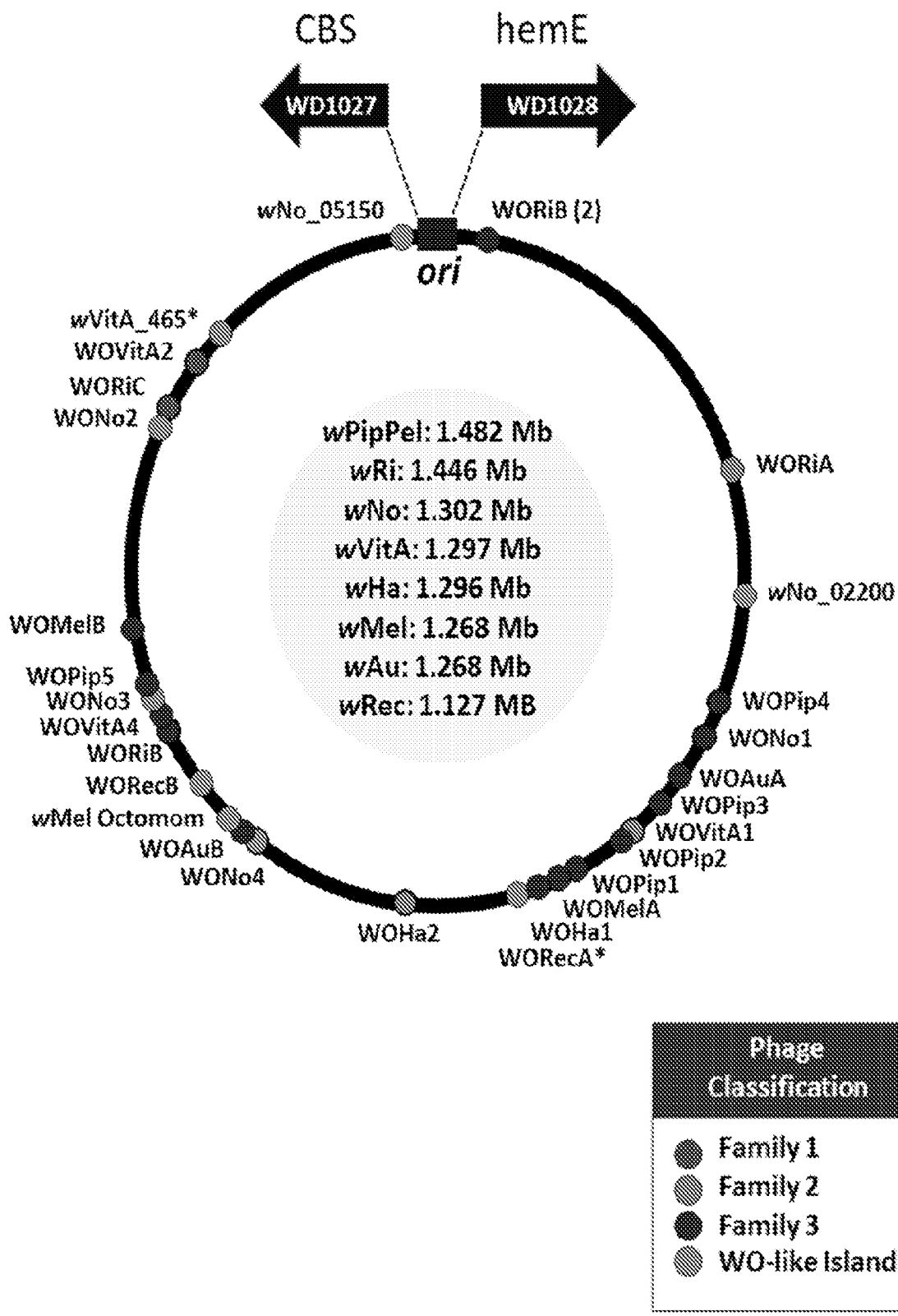

FIG. 18. The majority of phage WO haplotypes integrate opposite the origin of replication (ori) in the *Wolbachia* chromosome.

Figure 19:
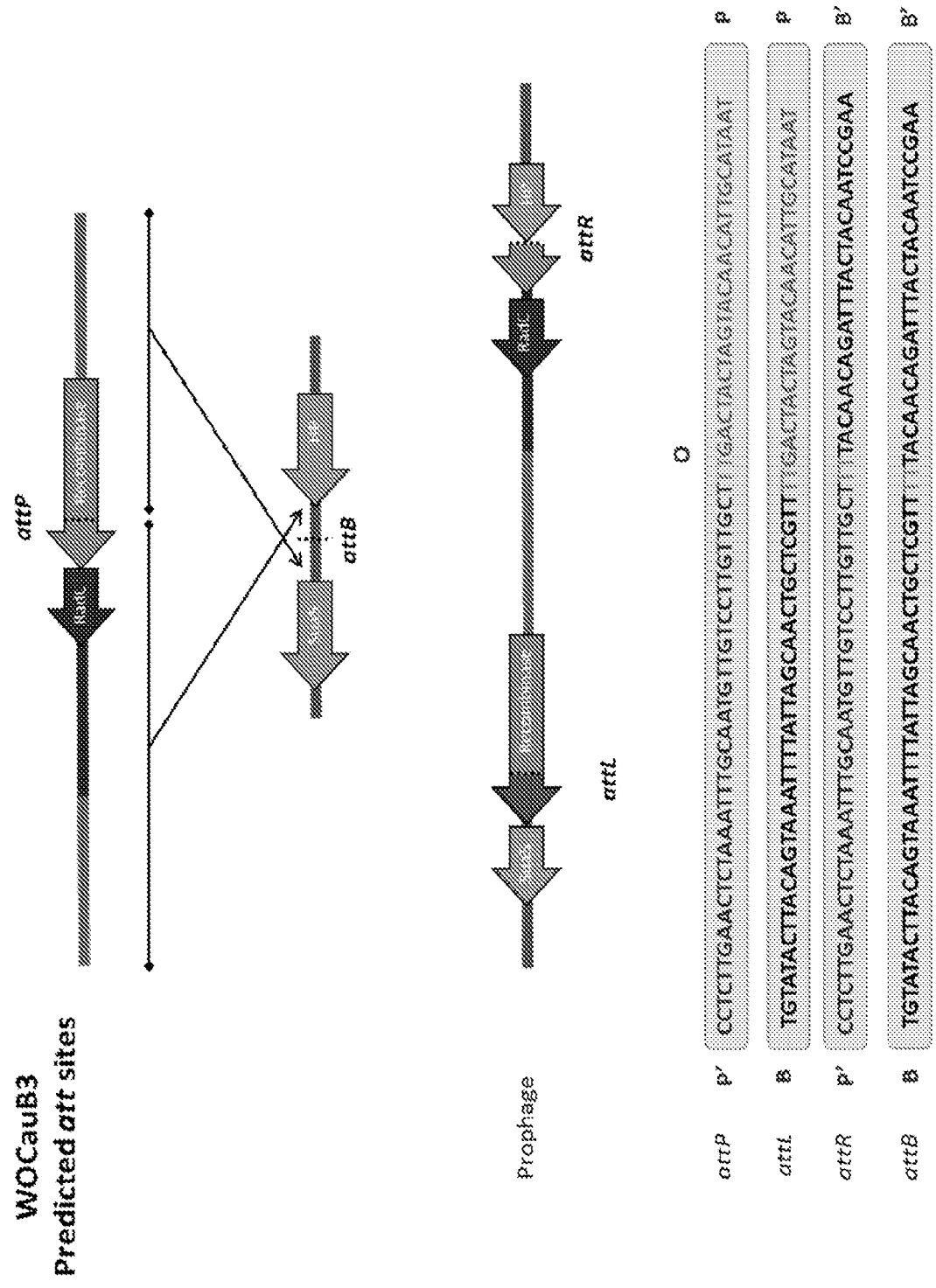

FIG. 19. WOCauB3 integrates between Sua5 and a hypothetical protein in the *Wolbachia* chromosome. It integrates via the attP (phage attachment) and attB (bacterial attachments) sites and, once integrated, the prophage is flanked by attL and attR sites. Unlike all other Family 1 phages, this haplotype does not integrate into a magnesium chelatase gene. Sequences referred to in FIG. 19 include:
SEQ ID NO:7, attL, TGTATACTTACAGTAAATTTTATT-AGCAACTGCTCGTTTTGACTACTAGTACAACATT GCATAAT;
SEQ ID NO:8, attR, CCTCTTGAACTCTAAAT-TTGCAATGTTGTCCTTGTTGCTTTTACAACAGATT-TACTAC AATCCGAA;
SEQ ID NO:9, attP, CCTCTTGAACTCTAAAT-TTGCAATGTTGTCCTTGTTGCTTTGACTACTAGTA-CAACAT TGCATAAT;
SEQ ID NO:10, attB, TGTATACTTACAGTAAATTTT-ATTAGCAACTGCTCGTTTTTACAACAGATTTAC-TACA ATCCGAA).

Figure 20:
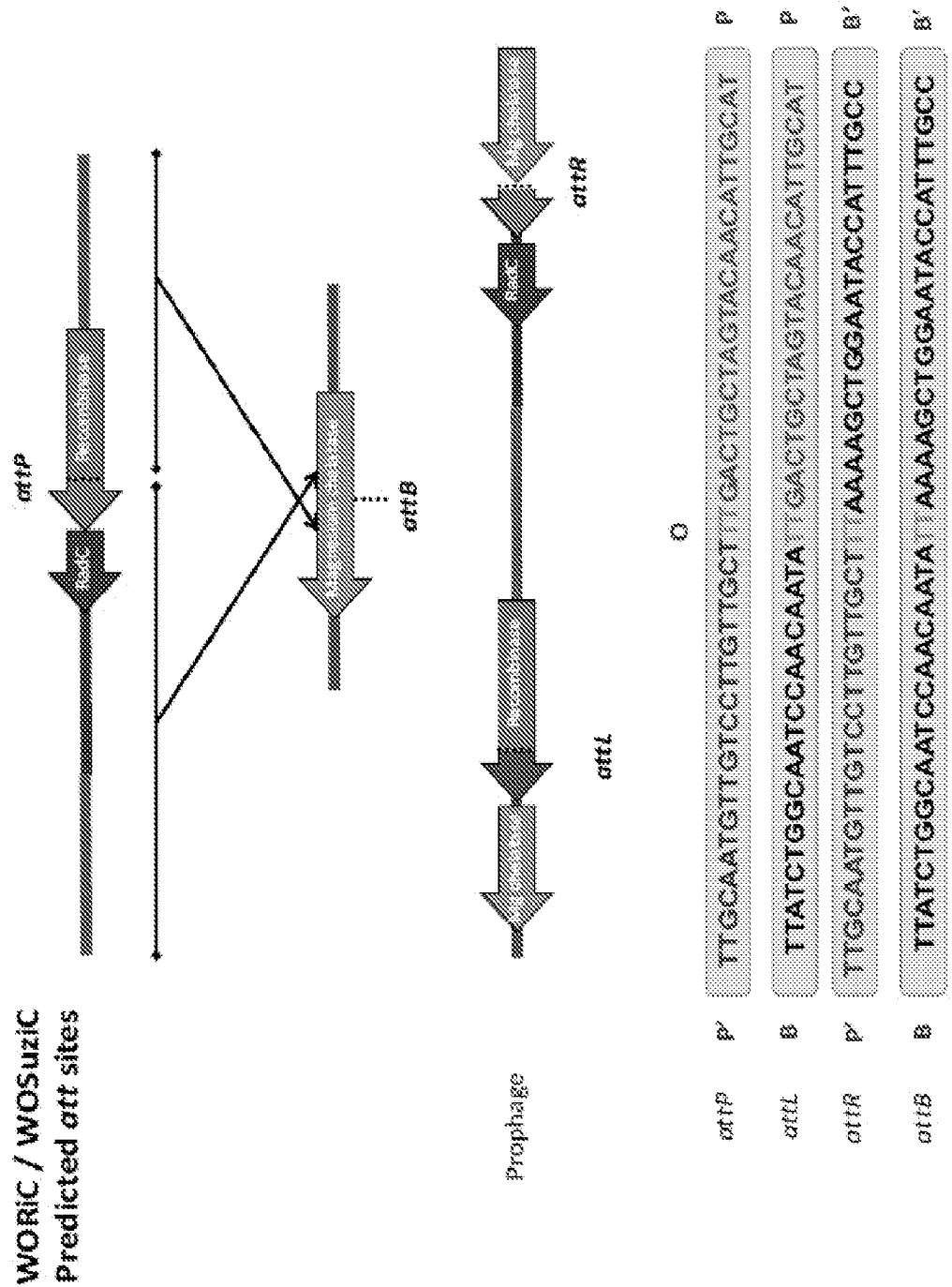

FIG. 20. WORiC and WOSuziC (Family 1) phages integrate into a magnesium chelatase gene in the *Wolbachia* chromosome. They integrate via attP (phage attachment) and attB (bacterial attachments) sites and, once integrated, the prophages are flanked by attL and attR sites. The exact nucleotide sequence is currently being predicted. Sequences referred to in FIG. 20 include:
SEQ ID NO:11, attL, TTATCTGGCAATCCAACAATAT-TGACTGCTAGTACAACATTGCAT;
SEQ ID NO:12, attR, TTGCAATGTTGTCCTTGTTGCTT-TAAAAGCTGGAATACCATTTGCC;
SEQ ID NO:13, attP, TTGCAATGTTGTCCTTGTTGCTTTGACTGCTAGTA-CAACATTGCAT;
SEQ ID NO:14, attB, TTATCTGGCAATCCAACAATAT-TAAAAGCTGGAATACCATTTGCC).

Figure 21:
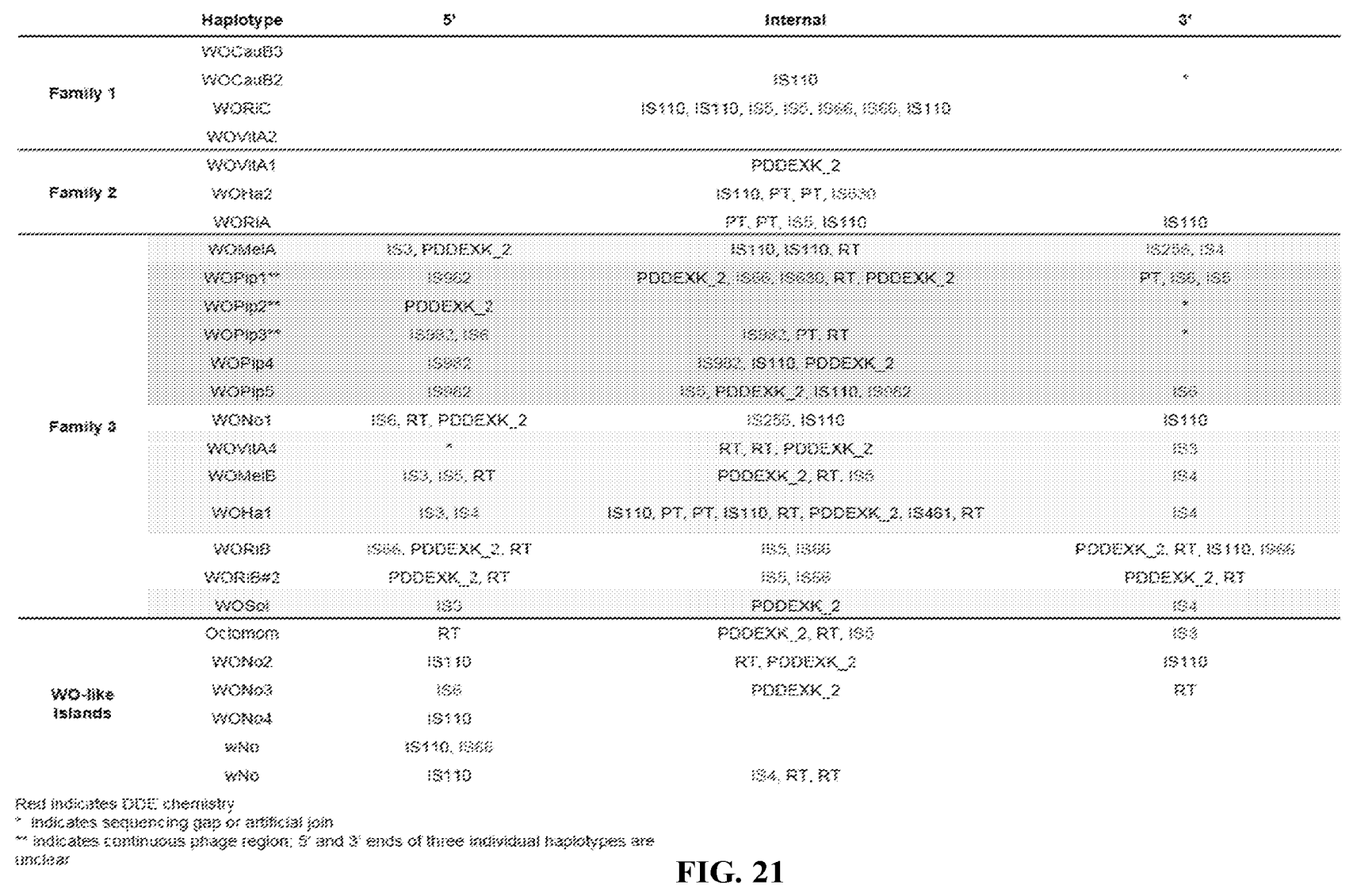

FIG. 21. Family 3 prophages are flanked by transposases at both the 5' and 3' ends. This could be indicative of (i) the preferred att site or (ii) transposable activity, such as Phage Mu. Tranposase families are listed according to their 5', 3', or internal location.

Figure 22A:
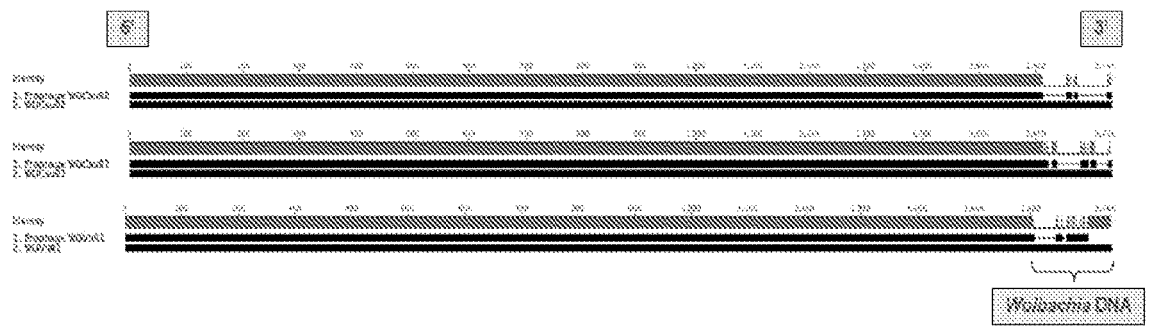
Figure 22B:
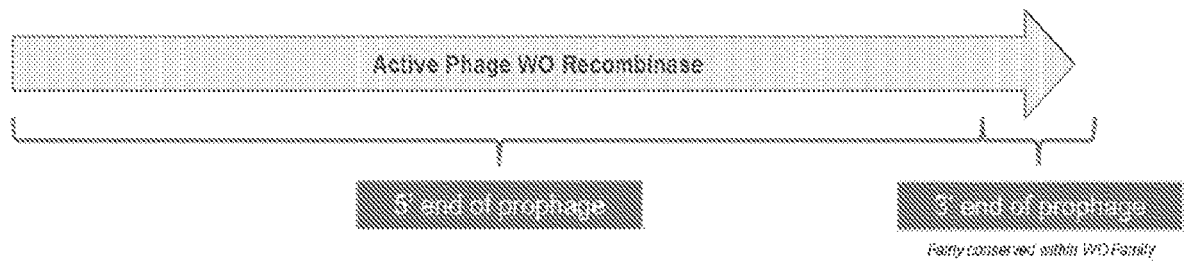
Figure 22C:
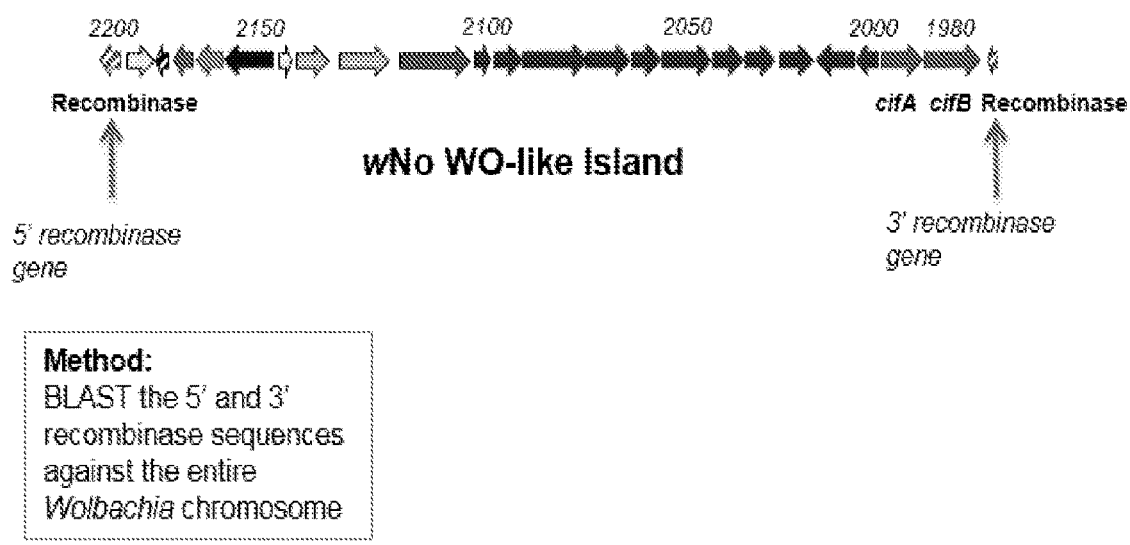

FIGS. 22A-22C. The exact prophage WO regions within a *Wolbachia* chromosome can be determined by computational analysis of the recombinase sequence. (a) A nucleotide comparison of recombinase sequences revealed that the 3' end of the gene is not shared between active phages and integrated prophages. Rather, the 3' end of the prophage recombinase contains *Wolbachia* chromosomal DNA (attB). (b) The recombinase sequence splits during integration and flanks either side of the integrated prophage in the *Wolbachia* chromosome. (c) The 5' and 3' ends of the prophage sequence can be determined by performing a nucleotide BLAST of a known active phage recombinase sequence (i.e., WOCauB2, WOCauB3, WOVitA1).

DETAILED DESCRIPTION OF THE INVENTION

Disclosed herein are systems, methods, and compositions for the genetic modification of *Wolbachia*. Previously, there has been no way to stably transform *Wolbachia* bacteria and thus no method for genetically modifying *Wolbachia* bacteria. The inventors have identified the phage attachment sequences and serine recombinase in WO phage that can be used for the genetic modification of *Wolbachia*. These compositions and methods allow the introduction of heterologous genes into the *Wolbachia* genome.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e., a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism. For example, the sequence of a heterologous gene expressed in *Wolbachia* may be "codon optimized" to optimize gene expression based on the preferred codon usage in *Wolbachia*.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a host organism (e.g. *Wolbachia* cell). In embodiments, the nucleic acid molecule may be a plasmid that replicates autonomously or it may integrate into the genome of the host organism. Host organisms containing the transformed nucleic acid molecule may be referred to as "transgenic" or "recombinant" or "transformed" organisms. A "genetically modified" organism (e.g. genetically modified *Wolbachia*) is an organism that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids.

WO Phage Transformation Systems, Methods, and Compositions

Disclosed herein are systems, methods, and compositions for the genetic modification of *Wolbachia*. Previously, there has been no way to stably transform *Wolbachia* bacteria and thus no method for genetically modifying *Wolbachia* bacteria. The inventors have identified the phage attachment sequences and serine recombinase in WO phage that can be used for the genetic modification of *Wolbachia*. These compositions and methods allow the introduction of heterologous genes into the *Wolbachia* genome.

In one aspect of the invention, provided herein is a WO phage vector that can be used to stably transform *Wolbachia*. In one aspect of the invention, disclosed herein is a WO phage transformation system, said system comprising:

a) a first DNA vector comprising a gene encoding a protein with WO phage integrase activity operably linked to a first promoter active in a host cell, and
b) a second DNA vector comprising an attachment site (attP) recognized by the WO phage integrase protein.

In one embodiment, the second DNA vector further comprises a heterologous gene. For example, the heterologous gene may be a gene from an arthropod. In one embodiment, the heterologous gene can include a reproductive parasitism gene to spread *Wolbachia* and/or its native anti-pathogen effects into hosts. In one embodiment, the heterologous gene can include a sterility or inviability gene that sterilizes or kills arthropod pests or vectors of disease. In one embodiment, the heterologous gene can include anti-pathogen genes, such as host immunity genes or those in the Octomom region of *Wolbachia* (WD0507-WD0514), that have been shown to protect insect hosts from viral infections.

In one embodiment, the second DNA vector further comprises a heterologous gene operably linked to a second promoter active in the host cell. In one embodiment, the second DNA vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter. In one embodiment, the system further comprises dendrimers. In one embodiment, the system further comprises complex G4 dendrimers.

In one embodiment, the attachment site (attP) comprises SEQ ID NO:5 (TTTTTGTAACATTGTTATACACAT-CATGACGTCCAGTACAATGTTGCAA). The attachment site (attP) can also be similar to SEQ ID NO:5, but still retain the ability to function as an attachment site for the serine recombinase. In some embodiments, the attachment site (attP) is at least 60% (for example, at least 60%, at least 65%, at least 70%, at least 75%, at least 80%, at least 85%, at least 90%, at least 95%) identical to SEQ ID NO:5.

In one embodiment, the attachment site (attB) comprises SEQ ID NO:6 (GCAAATACAATAGCTTCACTGTTAT-GATAAGGGGGCTGGCGGAGTTT). The attachment site (attB) can also be similar to SEQ ID NO:6, but still retain the ability to function as an attachment site for the serine recombinase. In some embodiments, the attachment site (attB) is at least 60% (for example, at least 60%, at least 65%, at least 70%, at least 75%, at least 80%, at least 85%, at least 90%, at least 95%) identical to SEQ ID NO:6.

In one embodiment, the attachment site (attP) comprises SEQ ID NO:9 (CCTCTTGAACTCTAAAT-TTGCAATGTTGTCCTTGTTGCTTTGACTACTAGTA-CAACAT TGCATAAT). The attachment site (attP) can also be similar to SEQ ID NO:9, but still retain the ability to function as an attachment site for the serine recombinase. In some embodiments, the attachment site (attP) is at least 60% (for example, at least 60%, at least 65%, at least 70%, at least 75%, at least 80%, at least 85%, at least 90%, at least 95%) identical to SEQ ID NO:9.

In one embodiment, the attachment site (attB) comprises SEQ ID NO:10 (TGTATACTTACAGTAAATTTTATT-AGCAACTGCTCGTTTTTACAACAGATTTACTAC AATCCGAA). The attachment site (attB) can also be similar to SEQ ID NO:10, but still retain the ability to function as an attachment site for the serine recombinase. In some embodiments, the attachment site (attB) is at least 60% (for example, at least 60%, at least 65%, at least 70%, at least 75%, at least 80%, at least 85%, at least 90%, at least 95%) identical to SEQ ID NO:10.

In one embodiment, the attachment site (attP) comprises SEQ ID NO:13 (TTGCAATGTTGTCCTTGTTGCTTTGACTGCTAGTA-CAACATTGCAT). The attachment site (attP) can also be similar to SEQ ID NO:13, but still retain the ability to function as an attachment site for the serine recombinase. In some embodiments, the attachment site (attP) is at least 60% (for example, at least 60%, at least 65%, at least 70%, at least 75%, at least 80%, at least 85%, at least 90%, at least 95%) identical to SEQ ID NO:13.

In one embodiment, the attachment site (attB) comprises SEQ ID NO:14 (TTATCTGGCAATCCAACAATAT-TAAAAGCTGGAATACCATTTGCC). The attachment site (attB) can also be similar to SEQ ID NO:14, but still retain the ability to function as an attachment site for the serine recombinase. In some embodiments, the attachment site (attB) is at least 60% (for example, at least 60%, at least 65%, at least 70%, at least 75%, at least 80%, at least 85%, at least 90%, at least 95%) identical to SEQ ID NO:14.

In one aspect of the invention, disclosed herein is a WO phage transformation system, said system comprising:
  a) a protein with WO phage integrase activity, and
  b) a DNA vector comprising an attachment site (attP) recognized by the WO phage integrase protein.

In one aspect of the invention, disclosed herein is a WO phage transformation system, said system comprising:
  a) an mRNA encoding a protein with WO phage integrase activity, and
  b) a DNA vector comprising an attachment site (attP) recognized by the WO phage integrase protein.

In one embodiment, the DNA vector further comprises a heterologous gene. For example, the heterologous gene may be a gene from an arthropod. In one embodiment, the heterologous gene can include a reproductive parasitism gene to spread Wolbachia and its native anti-pathogen effects into hosts. In one embodiment, the heterologous gene can include a sterility gene that sterilizes arthropod pests or vectors of disease. In one embodiment, the heterologous gene can include an anti-pathogen gene, such as Octomom (WD0507-WD0514), that have been shown to protect insect hosts from viral infections.

In one embodiment, the DNA vector further comprises a heterologous gene operably linked to a second promoter active in the host cell. In one embodiment, the DNA vector further comprises a selectable marker. The selectable marker can be, for example, a tetracycline resistance marker.

In one embodiment, the protein with WO phage integrase activity is a serine recombinase. In one embodiment, the serine recombinase is encoded by SEQ ID NO:1. This sequence can be codon optimized, can differ due to the degeneracy of the genetic code, or can be similar to SEQ ID NO:1, but still retain the serine recombinase activity. In some embodiments, the serine recombinase is at least 60% (for example, at least 60%, at least 65%, at least 70%, at least 75%, at least 80%, at least 85%, at least 90%, at least 95%) identical to SEQ ID NO:1.

```
Serine recombinase (gwv_1156) DNA sequence:
(Located within Accession # HQ906662)
                                         (SEQ ID NO: 1)
TTGAATGAGTATGAATTTAAGGATGATGGGCTTAGTGGGTGGAGTTTAGA

ACGTGAAGGTTTAGATGCATTACGTGATAAAGTAGGAGAAGATCAAATTG
```

```
ATAAAATTTATATTCATTCACCTGACCGACTATCAAGAAAATCTGCACAT

CAAATGATATTACTTGATGAATTTGAAAAAGCAGGAGTAGAAGTAATATT

CTTAAATCATAAGACTGAAAATAATCCAGAGTCTAAATTGTTATTAGGAA

TGCAAGGATTAGTGGCAGAATATGAGTGTACAAAGATTATGGAACGTAGT

CGTAGGGAAAACTCCATAGAGCAAAAAAAGGCTGTGTAAGTGTAATTGG

CATTGCACCTTTTGGTTATAATCGTATAAAGCATGTAGATAGAGAAAAGA

CAAAGTTTGAAATAAATGAAGAGGAAGCAAAAATAGTAAAGCAGATGTTC

ATGTGGGTAGGGCAAGAGAGAATAAGTATAAGGGAAGTGGTACGTAGACT

AAGAGATAAGTCAATTAGAACAAGAACTGGAAAGAAGGTGTGGTGTCCAA

TAATAATTTGGAAGTTATTAAGAAATCCAGCATATAAAGGACAAGCAGCG

TTTGGTAAATTAAAGAGGGTTGAAAGAAGAGAAAGAAATAAACAAAAGGT

TTCTATCTGTCGCACAGATGAGGACAGCTGGATTTATATACCAGTACCAA

AAATAGTTGATGAAGGGTTATTTAATAAAGTACAAAAGCAACTGGATGAA

AATAGAAAAAGAGCAAGGATACAGAGAGAGGGAGGAAAAAAGAAATATCT

ATTACAAGGTCTAGTTGTGTGTCAAAACTGTGGATATGCGTATAGTGGTG

CACAATGTGGAGTTGAGGGAAAGAAGTTTAGCTATTATCGCTGTAGTAGT

ACTATACGTATTACTGATGGTAGGGAGAAGTGTACTAATAAATTGGTCCG

TACAGATATGTTAGAAACAGCTATATGGGAAAAGGTGAAAAATTTACTAA

AAAACCCAGAGATAATAAAAAATGAGTATCACCGTAGAATTGCAGAAAAT

AAAAATGATGAATCATCAGATAAGAAGTTTGCAAGAAGGGAAAATCAAAT

AAAACAAGGCATCGAAAAGTTAATGGAAGACTATTATAGTCAAGAAAATG

TAGGAGATAAAGGATATATAAGTAAGGAAGAATTTAAACAGACGATGAAA

AGAATGAGGGAACGCTTAAGAGGGATAGAAGAAGAGAAGAAAAAGGTAGC

TGATCAAAAAGCAATAGAGAAGGGAATGAACCTTATCATCAACAGTATAA

AGAGTCTTTATTCCAGTGTAAAATCTAATTTGGAACAGCTAGATTGGCAA

ACTAAGCGTGGCATCATTAAAGCATTAGTAGAACGAATTCAAATTGGTTA

TGACCAGGTAGAAGTGGCGTTTAGAATCGAAGAACCAGCACAGGGTGGAG

AGATTTTTAATTTGCAACATTGTACTGGACGTCATAACAGTGAAGCTATT

GTATTTGCTTTCGCCAATCTGCAGATTAAAAGGTAA
```

In one embodiment, the serine recombinase comprises SEQ ID NO:2. The serine recombinase used can also be similar to SEQ ID NO:2, but still retain the serine recombinase activity. In some embodiments, the serine recombinase is at least 60% (for example, at least 60%, at least 65%, at least 70%, at least 75%, at least 80%, at least 85%, at least 90%, at least 95%) identical to SEQ ID NO:2. In some embodiments, a fragment of a protein with WO phage integrase activity is used. In some embodiments, a fragment of SEQ ID NO:2 retaining integrase (recombinase) activity is used in the methods herein.

```
Serine recombinase (gwv_1156) amino acid sequence:
(Accession # ADW80128.1)
                                         (SEQ ID NO: 2)
MNEYEFKDDGLSGWSLEREGLDALRDKVGEDQIDKIYIHSPDRLSRKSAH

QMILLDEFEKAGVEVIFLNHKTENNPESKLLLGMQGLVAEYECTKIMERS
```

-continued

RRGKLHRAKKGCVSVIGIAPFGYNRIKHVDREKTKFEINEEEAKIVKQMF

MWVGQERISIREVVRRLRDKSIRTRTGKKVWCPIIIWKLLRNPAYKGQAA

FGKLKRVERRERNKQKVSICRTDEDSWIYIPVPKIVDEGLFNKVQKQLDE

NRKRARIQREGGKKKYLLQGLVVCQNCGYAYSGAQCGVEGKKFSYYRCSS

TIRITDGREKCTNKLVRTDMLETAIWEKVKNLLKNPEIIKNEYHRRIAEN

KNDESSDKKFARRENQIKQGIEKLMEDYYSQENVGDKGYISKEEFKQTMK

RMRERLRGIEEEKKKVADQKAIEKGMNLIINSIKSLYSSVKSNLEQLDWQ

TKRGIIKALVERIQIGYDQVEVAFRIEEPAQGGEIFNLQHCTGRHNSEAI

VFAFANLQIKR

In one embodiment, the first promoter or the second promoter is a *Wolbachia* surface protein (wsp) promoter. In one embodiment, the system further comprises dendrimers. In one embodiment, the system further comprises dendrimers. In one embodiment, the system further comprises complex G4 dendrimers.

In one aspect of the invention, disclosed herein is a WO phage vector, said vector comprising:
a) a gene encoding a protein with WO phage integrase activity operably linked to a first promoter active in a host cell;
b) a second attachment site (attP) recognized by the WO phage integrase protein, and
c) a heterologous gene.

In one embodiment, the heterologous gene is operably linked to a second promoter active in the host cell. In one embodiment, the vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter.

In another aspect, disclosed herein is a genetically modified *Wolbachia* cell, wherein said *Wolbachia* cell is a symbiont of an insect, wherein the *Wolbachia* cell is transformed to express a heterologous gene, wherein the expression of the heterologous gene decreases the ability of the insect to transmit a pathogen.

In another aspect, disclosed herein is a genetically modified *Wolbachia* cell, wherein said *Wolbachia* cell is a symbiont of an insect, wherein the *Wolbachia* cell is transformed to express a heterologous gene, wherein the expression of the heterologous gene decreases the reproductive potential of the insect.

In another aspect, disclosed herein is a genetically modified *Wolbachia* cell, wherein said *Wolbachia* cell is a symbiont of an insect, wherein the *Wolbachia* cell is transformed to express a heterologous gene, wherein the expression of the heterologous gene sterilizes the insect.

In another aspect, provided herein is a genetically modified *Wolbachia* cell wherein said *Wolbachia* cell is a symbiont of an insect, wherein the *Wolbachia* cell is transformed to express a double stranded RNA, wherein the dsRNA decreases the expression of at least one selected target gene of the insect.

In one embodiment, the insect is an arthropod. In one embodiment, the arthropod is a mosquito. In one embodiment, the mosquito is selected from the genera consisting of *Aedes*, *Culex* and *Anopheles*. In one embodiment, the mosquito is an *Aedes* mosquito. In one embodiment, the mosquito is an *Anopheles* mosquito. In one embodiment, the mosquito is a *Culex* mosquito. In one embodiment, the *Aedes* mosquito species is selected from the group consisting of *Aedes albopictus*, *Aedes aegypti* and *Aedes polynesiensis*. In one embodiment, the *Anopheles* mosquito species is *Anopheles gambiae*. In one embodiment, the *Culex* mosquito species is *Culex pipiens*. In one embodiment, the insect is *Drosophila suzukii*.

In one embodiment, the pathogen is selected from dengue virus, Zika virus, a malaria parasite (*Plasmodium* genus), West Nile virus, yellow fever virus, chikungunya virus, Japanese encephalitis, St. Louis encephalitis and Western and Eastern Equine Encephalitis viruses.

In a further aspect of the invention, disclosed herein is a method for the genetic modification of a DNA of a *Wolbachia* cell comprising in its genome a first attachment site (attB) recognized by a protein with WO phage integrase activity, comprising introducing a WO phage transformation system into the cell, said system comprising:
a) a first DNA vector comprising a gene encoding a protein with WO phage integrase activity operably linked to a first promoter active in the *Wolbachia* cell, and
b) a second DNA vector comprising a second attachment site (attP) recognized by the integrase protein.

In one embodiment, the second DNA vector further comprises a heterologous gene. For example, the heterologous gene may be a gene from an arthropod. In one embodiment, the second DNA vector further comprises a heterologous gene operably linked to a second promoter active in the host cell. In one embodiment, the second DNA vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter.

In a further aspect of the invention, disclosed herein is a method for the genetic modification of a DNA of a *Wolbachia* cell comprising in its genome a first attachment site (attB) recognized by a protein with WO phage integrase activity, comprising introducing a WO phage transformation system into the cell, said system comprising:
a) a protein with WO phage integrase activity, and
b) a DNA vector comprising a second attachment site (attP) recognized by the WO phage integrase protein.

In a further aspect of the invention, disclosed herein is a method for the genetic modification of a DNA of a *Wolbachia* cell comprising in its genome a first attachment site (attB) recognized by a protein with WO phage integrase activity, comprising introducing a WO phage transformation system into the cell, said system comprising:
a) an mRNA encoding a protein with WO phage integrase activity, and
b) a DNA vector comprising a second attachment site (attP) recognized by the WO phage integrase protein.

In one embodiment, the DNA vector further comprises a heterologous gene. For example, the heterologous gene may be a gene from an arthropod. In one embodiment, the DNA vector further comprises a heterologous gene operably linked to a second promoter active in the host cell. In one embodiment, the DNA vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter.

In one aspect, disclosed herein is a method for the genetic modification of a DNA of a *Wolbachia* cell comprising in its genome a first attachment site (attB) recognized by a protein with WO phage integrase activity, comprising introducing a WO phage vector, said vector comprising:
a) a gene encoding a protein with WO phage integrase activity operably linked to a first promoter active in a host cell;
b) a second attachment site (attP) recognized by the WO phage integrase protein, and
c) a heterologous gene.

In one embodiment, the heterologous gene is operably linked to a second promoter active in the host cell. In one embodiment, the vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter.

Methods of Treating Filarial Infections

*Wolbachia pipientis* is well known for its parasitic phenotypes, yet it also has a mutualistic relationship with several invertebrate species. The archetypal example occurs in filarial nematodes, in which 47% of the Onchocercidae family are infected by *Wolbachia*, and both host and bacteria are completely dependent upon each other. Interestingly, almost every disease-causing species of filarial nematode are infected with *Wolbachia*. A watershed moment in the science of filarial diseases occurred when studies implicated *Wolbachia* as the chief cause of debilitating ailments such as river blindness and lymphatic filariasis. The nature of this mutualism is slowly being elucidated, and there is strong evidence that the bacteria provide essential nutrients to the host, including riboflavin, heme, and flavin adenine dinucleotide (FAD). Recently, based on genome and transcriptome sequencing of *Onchocerca* worms, it was suggested that *Wolbachia* play a defensive, antibacterial role and have possible mitochondria-like actions such as providing energy and metabolites. These observations are supported by work that shows dramatic increases in *Wolbachia* titers when the host is undergoing high levels of growth and division that demand increased metabolism.

The symbiosis between *Wolbachia* and filarial nematodes is tightly controlled. Studying specific cell lineages, it has been found that the parasite positions itself in the hypodermal chords of developing zygotes and later is able to specifically invade the gonads before sexual maturity is achieved. The nematode maintains strict control over this interaction through host autophagy. This inter-dependence is reinforced by horizontal gene transfer between the bacteria and host, such as in *Brugia malayi*. There is also growing evidence that other filarial nematodes exist independent of *Wolbachia* and may have lost the bacteria after an ancient infection.

Although *W. pipientis* is required in many filarial nematodes, its mutualistic relationships with arthropods are more varied. In *Aedes polynesiensis*, infection is associated with decreased larval mortality and increased adult lifespan. In other species, such as *C. pipiens quinquefasciatus* and brown planthoppers, *Wolbachia* increases the number of embryos surviving to adulthood but decreases adult lifespan. In *A. aegypti*, however, *Wolbachia* decreases embryo survivability, and in the moth *Ephestia kuehniella*, infection reduces the number of viable sperm. In other species, such as rice water weevils and the wasp *Asorbara tabida*, a *Wolbachia* infection is absolutely required for oogenesis. Finally in *Drosophila mauritiana*, *Wolbachia* infections in the ovarian stem cells accelerate mitosis, leading to a fourfold increase in egg numbers compared to uninfected counterparts. While these various phenotypes show little correlation with each other, one interesting hypothesis is that they might represent various stages of a parasitic-to-mutualistic continuum between *Wolbachia* and invertebrate hosts. A mutualistic or codependent relationship would be beneficial for both organisms and could be selected for over time. Interestingly, this exact transition has been observed in nature over the course of just a few decades with fruit flies.

In contrast to spreading the *Wolbachia* reproductive parasites in arthropods for vector control, the profound health repercussions for *Wolbachia* mutualisms are based on eliminating them. Specifically, in the filarial nematodes, curing *Wolbachia* can halt nematode growth, encourage apoptosis, and eventually lead to death of the worm. These nematodes cause diseases such as lymphatic filariasis and onchocerciasis, which together account for 140 million infections a year. These afflictions threaten 1.4 billion people annually, yet alarmingly over 20 years have passed since the last anti-filarial drug was developed. More importantly, current treatment protocols are losing efficacy, and resistance is of growing concern.

Research into *Wolbachia*-nematode interactions was boosted after the genomes for the main causative factor of lymphatic filariasis, *B. malayi*, and its *Wolbachia* symbiont, wBm, were published. These studies enabled comparative genomic analyses of the pathways that complement missing functions in both the host and symbiont. As mentioned before, this work showed that *B. malayi* is reliant on factors such as riboflavin, heme, and FAD produced by the bacteria. Interestingly, it also revealed many of the specific metabolites that *Wolbachia* requires from its host. These include coenzyme A, biotin, and nicotinamide adenine dinucleotide (NAD), as well as ubiquinone, lipoic acid, folate, and pyridoxal phosphate. Whether any of these pathways can be successful drug targets is yet to be determined. Further candidates can also be elucidated as comparative genomics of nematodes and their *Wolbachia* continues with the more recent analyses of the uninfected nematode, *Loa loa* and the F group *Wolbachia*.

In addition to the factors mentioned above, other work has focused on identifying specific *Wolbachia* pathways and their role in the host-symbiont relationship. Initial results have recognized heme biosynthesis, DNA ligases, FtsZ, ClpP peptidase, lipoprotein biosynthesis, and pyruvate phosphate dikinase (PPDK) in the bacteria as promising targets for drug development. While these pathways share little in common, the broad range of treatment candidates that they represent could enable *Wolbachia*-specific therapy. Finally, in a directed effort to discover drugs that treat river blindness and filariasis, the Anti-*Wolbachia* Consortium (A-WOL) has recently begun screening compounds that can target the infection in a mosquito cell line. These efforts have looked at over 2600 current drugs as well as 67 000+ other compounds with full results coming soon.

The race to find new anti-filarial and anti-*Wolbachia* treatments is urgent. Despite success in eliminating nematode infections with doxycycline in small groups of individuals, the lengthy treatment regimes, the potential for evolution of widespread antibiotic resistance in the endogenous microflora, and restrictions against use in children and pregnant women make massive administration of doxycycline problematic. Indeed, the gut flora of treated individuals could act as a reservoir for drug resistance genes, and intracellular bacteria, while more restricted in horizontal gene transfer than free living species, have still shown a capacity to gain resistance. There is still hope for alternative drugs, such as an anti-filarial vaccine, to supplement current treatments. In fact, recent work shows that mice immunized with a single *Wolbachia* protein show strong, although not complete, resistance to nematode infection. More treatment avenues will also open as in-depth research is conducted on the recently sequenced genomes of several filarial nematode species and their accompanying *Wolbachia* infections.

Previous treatments targeted the filarial worm itself with drugs such as ivermectin. However, ivermectin is known to have toxicity problems. Thus, recent approaches have used antibacterial agents, such as doxycycline, to treat the filarial infection, by treating the symbiont bacterial infection. Thus, in one embodiment, the WO phage can be useful to treat a veterinary disease which is caused by infection with a filarial worm.

In one aspect, provided herein is a method for treating a filarial nematode infection in a host, comprising the steps: administering a WO phage vector to the host, said vector comprising:
a) a gene encoding a protein with WO phage integrase activity operably linked to a first promoter active in the host cell, and
b) an attachment site (attP) recognized by the WO phage integrase protein;
wherein delivery of the WO phage vector into a *Wolbachia* cell causes lysis or inhibits the growth of the *Wolbachia* cell.

In one embodiment, the administration of the WO phage vector to a host causes lysis of the *Wolbachia* cell. In one embodiment, the administration of the WO phage vector to a host inhibits the growth of the *Wolbachia* cell.

In one embodiment, the heterologous gene is operably linked to a second promoter active in the host cell. In one embodiment, the vector further comprises a selectable marker. The selectable marker can be, for example, a tetracycline resistance marker.

In one embodiment, the protein with WO phage integrase activity is a serine recombinase. In one embodiment, the first promoter or the second promoter is a *Wolbachia* surface protein (wsp) promoter.

In one embodiment, the filarial infection is *Onchocerca volvulus* (river blindness). In one embodiment, the filarial infection is selected from *Wuchereria bancrofti*, *Brugia malayi* or *B. timori*. (lymphatic filariasis). In one embodiment, the filarial infection is *Dirofilaria immitis* (canine heartworm).

In some embodiments, the WO phage vector can be used to treat veterinary diseases due to infection with filarial worms.

Arthropods and Population Replacement Strategies

The Eliminate Dengue Program (EDP) was originally established in Australia with the aim of using *Wolbachia*-based strategies to curb the spread of dengue, a mosquito-borne disease. Early efforts focused on using the wMelPop strain of *Wolbachia*, but in 2011, the EDP stably infected the mosquito vector of dengue, *Aedes aegypti*, with the wMel *Wolbachia* strain from *D. melanogaster*. The feat was accomplished by passaging the bacteria for several years in an *Aedes albopictus* cell line before microinjection into the mosquitoes. The long term in vitro cultivation in mosquito cells led to attenuated virulence in the mosquito species in vivo and a normal host lifespan; yet, remarkably the wMel strain retained high rates of maternal transmission, the capacity to spread through experimental populations by CI, and the crucial refractoriness to dengue virus. Controlled release of these mosquitoes into a small number of Australian neighborhoods effectively replaced the native population with a dengue-free vector. While data on whether the population replacement has reduced the incidence of human dengue cases can take many years to assess, the EDP is quickly scaling their approach throughout the world. Recent estimates suggest that dengue infects 390 million people per year with 96 million showing some level of disease severity. The vast majority of these cases are in Southeast Asia and South America where the EDP has research centers in China, Indonesia, Vietnam, and Brazil. These locations give the EDP a growing influence in the spread of dengue among the most heavily affected areas in the world.

The success of the EDP has inspired a broad push to identify applications for *Wolbachia* in other disease vectors. Of particular interest are the anopheline mosquitoes, the main carriers of malaria. Every sampled species of *Anopheles* lacks *Wolbachia*, and while *Anopheles gambiae* can be somatically infected by *Wolbachia* strains from *D. melanogaster* and *Aedes albopictus*, stable germ line infection with high maternal transmission has historically been difficult. Recently, however, that hurdle was overcome by stably infecting anopheline mosquitoes with microinjections of *Wolbachia* into eggs. The resultant mosquitoes show few defects, induce CI, and cause refractoriness to *Plasmodium* infection. This exciting new work now places *Wolbachia*-based control of mosquitoes that transmit malaria within sight.

There has also been work to identify the infection status of other mosquito species to test the applicability of population replacement by *Wolbachia* in the vectors of yellow fever and lymphatic filariasis. Additionally, *Wolbachia* have been proposed as a possible means to control bed bugs and tsetse flies. In bed bugs, resistance to pyrethroid insecticides is common, and thus alternative methods using *Wolbachia* are welcome developments. Finally, the use of *Wolbachia* in tsetse flies is especially enticing, as they spread trypanosomes and sleeping sickness, and *Wolbachia* are already known to induce CI in some tsetse species.

EXAMPLES

The following examples are set forth below to illustrate the systems, methods, compositions and results according to the disclosed subject matter. These examples are not intended to be inclusive of all aspects of the subject matter disclosed herein, but rather to illustrate representative systems, methods, compositions and results. These examples are not intended to exclude equivalents and variations of the present invention which are apparent to one skilled in the art.

Example 1. Identification of WO Phage Attachment Sites and Serine Recombinase

Viruses are trifurcated into eukaryotic, archaeal and bacterial categories. This domain-specific ecology underscores why eukaryotic genes are typically co-opted by eukaryotic viruses and bacterial genes are commonly found in bacteriophages. However, the presence of bacteriophages in symbiotic bacteria that obligately reside in eukaryotes may promote eukaryotic DNA transfers to bacteriophages. By sequencing full genomes from purified bacteriophage WO particles of *Wolbachia*, a novel eukaryotic association module was discovered with various animal proteins domains, such as the black widow latrotoxin-CTD, that are uninterrupted in intact bacteriophage genomes, enriched with eukaryotic protease cleavage sites, and combined with additional domains to forge some of the largest bacteriophage genes (up to 14,256 bp). These various protein domain families are central to eukaryotic functions and have never before been reported in packaged bacteriophages, and their phylogeny, distribution and sequence diversity implies lateral transfer from animal to bacteriophage genomes. The evolution of these eukaryotic protein domains in bacteriophage WO may parallel the evolution of eukaryotic genes in canonical eukaryotic viruses, namely those commandeered for viral life cycle adaptations. Analogous selective pressures and evolutionary outcomes may occur in bacteriophage WO as a result of its "two-fold cell challenge" to persist in and traverse cells of obligate intracellular bacteria that strictly reside in animal cells.

Viruses are the most abundant and diverse biological entities in the biosphere (Edwards, R. A. & Rohwer, F. *Nat Rev Microbiol* 3, 504-10 (2005); Hendrix, R. W., et al. *Proc Natl Acad Sci USA* 96, 2192-7 (1999)). Infecting organisms across the tree of life, they associate with every ecosystem on the planet (Suttle, C. A. *Nature* 437, 356-61 (2005)). They are generally classified into polythetic groups according to ecological niche and mode of replication (Brussow, H. *Philos Trans R Soc Lond B Biol Sci* 364, 2263-74 (2009); King, A. M. Q., et al. Virus taxonomy: classification and nomenclature of viruses: Ninth Report of the International Committee on Taxonomy of Viruses., 1327 (Elsevier, San Diego, 2012)). While any cellular domain can be infected by a virus, no extant virus is known to traverse more than one domain (Nasir, A., et al. *Front Microbiol* 5, 194 (2014); Prangishvili, D., et al. *Nat Rev Microbiol* 4, 837-48 (2006)). This domain-specific ecology of viruses underpins the current taxonomic paradigm of trifurcating viruses into eukaryotic, archaeal and bacterial categories, along with recent reappraisals of whether viruses constitute a fourth domain of life (Forterre, P. *Intervirology* 53, 362-78 (2010); Raoult, D. *Intervirology* 56, 349-53 (2013); Nasir, A. & Caetano-Anolles, G. *Science Advances* 1(2015)). As a result of this domain-specific ecology, viruses often integrate host genes via specific highways of lateral gene transfer. Eukaryotic viruses tend to hijack genes directly from their eukaryotic hosts to evade, manipulate and counter-strike anti-viral immune responses (Elde, N. C. & Malik, H. S. *Nat Rev Microbiol* 7, 787-97 (2009); Rappoport, N. & Linial, M. *PLoS Comput Biol* 8, e1002364 (2012)), with the exception of some giant viruses that appear to acquire genes from all domains of life (Colson, P. & Raoult, D. Intervirology 53, 330-43 (2010)). Bacterial viruses, or bacteriophages (phages), only integrate genetic material from their bacterial hosts including toxin (Canchaya, C., et al. *Mol Microbiol* 53, 9-18 (2004)), photosynthesis (Lindell, D. et al. *Proc Natl Acad Sci USA* 101, 11013-8 (2004)) and pigment biosynthesis genes (Dammeyer, T., et al. *Curr Biol* 18, 442-8 (2008)) that contribute to the fitness of their bacterial host. To date, however, there is no archetypal case of phage particles harboring genomes with eukaryotic DNA.

While all viruses are specific to one of the three domains of life, some bacteriophages target obligate intracellular bacteria of eukaryotic cells. For instance, phage WO infects the obligate intracellular alpha-proteobacteria *Wolbachia*, which in turn infect an estimated 40% of the most speciose group of animals worldwide—arthropods (as well as filarial nematodes). They cause a range of host reproductive pathologies (Werren, J. H., et al. *Nat Rev Microbiol* 6, 741-51 (2008); Zug, R. & Hammerstein, P. *PLoS One* 7, e38544 (2012)), primarily infect the cells of host reproductive tissues, exist in Golgi-derived vesicles within the eukaryotic cytoplasm, and are enclosed by a bacterial cell membrane and one or more eukaryotic-derived membranes (Cho, K. O., et al. *PLoS One* 6, e22703 (2011); Henrichfreise, B. et al. *Mol Microbiol* 73, 913-23 (2009); Louis, C. & Nigro, L. et al. *Journal of Invertebrate Pathology* 54, 39-44 (1989)). Nearly all sequenced *Wolbachia* genomes, with the exception of those acting as obligate mutualists, harbor prophage WO (Gavotte, L. et al. *Mol Biol Evol* 24, 427-35 (2007); Kent, B. N. & Bordenstein, S. R. *Trends Microbiol* 18, 173-81 (2010); Metcalf, J. A. & Bordenstein, S. R. *Curr Opin Microbiol* 15, 546-52 (2012)). They encode conserved structural modules (e.g., head, tail, baseplate) and exhibit Caudovirales morphology in electron micrographs of purified phages (Kent, B. N. & Bordenstein, S. R. *Trends Microbiol* 18, 173-81 (2010); Chauvatcharin, N., et al. *Mol Ecol* 15, 2451-61 (2006); Fujii, Y., et al. *Biochem Biophys Res Commun* 317, 1183-8 (2004); Masui, S. et al. *Biochem Biophys Res Commun* 283, 1099-104 (2001); Sanogo, Y. O. & Dobson, S. L. *Insect Biochem Mol Biol* 36, 80-5 (2006); Tanaka, K., et al. *Appl Environ Microbiol* 75, 5676-86 (2009); Wright, J. D., et al. *J Ultrastruct Res* 63, 79-85 (1978)). Electron microscopy and quantitative analyses indicate that prophages undergo a lytic phase capable of rupturing bacterial and eukaryotic cell membranes, and phage WO occurs in the extracellular matrix of arthropod gonads (Masui, S. et al. *Biochem Biophys Res Commun* 283, 1099-104 (2001); Bordenstein, S. R., et al. *PLoS Pathog* 2, e43 (2006)). Therefore, phage WO appears to uniquely contend with the cellular exit, entry and defense mechanisms of two separate domains of life. WO is also a promising tool for genome editing of *Wolbachia* that has thus far been refractory to genetic modification. Until now, the genomes of bacteriophage WO particles have not been fully sequenced and assembled into circular genomes, and their attachment sites and bacterial integration sites were unresolved.

In this example, the first metagenomic analysis of phage WO particles from wVitA-infected *Nasonia giraulti* wasps and wCauB-infected *Ephestia kuehniella* moths are reported. The phage attachment sites and insertion regions were identified and fully sequenced genomes show that WO harbor all formerly described phage genetic modules (lysogeny, baseplate, head, replication, virulence, tail and patatin (Kent, B. N., et al. *PLoS One* 6, e24984 (2011)) as well as a new group of genes with atypical protein domains indicative of eukaryotic interaction. These genes, which include one of the largest genes in bacteriophages to date, are collectively grouped into a novel "Eukaryotic Association Module" (EAM, white box, FIG. 1). The EAM features genes that (i) encode protein domains and cleavage sites central to eukaryotic functions, (ii) frequently undergo horizontal transfer between phage and metazoan hosts, (iii) can be much longer (up to 14,256 bp) than those in the bacterial chromosome, (iv) are absent from mutualistic, phage-free genomes such as the bedbug-infecting wCle (Hosokawa, T., et al. *Proc Natl Acad Sci USA* 107, 769-74 (2010)) and filarial nematode-infecting wBm and wOo (Darby, A. C. et al. *Genome Res* 22, 2467-77 (2012); Foster, J. et al. *PLoS Biol* 3, e121 (2005)). They occur in all complete phage WO haplotypes (Table 1).

TABLE 1

Comparative genomics of phage WO.

| GENOME | CORE PHAGE REGION | EAM REGION | (WD0611-WD0621)-like |
|---|---|---|---|
| WOVitA1 | gwv_1104-gwv_1156 | gwv_1089-gwv_1103 | na |
| WOVitA2 | gwv_426-gwv_459 | gwv_458-gwv_472; gwv_484-gwv_496 | gwv_473-gwv_483 |
| WOVitA4 | gwv_146-gwv_175 | gwv_131-gwv_145(T); gwv_176-gwv_178 | na |
| WOCauB2 | gp1-gp45 | gp46-(partial sequence) | na |
| WOCauB3 | gp1-gp44 | gp45-GF2gp25 | na |
| WOSol | So0001-So0022 | wSo0003(T)-wSo0014; So0023-So0025; So0026-wSo0028(T) | wSo0015-wSo0026 |
| WOMelA | WD0259-WD0288 | WD0289-WD0296(T); WD0253(T)-WD0258 | na |
| WOMelB | WD0634-WD0647(T); WD0563(T)-WD0604 | WD0605-WD0610; WD0622-WD0633 | WD0611-WD0621 |
| wMel WO-Island | na | WD0507-WD0514 | na |
| WOPip1 | WP0236(T)-WP0272 | WP0273-WP0293 | na |
| WOPip2 | WP0297-WP0322 | WP0294-WP0296 | na |
| WOPip3 | WP0323-WP0342 | WP0343(T)-WP0354 | na |
| WOPip4 | WP0411-WP0455 | WP0405(T)-WP0410; WP0456-WP0465 | na |
| WOPip5 | WP1294(T)-WP1340 | WP1289(T)-WP1293; WP1341-WP1352(T) | na |
| WORiA | wRi_012450-wRi_012680(T) | na | na |
| WORiB | wRi_005400-wRi_005660 | wRi_005310(T)-wRi_005390; wRi_005670-wRi_005720; wRi_005860-wRi_005930(T) | wRi_005730-wRi_005830 |
| WORiB(2) | wRi_010060-wRi_010320 | wRi_009980(T)-wRi_010050; wRi_010330-wRi_010380; wRi_010500-wRi_010580(T) | wRi_010390-wRi_010490 |
| WORiC | wRi_006880-wRi_007230(T); wRi_007550-wRi_007660(T) | wRi_006620-wRi_006870 | na |
| WOHa1 | wHa_02360-wHa_02620 | wHa_02010(T)-wHa_2050; wHa_02170-wHa_02350; wHa_02630-wHa_02760(T) | wHa_02060-wHa_02160 |
| WOHa2 | wHa_03390-wHa_03840 | wHa_03850-wHa_03930 | na |
| WONo1 | wNo_01400-wNo01060 | wNo_01000(T)-wNo_01050(T) | na |
| WONo2 | wNo_07170(T)-wNo_07380(T) | na | na |
| WONo3 | wNo_09000-wNo_09120 | wNo_09130-wNo_09150(T) | na |
| WONo4 | wNo_10070(T)-wNo_10280 | wNo_10290-wNo_10350 | na |
| wNo WO-Islands | na | wNo_01980-wNo_1990; wNo_2110-wNo_02200; wNo_05070-wNo_05150(T) | wNo_2000-wNo_2100 |

To verify the newly discovered EAM in the phage genome, the terminal phage WO genes were identified and amplicons were Sanger sequenced from an independent sample of phage WOVitA1 (FIG. 1a) across the circularized phage attP site (hypothetical protein gwv_1089 to recombinase, FIG. 7). Next, using the newly identified attR and attL sites, the bacterial attB site was extrapolated in WOVitA1, which is a noncoding, repetitive sequence in *Wolbachia* from *Nasonia* wasps (FIG. 7e and sequences below).

(SEQ ID NO: 3, attL,
GCAAATACAATAGCTTCACTGTTATGACGTCCAGTACAATGTTGCAA;

SEQ ID NO: 4, attR,
TTTTTGTAACATTGTTATACACATCATGATAAGGGGCTGGCGGAGTTT;

SEQ ID NO: 5, attP,
TTTTTGTAACATTGTTATACACATCATGACGTCCAGTACAATGTTGCAA;

SEQ ID NO: 6, attB,
GCAAATACAATAGCTTCACTGTTATGATAAGGGGCTGGCGGAGTTT).

The full length of the completely assembled circular WOVitA1 is 66,688 bp, which is 48% larger than any previous prophage WO annotation. Similarly, the new terminal ends of the WOCauB3 phage (23,099 bp (51%) larger than original estimate of 45,078 bp) along with internal localization of the EAM genes by Sanger sequencing its attP site [Domain of Unknown Function (DUF)2426 to recombinase] were also identified. While a complete contig for WOCauB2 was not assembled, it is more than 12,000 bp larger than the original estimate of 43,016, includes multiple ankyrin repeat genes homologous to those in WOVitA1, and, like many other phage haplotypes (e.g., WORiC, WOVitA2, WOSuziC), integrates directly into *Wolbachia*'s magnesium chelatase (chlI) gene.

Figure 2A:
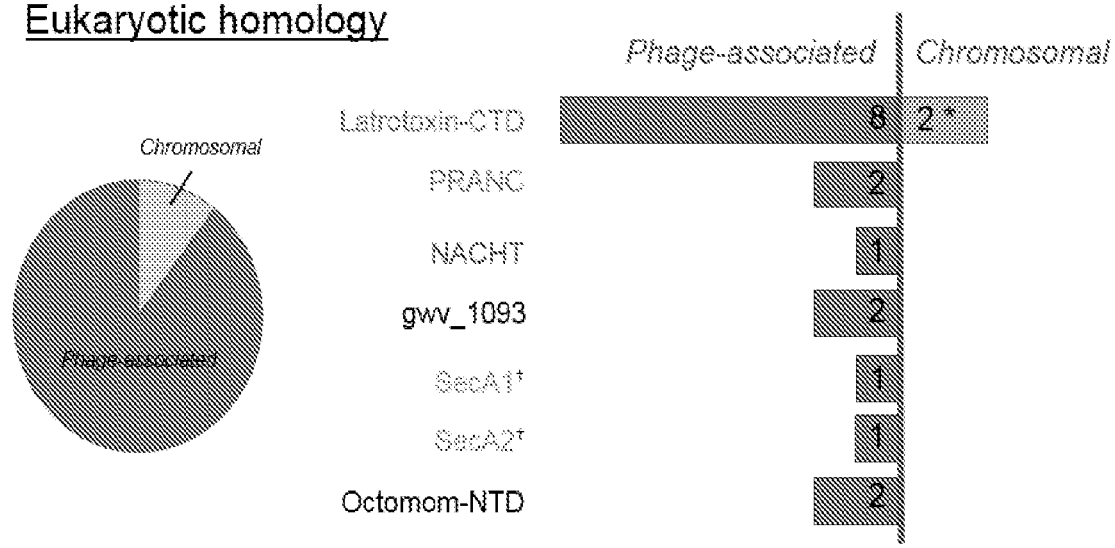
Figure 2B:
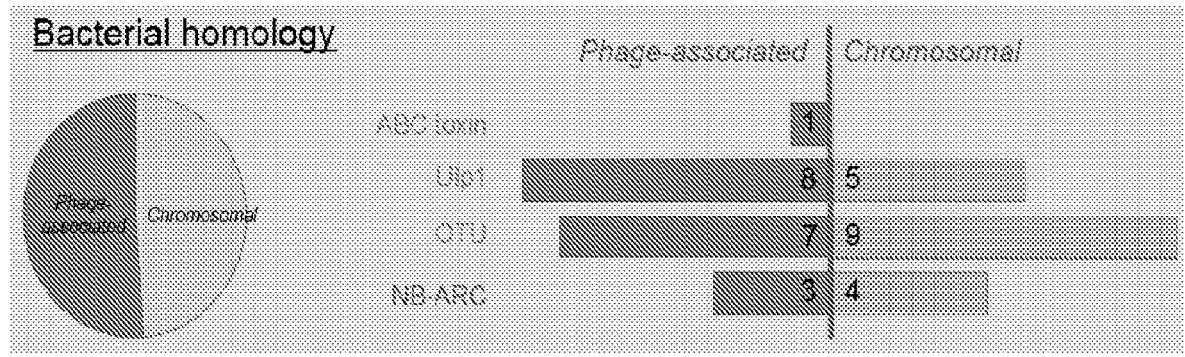

Next, each phage WO protein domain was analyzed for homology and surrounding peptide architecture. Unlike the single domain architecture of phage WO's structural genes, EAM genes are highly polymorphic and encompass fusions of both eukaryotic and bacterial protein domains. By extending the analysis to include homologous prophage regions from all sequenced *Wolbachia* chromosomes, ten types of protein domains with putative eukaryotic functions were revealed spanning four predicted functions: (i) toxins, (ii) host-microbe interactions, (iii) host cell suicide, and (iv) secretion of proteins through the cell membrane (FIG. 2). Notably, over half of these domain types (6/10; latrotoxin-CTD, PRANC, NACHT, SecA, gwv_1093-NTD, Octomom-NTD) share greater amino acid homology to eukaryotic invertebrates than to bacteria in GenBank. Among this subset with eukaryotic sequence homology, the protein domains are almost exclusively found in the EAM region (N=17) versus the *Wolbachia* chromosome (N=2). This pattern differs from other EAM protein domains with bacterial homology, which are equally dispersed in phage WO (N=19) and the *Wolbachia* chromosome (N=18) (FIG. 2, Fisher's Exact Test, p=0.0072). This difference importantly indicates that the eukaryotic-like protein domains are highly enriched in the EAM, suggesting a near exclusive role in phage WO biology.

Figure 3A:
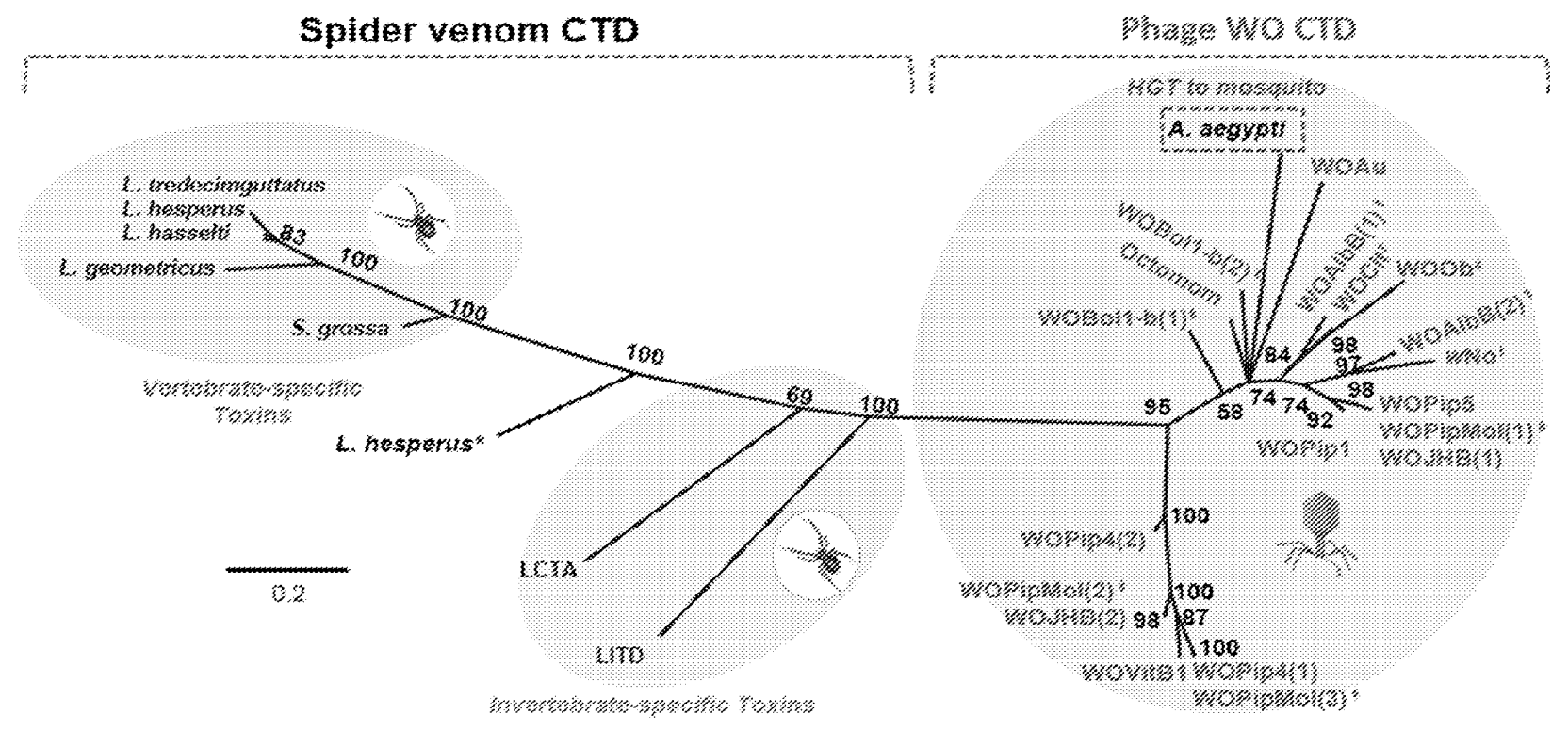
Figures 3B, 3C, 3D:
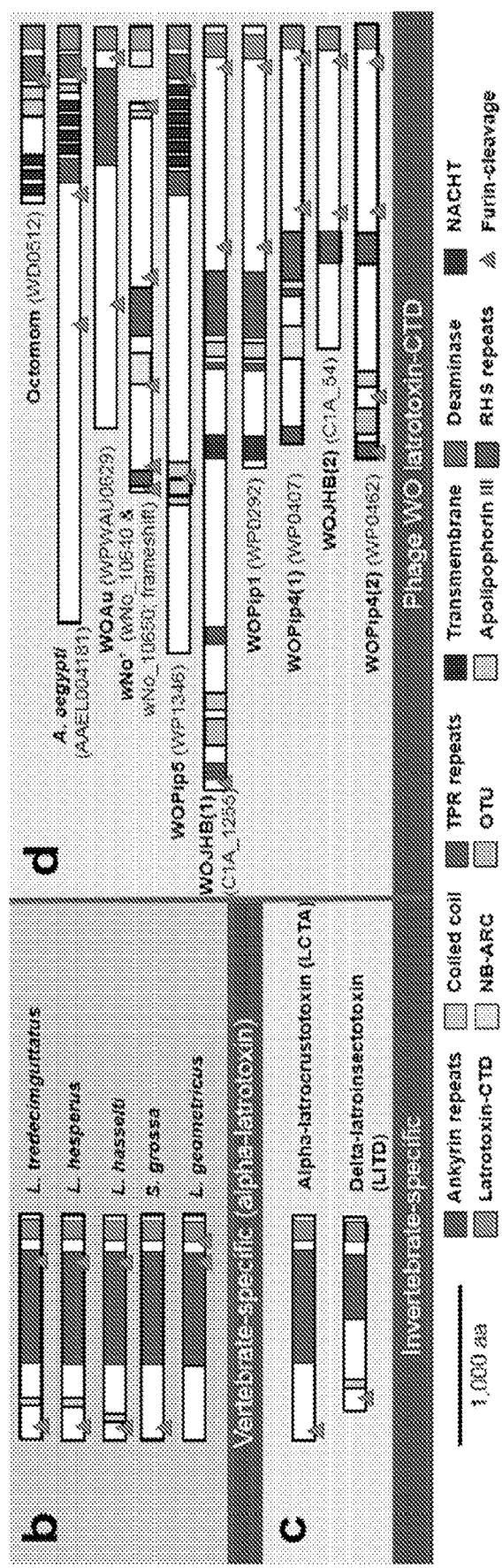

Latrotoxin C-terminal domain (CTD) is the most prevalent eukaryotic domain in phage WO. Originally described for its major role in the venom of widow spiders (*Latrodectus* species), latrotoxins cause the formation of membrane pores in their vertebrate or invertebrate victims. Phylogenetic analysis indicates that the latrotoxin-CTD horizontally transferred between widow spiders and phage WO (FIG. 3). In addition, reciprocal search queries using homologous spider and phage CTDs return the same BLASTp hits shown in FIG. 3. These taxa occur in overlapping ecological niches (*Wolbachia* are known to infect spiders of the family Theridiidae) in which gene transfers are more likely to happen (Goodacre, S. L., et al. *Mol Ecol* 15, 517-27 (2006); Vanthournout, B., et al. *BMC Evol Biol* 11, 15 (2011)). The presence of *Wolbachia* in three independent *Latrodectus geometricus* samples was confirmed by amplifying *Wolbachia* 16S rDNA and wsp membrane protein genes. The transfer event was apparently followed by a relatively more recent transfer from phage WO back to animals in the *Aedes aegypti* genome where the region is located between genes of mosquito origin [fibrinogen-related protein (AAEL004156) and GalE3 (AAEL004196)], or *A. aegypti* was the putative donor of the domain to phage WO, followed by a recursive transfer to black widow spiders.

Latrotoxin-CTD is universally located at the 3'-terminal ends of both conserved spider latrotoxin genes (Garb, J. E. & Hayashi, C. Y. *Mol Biol Evol* 30, 999-1014 (2013)) and enormous, polymorphic, and eukaryotic-like phage WO genes (up to 14,256 bp). Notably, phage WO CTD sequences have the highest amino acid similarity to black widow spider homologs that target invertebrates, which are the primary hosts of *Wolbachia*. There is also a high incidence of eukaryotic furin cleavage sites that immediately precede the latrotoxin-CTD. In spiders, cleavage at these sites by the eukaryotic furin protease in the trans-Golgi network or extracellular matrix is required for latrotoxin activation before the toxin exerts its effects upon the victim (Gordon, V. M. & Leppla, S. H. *Infect Immun* 62, 333-40 (1994); Remacle, A. G. et al. *Int J Biochem Cell Biol* 42, 987-95 (2010); Tsuneoka, M. et al. *J Biol Chem* 268, 26461-5 (1993)). All phage WO EAMs contain at least one site for eukaryotic furin cleavage (Table 2), and the proportion of all EAM genes with predicted furin cleavage sites (25%) is two-fold greater than that of the genes in the core phage genome (11%, Fisher's Exact Test, p<0.0001), defined as the conserved bacteriophage region from recombinase to patatin. In regards to the phage WO latrotoxin-CTD, their packaging in virions, conservation of eukaryotic furin cleavage sites, large eukaryotic-like length, and reduced CTD divergence relative to the spider venom CTD is consistent with their eukaryotic origin and post-translational processing by furin peptidases.

TABLE 2

Phage WO EAM furin cleavage sites.

| GENOME | EAM FURIN CLEAVAGE |
|---|---|
| WOCauB2 | (partial sequence) |
| WOCauB3 | gp45, GF2gp18-GF2gp22 |
| WOSol | wSo0011, So0023, So0025 |
| WOMelA | WD0257-WD0258 |
| WOMelB | WD0610, WD0630-WD0632 |
| wMel WO-Island | WD0512-WD0514 |
| WOPip1 | WP0280, WP0283, WP0290, WP0292-WP0293 |
| WOPip2 | WP0294, WP0319-WP0320 |
| WOPip3 | WP0338 |
| WOPip4 | WP0407, WP0410, WP0428, WP0433, WP0457, WP0460, WP0462-WP0463 |
| WOPip5 | WP1291, WP1341, WP1344, WP1346, WP1349, WP1351 |
| WORiA | (haplotype does not have an EAM) |
| WORiB | wRi_005330, wRi_005360, wRi_005670, wRi_005720 |
| WORiB(2) | wRi_009990, wRi_010020, wRi_010330, wRi_010380, wRi_010570 |
| WORiC | wRi_006630-wRi_006660, wRi_006740 |
| WOVitA1 | gwv_1095 |
| WOVitA2 | gwv_464, gwv_484, gwv_489, gwv_491-gwv_495 |
| WOVitA4 | gwv_134, gwv_141-gwv_142, gwv_144-gwv_145 |
| WOHa1 | wHa_02170, wHa_02200, wHa_02290, wHa_02350, wHa_02690, wHa_02730 |
| WOHa2 | wHa_03920 |
| WONo1 | wNo_01030, wNo_01060 |
| WONo2 | (haplotype does not have an EAM) |
| WONo3 | wNo_09000, wNo_09080, wNo_09140 |
| WONo4 | wNo_10290, wNo_10320-wNo_10340 |
| wNo WO-Islands | wNo_01990, wNo_02030, wNo_02070, wNo_02120, wNo_02130, wNo_05080-wNo_05090, wNo_05110-wNo_05130 |

Table 2 lists genes with predicted furin cleavage sites, indicative of potential host-induced protein modification, were identified within every prophage WO EAM. NCBI accession numbers for the analyzed phage regions are: WOCauB2—AB478515; WOCauB3—AB478516; WOSol—KC955252; wMel—AE017196; wPip—AM999887; wRi—CP001391; wVitA—PRJDB1504; wHa—CP003884; wNo—CP003883.

Domains central to modifying animal proteins are also abundant in the phage EAM. The Pox protein Repeats of ANkyrin C terminus (PRANC) domain in the WOVitA1 genome (gwv_1092) shares protein sequence homology with corresponding PRANC domains in multiple parasitic wasp hosts (Table 3) and their eukaryotic viruses. Reciprocal BLASTp searches retrieve the same best hits and support previous findings that this protein domain horizontally transferred between eukaryotic viruses, animals, and Proteobacteria (Werren, J. H. et al. Science 327, 343-8 (2010)). The discovery here of the eukaryotic-like PRANC domain in phage WO parallels its presence in the Poxviridae virus family, in which it functions in evasion of eukaryotic immune responses via modification of host ubiquitination. PRANC is related to amino acid sequences in F-box proteins, which are eukaryotic proteins involved in protein degradation. The PRANC domain also occurs in vaccina virus, ectromelia virus, cowpox virus and Orf virus and can regulate NF-κB signalling pathway to inhibit transcription of inflammatory cytokines (Chang, S. J. et al. J Virol 83, 4140-52 (2009)).

Figures 4A, 4B, 4C:
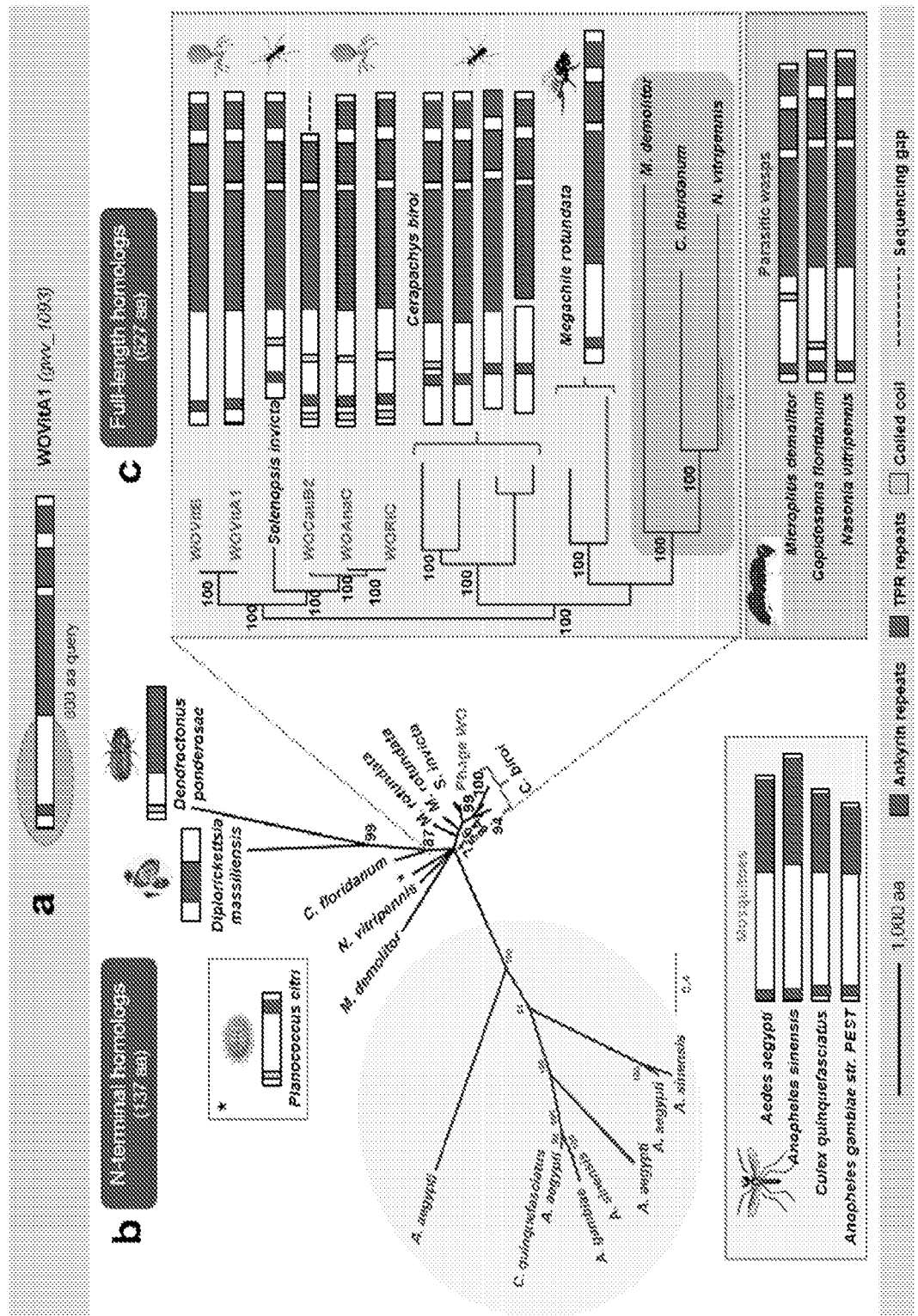

Phylogenetic analysis using reciprocal BLASTp hits (FIG. 4) shows that the N-terminus sequences of the TPR-containing gwv_1093 is embedded within, and likely derived by horizontal transfer from, a deeper and more diverse set of ancestral lineages in arthropods (FIG. 4b). The event was either followed by a relatively recent recursive transfer from phage WO back to animals in the Solenopsis invicta genome (FIG. 4c), where the gene is located between genes of ant origin (bicaudal D and rho guanine nucleotide exchange factor 11), or Solenopsis invicta is the putative donor of the region to phage WO.

Figures 5A, 5B, 5C:
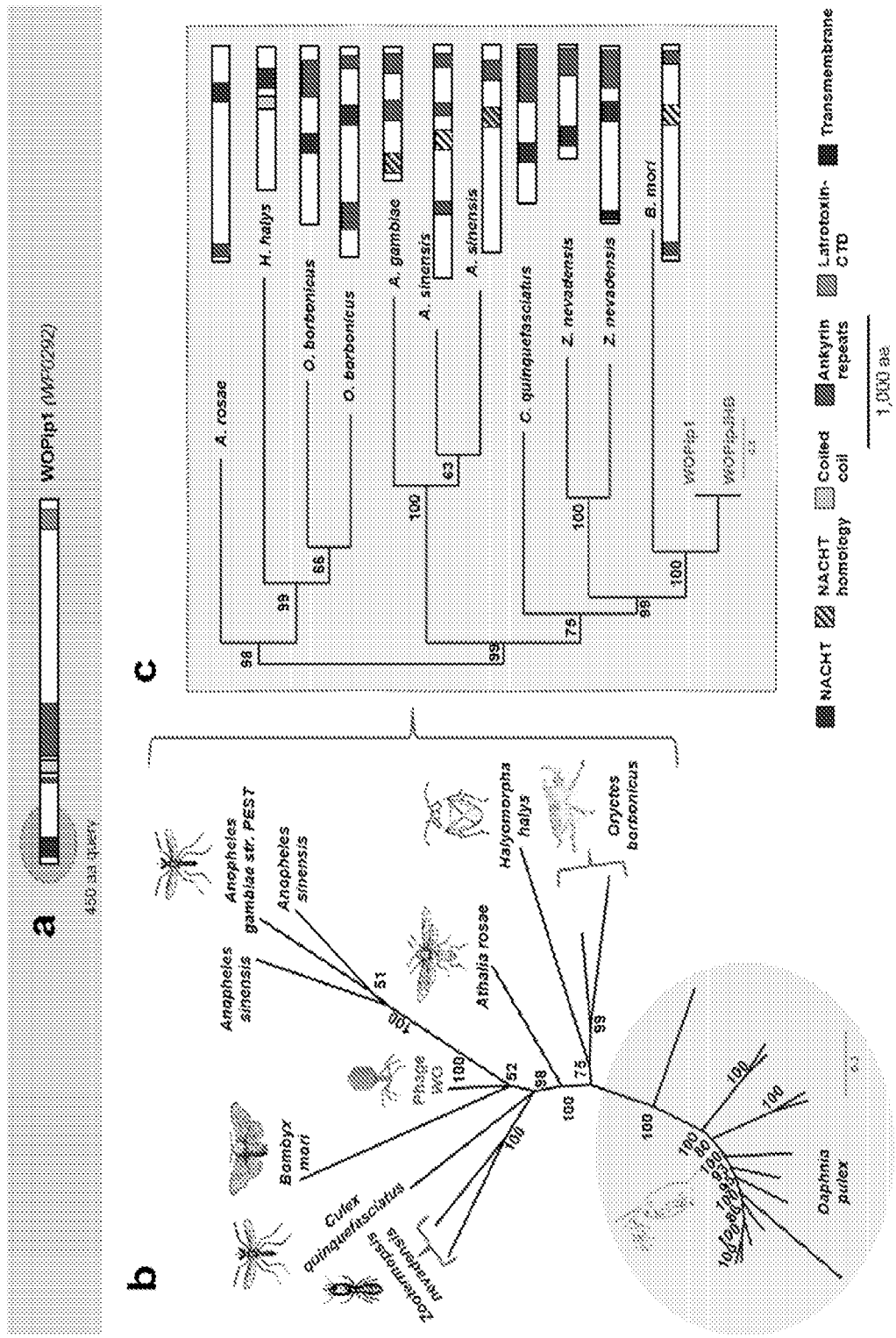

Another instance of genetic transfer between insects and bacteriophages involves the programmed cell death (PCD) domain, NACHT (FIG. 5). Eukaryotic NACHT-containing proteins are typically engaged in PCD by acting as pathogen-sensors and signal transduction molecules of the innate immune system (Koonin, E. V. & Aravind, L. Cell Death Differ 9, 394-404 (2002)). The polymorphic phage WO homolog encodes ankyrin repeats and a latrotoxin-CTD directly downstream from the conserved NTPase domain (FIG. 5a). NACHT domains have been identified in animals, fungi and bacteria (Koonin, E. V. & Aravind, L. Trends Biochem Sci 25, 223-4 (2000)) and phylogenetic patterns indicate multiple instances of horizontal transfer (Leipe, D. D., et al. J Mol Biol 343, 1-28 (2004)). A NACHT-containing peptide was recently discovered in the Clostridium difficile-infecting phage phiCDHM1 genome (Hargreaves, K. R., et al. PLoS One 9, e85131 (2014)) although, in contrast to phage WO, the phiCDHM1 NACHT domain is bacterial in

TABLE 3

The phage WO PRANC domain shares amino acid homology with multiple eukaryotic host peptides.

| EUKARYOTIC HOMOLOG | ACCESSION | E-VALUE | QUERY COVERAGE | IDENTITY |
|---|---|---|---|---|
| Microplitis demolitor | XP_014298115.1 | 8.00E−43 | 75% | 49% |
| Nasonia vitripennis | XP_003426146.1 | 5.00E−23 | 76% | 37% |
| Glypta fumiferanae | AKD28025.1 | 4.00E−21 | 71% | 39% |
| Trichogramma pretiosum | XP_014232168.1 | 2.00E−16 | 73% | 33% |
| Ceratosolen solmsi marchali | XP_011505281.1 | 8.00E−15 | 69% | 31% |
| Copidosoma floridanum | XP 014206311.1 | 3.00E−12 | 58% | 32% |
| Diaphorina citri | XP_008470724.1 | 9.00E−10 | 49% | 31% |

Table 3 shows that the PRANC domain in WOVitA1's gwv_1092 shares homology with multiple insect hosts. The best BLASTp hit for each species is listed above with E-value, query coverage and identity.

Adjacent to the PRANC-encoding gene in WOVitA1 is an ankyrin and tetratricopeptide repeat (TPR)-containing gwv_1093. Ankyrin repeats and TPRs mediate a broad range of protein-protein interactions (apoptosis, cell signaling, inflammatory response, etc.) within eukaryotic cells and are commonly associated with effector proteins of certain intracellular pathogens (Cerveny, L. et al. Infect Immun 81, 629-35 (2013); Jernigan, K. K. & Bordenstein, S. R. Peer J 2, e264 (2014); Jernigan, K. K. & Bordenstein, S. R. Peer J 3, e732 (2015); Li, J., Mahajan, A. & Tsai, M. D. Biochemistry 45, 15168-78 (2006); Pan, X., et al. Science 320, 165 1-4 (2008)). While generally rare in viral genomes (FIGS. 8 and 9, respectively), they occur in all phage WO haplotypes from sequenced Wolbachia genomes (N=23).

both amino acid homology and protein architecture. Similar to the phylogeny of the N-terminus of the TPR-containing gwv_1093, the NACHT domain sequence in phage WO is embedded within, and likely derived by horizontal transfer from, a deeper and more diverse set of ancestral variants in arthropods (FIG. 5b,c).

This inaugural set of completely sequenced phage WO particle genomes, coupled with reciprocal BLAST analyses, phylogenies, annotations of the conserved domains, evolutionary distances, gene lengths, and enrichment of eukaryotic furin cleavage sites in the phage EAM, reveals evidence for lateral genetic transfers from metazoans to bacteriophage. The presence of eukaryotic protein domains in bacteriophage genomes is of special note as they curiously mirror eukaryotic genes in large eukaryotic viruses that aid in viral mimicry and manipulation of host processes (Alcami, A. & Koszinowski, U. H. Immunol Today 21, 447-55 (2000); Piekna-Przybylska, D., et al. Nat Struct Mol Biol 17, 83-9 (2010); Seet, B. T. et al. *Annu Rev Immunol* 21, 377-423 (2003)). Similarly in phage WO, these animal protein domains are central to anti-eukaryotic functions including the black widow latrotoxin, programmed cell death (NACHT), immune evasion (PRANC), and protein-protein interactions. They have never before been reported in bacteriophage genomes because phages have naturally been overlooked as recipients of eukaryotic DNA.

Bacteriophage WO frequently transfer between *Wolbachia* coinfections in the same animal host (Bordenstein, S. R. & Wernegreen, J. J. *Mol Biol Evol* 21, 1981-91 (2004); Masui, S., et al. J Mol Evol 51, 491-7 (2000)) and to the host genome as part of large transfers of the *Wolbachia* chromosome (Dunning Hotopp, J. C. et al. *Science* 317, 1753-6 (2007); Funkhouser-Jones, L. J. et al. *Peer J* 3, e1479 (2015)). It was previously reported that they were also capable of transferring adjacent flanking non-phage genes in the process of transfer between coinfections (Kent, B. N. et al. *Genome Biol Evol* 3, 209-18 (2011)). For two of these flanking genes, sequence evidence indicated that *Wolbachia* genomes may be able to receive eukaryotic DNA (Duplouy, A. et al. *BMC Genomics* 14, 20 (2013); Klasson, L., et al. BMC Genomics 10, 33 (2009); Woolfit, M., et al. *Mol Biol Evol* 26, 367-74 (2009)). However, the nature of these lateral genetic transfers remained to be validated and elucidated as these regions were not previously known to be part of the packaged phage genome until now. Based on this work, systematic surveys of phage genomes in intimate host-associated bacteria may uncover a broad range of eukaryotic protein domains involved in phage lifecycle adaptations and phage-eukaryote interactions.

Figures 6A, 6B, 6C, 6D:
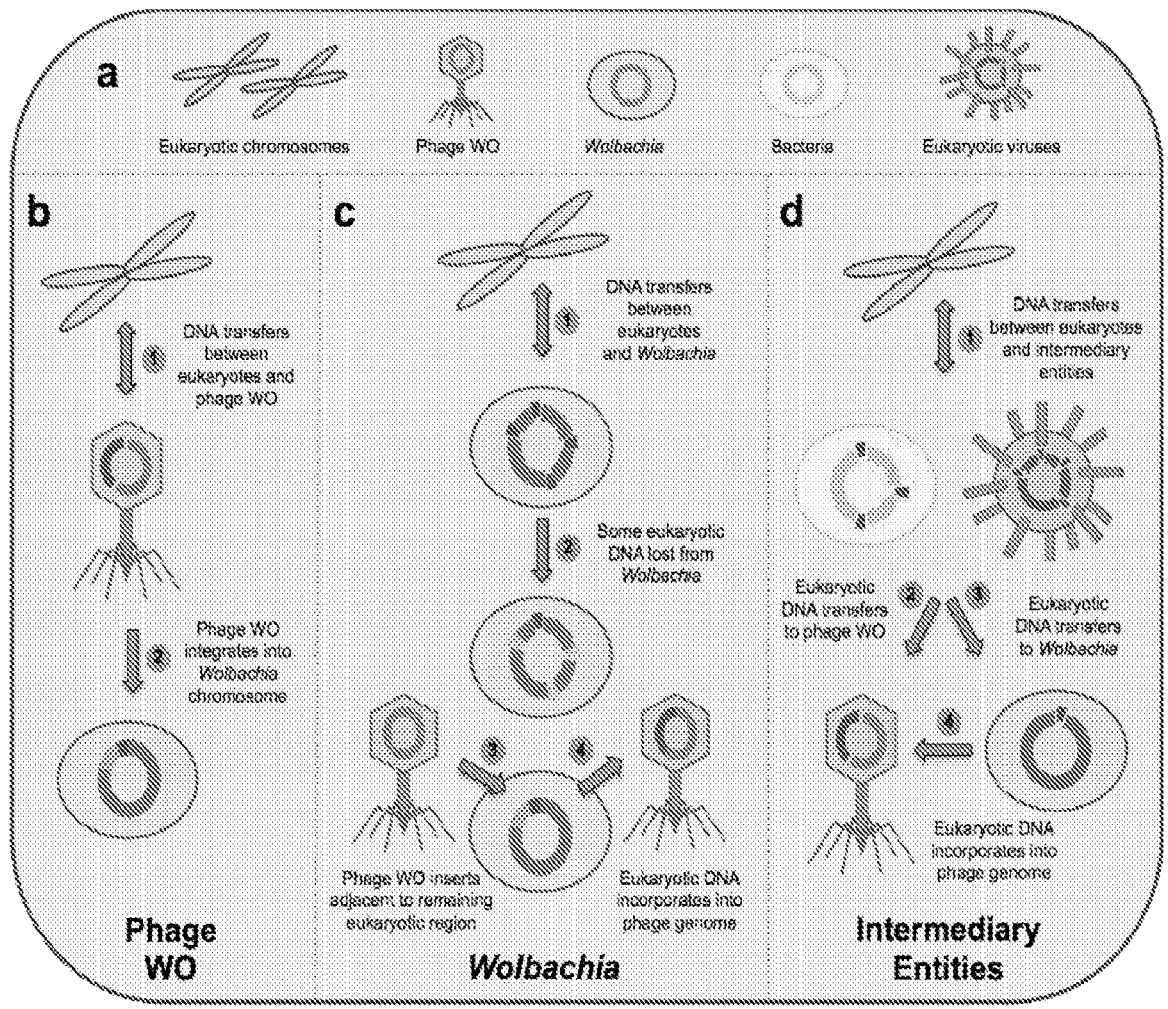

The mechanisms by which eukaryotic protein domains integrate into phage WO are unknown, and could follow at least two models. First, animal genetic material could directly transfer to WO genomes during phage particle packaging in the cytoplasm of animal cells (FIG. 6a) or inside *Wolbachia* cells that are lysing and exposed to the eukaryotic cytoplasmic environment. Packaging of eukaryotic host RNAs, for instance, occur in the virions of herpesvirus (Amen, M. A. & Griffiths, A. *J Virol* 85, 7296-311 (2011); Amen, M. A. & Griffiths, A. *Front Genet* 2, 81 (2011)) and cytomegalovirus (Terhune, S. S., et al. *J Virol* 78, 10390-8 (2004)). Second, genes may transfer from animal genomes to the *Wolbachia* chromosome and then to prophage WO. However, for this scenario to be plausible, animal genetic material transferred presumably in random locations in the *Wolbachia* genome would have to be preferentially lost in non-phage associated domains from the *Wolbachia* chromosome (FIG. 6b) because domains with eukaryotic homology are extremely enriched in the phage/prophage WO EAM versus the rest of the chromosome (FIG. 2).

Why are these protein domains present in the EAM of bacteriophage WO? Phages of obligate intracellular bacteria are contained within both bacterial and eukaryotic membranes and can possess an enigmatic "two-fold cell challenge". They may not only have to breach peptidoglycan and permeabilize bacterial membranes, but they may also have to exit (and enter) across the eukaryotic membrane(s) that directly encapsulates the bacteria. Functional studies of homologous domains (i.e., PRANC and NACHT) suggest that these proteins could have eukaryotic viral-like properties that are deployed in processes such as the lysis of eukaryotic cells and post-translational modification of host proteins (Bergsbaken, T., et al. *Nat Rev Microbiol* 7, 99-109 (2009); Zhang, L., et al. *FEBS Lett* 583, 607-14 (2009)). Phage WO can dwell in the eukaryotic cytoplasm and extracellular matrix that they encounter upon bacterial lysis (Bordenstein, S. R., et al. *PLoS Pathog* 2, e43 (2006)), raising the possibility of direct interaction with the host's biology.

Chlamydiomicroviridae infect obligate intracellular bacteria, yet still do not directly contend with the eukaryotic membrane. Rather, they attach to dormant chlamydial cells (i.e., reticulate bodies) and enter via phagocytosis or endocytosis of the bacteria (Sliwa-Dominiak, J., et al. *Arch Microbiol* 195, 765-71 (2013)). The phages then alter development of their bacterial host, which leads to disintegration of the chlamydial inclusion and subsequent lysis of the eukaryotic host cell (Hsia, R., et al. *Microbes Infect* 2, 761-72 (2000); Salim, O., et al. *Virology* 377, 440-5 (2008)). The nature of phage WO's lifestyle, on the other hand, may require a distinct interaction with multiple membranes and immune responses because lytic activity of phage WO has been associated with typical bacterial cell defects including degraded bacterial DNA, a detached inner membrane, and exit of the phage particles from inside *Wolbachia* and its host cell into the extracellular matrix of the reproductive tissues (Bordenstein, S. R., et al. *PLoS Pathog* 2, e43 (2006)). Bacteriophages of free-living bacteria also regularly colonize eukaryotic environments, particularly those associated with mucosal surfaces (Barr, J. J. et al. *Proc Natl Acad Sci USA* 110, 10771-6 (2013)). They, however, do not infect or traverse the eukaryotic membrane and are still within the genomic boundaries of the bacterial virosphere.

Temperate dsDNA phages also occur in facultative symbionts of aphids (Moran, N. A., et al. *Proc Natl Acad Sci USA* 102, 16919-26 (2005)) and tsetse flies (Belda, E., et al. *BMC Genomics* 11, 449 (2010)). While *Wolbachia* has never successfully been cultured outside of host cells (Rasgon, J. L., et al. *Appl Environ Microbiol* 72, 6934-7 (2006)), these facultative symbionts can replicate both intra- and extracellularly (J W Brandt, personal communication, July 2015; (Weiss, B. L., et al. *Proc Natl Acad Sci USA* 105, 15088-93 (2008))) suggesting that their phages are not constrained by the same two-fold cell challenge. In addition, their phages encode a traditional lytic cassette (holin and lysozyme) that correlates with the need to deal only with bacterial membranes. In some cases, the phages harbor bacterial-derived toxins that target eukaryotic cells (Degnan, P. H. & Moran, N. A. *Appl Environ Microbiol* 74, 6782-91 (2008)), and these function mutualistically in aphids by arresting parasitoid wasp larvae (Moran, N. A., et al. *Proc Natl Acad Sci USA* 102, 16919-26 (2005)). Furthermore, unlike phage WO, these phages are readily lost in the absence of parasitoids during laboratory rearing, presumably due to the cost of their toxins (Oliver, K. M., et al. *Science* 325, 992-4 (2009)).

In addition to providing new insights into the evolution of bacteriophages and showing phage WO to be far more complex than previously described, the findings here reveal that phage evolution in *Wolbachia* leads to a novel example of phage-metazoan genomic chimerism. Acquisition and retooling of intact eukaryotic domains in phage WO appears to be analagous to the commandeering of host genes by eukaryotic viruses. Whether this newly discovered highway of lateral genetic transfer is common in the symbiotic virosphere remains to be determined.

Methods

Insect and Bacterial Strains

The transfected line of the Mediterranean flour moth *Ephestia kuehniella* harboring *Wolbachia* strain wCauB was obtained from Takema Fukatsu and Tetsuhiko Sasaki (Fujii, Y., et al. *Biochem Biophys Res Commun* 317, 1183-8

(2004)). Moths were maintained at 24° C. and 70% humidity on a diet consisting of wheat bran, glycerol and dried yeast (20:2:1 w/w). The introgressed line of the parasitoid wasp *Nasonia giraulti* harboring *Wolbachia* strain wVitA, termed IntG12.1, was previously derived by repeatedly backcrossing *N. vitripennis* (strain 12.1) females to *N. giraulti* males for nine generations (Chafee, M. E. et al. *Genetics* 187, 203-15 (2011)). The strain was incubated at 25° C. using the flesh fly *Sarcophaga bullata* as host.

Phage Particle Purification

Phage particles were isolated according to Fujii et al (Fujii, Y., et al. *Biochem Biophys Res Commun* 317, 1183-8 (2004)) with modifications. Approximately 4 g of adult insects were homogenized in 29.6 ml cold SM buffer (50 mM Tris-HCl, pH 7.5, 0.1 M NaCl, 10 mM $MgSO_4$ $7H_2O$, and 0.1% (w/v) gelatin). NaCl and RNase A were added to a final concentration of 1M and 1 ug/ml, respectively. The homogenate was incubated on a shaker at 4° C. for 1 h and then centrifuged at 13,000 g for 10 min at 4° C. Polyethylene glycol (PEG) 6000 was added to a final concentration of 10% to precipitate phage particles, incubated at 4° C. for 1 hr with gentle shaking and centrifuged at 13,000 g for 10 min. The pellet was resuspended in 5 ml TM buffer (50 mM Tris-HCl, pH 7.5, 10 mM $MgCl_2.6H_2O$) and mixed with an equal volume chloroform. The suspension was centrifuged at 3,000 g to remove PEG and the aqueous phase was filtered through a 0.22 um filter to remove bacterial cells. The suspension was centrifuged at 60,000 g for 1 h at 4 C to collect phage particles. The pellet was suspended in 10 ul TM buffer.

Phage DNA Extraction & Metagenomic Sequencing

The phage suspension was treated with RQ1 RNase-Free DNase (Promega) for 30 min at 37° C., followed by heat inactivation for 10 min at 65° C., to remove host DNA contamination. Phage DNA was extracted from the suspension using the QIAamp MinElute Virus Spin Kit (Qiagen) and amplified using the REPLI-g Mini Kit (Qiagen). Following amplification, paired-end DNA libraries were prepared according to manufacturer's (Illumina) instructions and samples were sequenced with an Illumina HiSeq 2000 (2×100-nt read length).

Bioinformatics & Statistics

Metagenomic sequences (reads) were trimmed, paired and assembled into contigs using the CLC Assembler (CLC bio) with bubble size=50, insertion and deletion cost=3, mismatch cost=2, length fraction=0.6, minimum contig size=130, similarity=0.5, minimum distance=90 and maximum distance=200. Contigs were compared to the GenBank non-redundant database using NCBI's BLASTN (blast.ncbi.nlm.nih.gov/Blast.cgi) and those with similarity to phage WO and/or *Wolbachia* (E-value $<10^{-10}$) were manually annotated using Geneious (Biomatters Ltd.). Individual reads were mapped to reference sequences using Geneious. Open reading frame (ORF) homology searches were performed to determine putative function using NCBI's BLASTP (blast.ncbi.nlm.nih.gov/Blast.cgi) and Wellcome Trust Sanger Institute's pfam database (pfam.sanger.ac.uk). Coiled coil domains were predicted with EMBL's Simple Modular Architecture Research Tool (SMART, smart.embl-heidelberg.de). Furin cleavage sites were identified using PiTou (nuolan.net/reference.html). The number of genes with and without furin cleavage sites was analyzed with respect to phage-region using Fisher's Exact Test (GraphPad Software). Phylogenetic trees were built using the Bayes plugin in Geneious and model selection for each Bayes analysis was estimated using ProtTest (Abascal, F., et al. *Bioinformatics* 21, 2104-5 (2005)).

Confirmation of Phage WO Terminal Genes

Genomic DNA was extracted from wVitA-infected *N. vitripennis* (strain 12.1) and wCauB-infected *E. kuehniella* individuals using the Gentra Puregene Tissue Kit (Qiagen). Primers were designed for both WOVitA1 and WOCauB3 att sites, respectively: VitA1_attF (5'-CGA AGA ACC AGC ACA GGG TGG-3':SEQ ID NO:15), VitA1_attR (5'-GCT GGA AGA GGG CAT CTG CAT C-3':SEQ ID NO:16), CauB3_attF (5'-TCG TGA CTG CCC TAT TGC TGC T-3':SEQ ID NO:17) and CauB3_attR (5'-ATG CGG CCA AAG CTG GGT GT-3':SEQ ID NO: 18). Amplification was performed in a Veriti thermal cycler (Applied Biosystems) using GoTaq green master mix (Promega) under the following conditions: 94 C for 2 min; 35 cycles of 94 C for 30 s, 53 C for 30 s, 72 C for 1 min; and a final elongation cycle of 72 C for 10 min. PCR products were sequenced via Sanger sequencing (Genewiz, Inc).

REFERENCES

1. Edwards, R. A. & Rohwer, F. Viral metagenomics. *Nat Rev Microbiol* 3, 504-10 (2005).
2. Hendrix, R. W., Smith, M. C., Burns, R. N., Ford, M. E. & Hatfull, G. F. Evolutionary relationships among diverse bacteriophages and prophages: all the world's a phage. *Proc Natl Acad Sci USA* 96, 2192-7 (1999).
3. Suttle, C. A. Viruses in the sea. *Nature* 437, 356-61 (2005).
4. Brussow, H. The not so universal tree of life or the place of viruses in the living world. *Philos Trans R Soc Lond B Biol Sci* 364, 2263-74 (2009).
5. King, A. M. Q., Adams, M. J., Lefkowitz, E. J. & Carstens, E. B. *Virus taxonomy: classification and nomenclature of viruses: Ninth Report of the International Committee on Taxonomy of Viruses.*, 1327 (Elsevier, San Diego, 2012).
6. Nasir, A., Forterre, P., Kim, K. M. & Caetano-Anolles, G. The distribution and impact of viral lineages in domains of life. *Front Microbiol* 5, 194 (2014).
7. Prangishvili, D., Forterre, P. & Garrett, R. A. Viruses of the Archaea: a unifying view. *Nat Rev Microbiol* 4, 837-48 (2006).
8. Forterre, P. Giant viruses: conflicts in revisiting the virus concept. *Intervirology* 53, 362-78 (2010).
9. Raoult, D. TRUC or the need for a new microbial classification. *Intervirology* 56, 349-53 (2013).
10. Nasir, A. & Caetano-Anolles, G. A phylogenomic data-driven exploration of viral origins and evolution. *Science Advances* 1(2015).
11. Elde, N. C. & Malik, H. S. The evolutionary conundrum of pathogen mimicry. *Nat Rev Microbiol* 7, 787-97 (2009).
12. Rappoport, N. & Linial, M. Viral proteins acquired from a host converge to simplified domain architectures. *PLoS Comput Biol* 8, e1002364 (2012).
13. Colson, P. & Raoult, D. Gene repertoire of amoeba-associated giant viruses. *Intervirology* 53, 330-43 (2010).
14. Canchaya, C., Fournous, G. & Brussow, H. The impact of prophages on bacterial chromosomes. *Mol Microbiol* 53, 9-18 (2004).
15. Lindell, D. et al. Transfer of photosynthesis genes to and from Prochlorococcus viruses. *Proc Natl Acad Sci USA* 101, 11013-8 (2004).
16. Dammeyer, T., Bagby, S. C., Sullivan, M. B., Chisholm, S. W. & Frankenberg-Dinkel, N. Efficient phage-mediated pigment biosynthesis in oceanic cyanobacteria. *Curr Biol* 18, 442-8 (2008).

17. Werren, J. H., Baldo, L. & Clark, M. E. *Wolbachia*: master manipulators of invertebrate biology. *Nat Rev Microbiol* 6, 741-51 (2008).
18. Zug, R. & Hammerstein, P. Still a host of hosts for *Wolbachia*: analysis of recent data suggests that 40% of terrestrial arthropod species are infected. *PLoS One* 7, e38544 (2012).
19. Cho, K. O., Kim, G. W. & Lee, O. K. *Wolbachia* bacteria reside in host Golgi-related vesicles whose position is regulated by polarity proteins. *PLoS One* 6, e22703 (2011).
20. Henrichfreise, B. et al. Functional conservation of the lipid II biosynthesis pathway in the cell wall-less bacteria *Chlamydia* and *Wolbachia*: why is lipid II needed? *Mol Microbiol* 73, 913-23 (2009).
21. Louis, C. & Nigro, L. Ultrastructual evidence of *Wolbachia* Rickettsiales in *Drosophila simulans* and their relationships with unidirectional cross-incompatibility. *Journal of Invertebrate Pathology* 54, 39-44 (1989).
22. Gavotte, L. et al. A Survey of the bacteriophage WO in the endosymbiotic bacteria *Wolbachia*. *Mol Biol* Evol 24, 427-35 (2007).
23. Kent, B. N. & Bordenstein, S. R. Phage WO of *Wolbachia*: lambda of the endosymbiont world. *Trends Microbiol* 18, 173-81 (2010).
24. Metcalf, J. A. & Bordenstein, S. R. The complexity of virus systems: the case of endosymbionts. *Curr Opin Microbiol* 15, 546-52 (2012).
25. Chauvatcharin, N., Ahantarig, A., Baimai, V. & Kittayapong, P. Bacteriophage WO-B and *Wolbachia* in natural mosquito hosts: infection incidence, transmission mode and relative density. *Mol Ecol* 15, 2451-61 (2006).
26. Fujii, Y., Kubo, T., Ishikawa, H. & Sasaki, T. Isolation and characterization of the bacteriophage WO from *Wolbachia*, an arthropod endosymbiont. *Biochem Biophys Res Commun* 317, 1183-8 (2004).
27. Masui, S. et al. Bacteriophage WO and virus-like particles in *Wolbachia*, an endosymbiont of arthropods. *Biochem Biophys Res Commun* 283, 1099-104 (2001).
28. Sanogo, Y. O. & Dobson, S. L. WO bacteriophage transcription in *Wolbachia*-infected *Culex pipiens*. *Insect Biochem Mol Biol* 36, 80-5 (2006).
29. Tanaka, K., Furukawa, S., Nikoh, N., Sasaki, T. & Fukatsu, T. Complete WO phage sequences reveal their dynamic evolutionary trajectories and putative functional elements required for integration into the *Wolbachia* genome. *Appl Environ Microbiol* 75, 5676-86 (2009).
30. Wright, J. D., Sjostrand, F. S., Portaro, J. K. & Barr, A. R. The ultrastructure of the *rickettsia*-like microorganism *Wolbachia pipientis* and associated virus-like bodies in the mosquito *Culex pipiens*. *J Ultrastruct Res* 63, 79-85 (1978).
31. Bordenstein, S. R., Marshall, M. L., Fry, A. J., Kim, U. & Wernegreen, J. J. The tripartite associations between bacteriophage, *Wolbachia*, and arthropods. *PLoS Pathog* 2, e43 (2006).
32. Kent, B. N., Funkhouser, L. J., Setia, S. & Bordenstein, S. R. Evolutionary genomics of a temperate bacteriophage in an obligate intracellular bacteria (*Wolbachia*). *PLoS One* 6, e24984 (2011).
33. Hosokawa, T., Koga, R., Kikuchi, Y., Meng, X. Y. & Fukatsu, T. *Wolbachia* as a bacteriocyte-associated nutritional mutualist. *Proc Natl Acad Sci USA* 107, 769-74 (2010).
34. Darby, A. C. et al. Analysis of gene expression from the *Wolbachia* genome of a filarial nematode supports both metabolic and defensive roles within the symbiosis. *Genome Res* 22, 2467-77 (2012).
35. Foster, J. et al. The *Wolbachia* genome of *Brugia malayi*: endosymbiont evolution within a human pathogenic nematode. *PLoS Biol* 3, e121 (2005).
36. Goodacre, S. L., Martin, O. Y., Thomas, C. F. & Hewitt, G. M. *Wolbachia* and other endosymbiont infections in spiders. *Mol Ecol* 15, 517-27 (2006).
37. Vanthournout, B., Swaegers, J. & Hendrickx, F. Spiders do not escape reproductive manipulations by *Wolbachia*. *BMC Evol Biol* 11, 15 (2011).
38. Garb, J. E. & Hayashi, C. Y. Molecular evolution of alpha-latrotoxin, the exceptionally potent vertebrate neurotoxin in black widow spider venom. *Mol Biol* Evol 30, 999-1014 (2013).
39. Gordon, V. M. & Leppla, S. H. Proteolytic activation of bacterial toxins: role of bacterial and host cell proteases. *Infect Immun* 62, 333-40 (1994).
40. Remacle, A. G. et al. Selective and potent furin inhibitors protect cells from anthrax without significant toxicity. *Int J Biochem Cell Biol* 42, 987-95 (2010).
41. Tsuneoka, M. et al. Evidence for involvement of furin in cleavage and activation of diphtheria toxin. *J Biol Chem* 268, 26461-5 (1993).
42. Werren, J. H. et al. Functional and evolutionary insights from the genomes of three parasitoid *Nasonia* species. *Science* 327, 343-8 (2010).
43. Chang, S. J. et al. Poxvirus host range protein CP77 contains an F-box-like domain that is necessary to suppress NF-kappaB activation by tumor necrosis factor alpha but is independent of its host range function. *J Virol* 83, 4140-52 (2009).
44. Cerveny, L. et al. Tetratricopeptide repeat motifs in the world of bacterial pathogens: role in virulence mechanisms. *Infect Immun* 81, 629-35 (2013).
45. Jernigan, K. K. & Bordenstein, S. R. Ankyrin domains across the Tree of Life. *Peer J* 2, e264 (2014).
46. Jernigan, K. K. & Bordenstein, S. R. Tandem-repeat protein domains across the tree of life. *Peer J* 3, e732 (2015).
47. Li, J., Mahajan, A. & Tsai, M. D. Ankyrin repeat: a unique motif mediating protein-protein interactions. *Biochemistry* 45, 15168-78 (2006).
48. Pan, X., Luhrmann, A., Satoh, A., Laskowski-Arce, M. A. & Roy, C. R. Ankyrin repeat proteins comprise a diverse family of bacterial type IV effectors. *Science* 320, 1651-4 (2008).
49. Koonin, E. V. & Aravind, L. Origin and evolution of eukaryotic apoptosis: the bacterial connection. *Cell Death Differ* 9, 394-404 (2002).
50. Koonin, E. V. & Aravind, L. The NACHT family—a new group of predicted NTPases implicated in apoptosis and MHC transcription activation. *Trends Biochem Sci* 25, 223-4 (2000).
51. Leipe, D. D., Koonin, E. V. & Aravind, L. STAND, a class of P-loop NTPases including animal and plant regulators of programmed cell death: multiple, complex domain architectures, unusual phyletic patterns, and evolution by horizontal gene transfer. *J Mol Biol* 343, 1-28 (2004).
52. Hargreaves, K. R., Kropinski, A. M. & Clokie, M. R. What does the talking?: quorum sensing signalling genes discovered in a bacteriophage genome. *PLoS One* 9, e85131 (2014).
53. Alcami, A. & Koszinowski, U. H. Viral mechanisms of immune evasion. *Immunol Today* 21, 447-55 (2000).

54. Piekna-Przybylska, D., DiChiacchio, L., Mathews, D. H. & Bambara, R. A. A sequence similar to tRNA 3 Lys gene is embedded in HIV-1 U3-R and promotes minus-strand transfer. *Nat Struct Mol Biol* 17, 83-9 (2010).
55. Seet, B. T. et al. Poxviruses and immune evasion. *Annu Rev Immunol* 21, 377-423 (2003).
56. Bordenstein, S. R. & Wernegreen, J. J. Bacteriophage flux in endosymbionts (*Wolbachia*): infection frequency, lateral transfer, and recombination rates. *Mol Biol Evol* 21, 1981-91 (2004).
57. Masui, S., Kamoda, S., Sasaki, T. & Ishikawa, H. Distribution and evolution of bacteriophage WO in *Wolbachia*, the endosymbiont causing sexual alterations in arthropods. *J Mol Evol* 51, 491-7 (2000).
58. Dunning Hotopp, J. C. et al. Widespread lateral gene transfer from intracellular bacteria to multicellular eukaryotes. *Science* 317, 1753-6 (2007).
59. Funkhouser-Jones, L. J. et al. *Wolbachia* co-infection in a hybrid zone: discovery of horizontal gene transfers from two *Wolbachia* supergroups into an animal genome. *Peer J* 3, e1479 (2015).
60. Kent, B. N. et al. Complete bacteriophage transfer in a bacterial endosymbiont (*Wolbachia*) determined by targeted genome capture. *Genome Biol Evol* 3, 209-18 (2011).
61. Duplouy, A. et al. Draft genome sequence of the male-killing *Wolbachia* strain wBol1 reveals recent horizontal gene transfers from diverse sources. *BMC Genomics* 14, 20 (2013).
62. Klasson, L., Kambris, Z., Cook, P. E., Walker, T. & Sinkins, S. P. Horizontal gene transfer between *Wolbachia* and the mosquito *Aedes aegypti*. *BMC Genomics* 10, 33 (2009).
63. Woolfit, M., Iturbe-Ormaetxe, I., McGraw, E. A. & O'Neill, S. L. An ancient horizontal gene transfer between mosquito and the endosymbiotic bacterium *Wolbachia pipientis*. *Mol Biol Evol* 26, 367-74 (2009).
64. Amen, M. A. & Griffiths, A. Identification and expression analysis of herpes B virus-encoded small RNAs. *J Virol* 85, 7296-311 (2011).
65. Amen, M. A. & Griffiths, A. Packaging of Non-Coding RNAs into Herpesvirus Virions: Comparisons to Coding RNAs. *Front Genet* 2, 81 (2011).
66. Terhune, S. S., Schroer, J. & Shenk, T. RNAs are packaged into human cytomegalovirus virions in proportion to their intracellular concentration. *J Virol* 78, 10390-8 (2004).
67. Bergsbaken, T., Fink, S. L. & Cookson, B. T. Pyroptosis: host cell death and inflammation. *Nat Rev Microbiol* 7, 99-109 (2009).
68. Zhang, L., Villa, N. Y. & McFadden, G. Interplay between poxviruses and the cellular ubiquitin/ubiquitin-like pathways. *FEBS Lett* 583, 607-14 (2009).
69. Sliwa-Dominiak, J., Suszynska, E., Pawlikowska, M. & Deptula, W. Chlamydia bacteriophages. *Arch Microbiol* 195, 765-71 (2013).
70. Hsia, R., Ohayon, H., Gounon, P., Dautry-Varsat, A. & Bavoil, P. M. Phage infection of the obligate intracellular bacterium, *Chlamydia psittaci* strain guinea pig inclusion conjunctivitis. *Microbes Infect* 2, 761-72 (2000).
71. Salim, O., Skilton, R. J., Lambden, P. R., Fane, B. A. & Clarke, I. N. Behind the chlamydial cloak: the replication cycle of chlamydiaphage Chp2, revealed. *Virology* 377, 440-5 (2008).
72. Barr, J. J. et al. Bacteriophage adhering to mucus provide a non-host-derived immunity. *Proc Natl Acad Sci USA* 110, 10771-6 (2013).
73. Moran, N. A., Degnan, P. H., Santos, S. R., Dunbar, H. E. & Ochman, H. The players in a mutualistic symbiosis: insects, bacteria, viruses, and virulence genes. *Proc Natl Acad Sci USA* 102, 16919-26 (2005).
74. Belda, E., Moya, A., Bentley, S. & Silva, F. J. Mobile genetic element proliferation and gene inactivation impact over the genome structure and metabolic capabilities of Sodalis glossinidius, the secondary endosymbiont of tsetse flies. *BMC Genomics* 11, 449 (2010).
75. Rasgon, J. L., Gamston, C. E. & Ren, X. Survival of *Wolbachia pipientis* in cell-free medium. *Appl Environ Microbiol* 72, 6934-7 (2006).
76. Weiss, B. L., Wu, Y., Schwank, J. J., Tolwinski, N. S. & Aksoy, S. An insect symbiosis is influenced by bacterium-specific polymorphisms in outer-membrane protein A. *Proc Natl Acad Sci USA* 105, 15088-93 (2008).
77. Degnan, P. H. & Moran, N. A. Diverse phage-encoded toxins in a protective insect endosymbiont. *Appl Environ Microbiol* 74, 6782-91 (2008).
78. Oliver, K. M., Degnan, P. H., Hunter, M. S. & Moran, N. A. Bacteriophages encode factors required for protection in a symbiotic mutualism. *Science* 325, 992-4 (2009).
79. Chafee, M. E. et al. Decoupling of host-symbiont-phage coadaptations following transfer between insect species. *Genetics* 187, 203-15 (2011).
80. Abascal, F., Zardoya, R. & Posada, D. ProtTest: selection of best-fit models of protein evolution. *Bioinformatics* 21, 2104-5 (2005).
81. Bhere, K. V., Haney, R. A., Ayoub, N. A. & Garb, J. E. Gene structure, regulatory control, and evolution of black widow venom latrotoxins. *FEBS Lett* 588, 3891-7 (2014).

Example 2. Phage WO-Mediated Transformation of *Wolbachia*

This example illustrates the incorporation of new genetic material into the *Wolbachia* chromosome. The most relevant uses include, but are not limited to:

1. To control insect crop pests and disease vectors (Brelsfoard C L, Dobson S L. Asia-Pacific Journal of Molecular Biology and Biotechnology. 2009; 17(3):55-63)
2. To target filarial nematodes in the treatment of both humans (i.e., lymphatic filariasis, onchocerciasis (Slatko B E, et. al. Symbiosis. 2010; 51(1):55-65)) and animals (i.e., heartworm (Frank K, Heald R D. Compend Contin Educ Vet. 2010; 32(4):E4))
3. To utilize transgenics in basic *Wolbachia* research

*Wolbachia* is an obligate intracellular endosymbiont. Because it cannot be cultured or manipulated outside of its eukaryotic host, it is not possible to utilize standard transformation protocols for genetic modification. The primary challenges are:

1. Crossing the eukaryotic membrane
2. Protecting DNA from cellular nucleases and degradation inside the eukaryotic cell
3. Crossing the bacterial membrane
4. Incorporation into the bacterial genome At least two former attempts have been reported with limited success. Transgene integration was detected but neither produced stable transformants.

1. The first attempt involved (i) *Wolbachia* purification from insect cells, (ii) electroporation of *Wolbachia* with various transformation constructs, (iii) reinfection of insect cells and (iv) insertion of transgenes via homologous recombination (Iturbe-Ormaetxe I, Howie J, O'Neill S L, editors. Development of *Wolbachia* transformation by homologous recombination Progress report meeting for the Grand Challenges in Human Health Grant; 2007; Heron Island, Queensland, Australia). Recombination was detected (even in the absence of electroporation) but investigators were unable to select and enrich for recombinant *Wolbachia*. This could be due to low transformation efficiency or complications with tetracycline resistance. Homologous recombination has also been applied in the transformation of *Anaplasma* (Felsheim R F, et. al. Veterinary parasitology. 2010; 167(2-4):167-74), *Rickettsia* (Rachek L I, et. al. Journal of bacteriology. 1998; 180(8):2118-24), and *Coxiella* (Suhan M L, et. al. Journal of bacteriology. 1996; 178(9):2701-8.) but efficiency rates are low and transformants are often not stable.

2. A more recent attempt utilized random insertion of transposons (Thiem S. A Genetic manipulation system for *Wolbachia* in mosquitoes. Michigan State University: USDA; 2014-2019). Investigators were unable to establish a stable transformed line. Similar results were reported in Anaplasma (Oki A T, et. al. Microbes Infect. 2015; 17(11-12):817-22) and are likely due to the random insertion and disruption of critical genes.

DNA sequencing of phage WO particles combined with comparative genomics of *Wolbachia* prophage WO regions allows a phage-mediated approach for transforming *Wolbachia*.

Further characterization of *Wolbachia*'s phage WO led to the classification into three distinct families based on differences in genome content and organization (FIGS. 11-15), recombinase sequences (FIGS. 16 & 17), and sites of integration in the *Wolbachia* genome (FIG. 18).

Family 1 and 2 phages have preferred chromosomal integration sites, i.e., they tend to insert into specific locations in the *Wolbachia* genome. In addition, att sites for both Family 1 and Family 2 phages were identified: WOCauB3 (Family 1) (FIG. 19); WORiC/WOSuziC (Family 1) (FIG. 20); WOVitA1 (Family 2) (FIG. 7).

a. The majority of Family 1 phages integrate in the magnesium chelatase gene. The exception, WOCauB3, integrates between Sua5 and a hypothetical protein. This phage family can be used for site-specific transformation.

b. Family 2 phages integrate in Variable Number Tandem Repeat (VNTR) regions of the *Wolbachia* chromosome. While not as sequence specific, this phage family offers more flexibility with a larger number of potential transformation sites.

Next, using the identified attR and attL sites, the bacterial attB and phage attP sites were extrapolated in WOCauB3 (FIG. 19 and sequences below).

(SEQ ID NO: 7, attL,
TGTATACTTACAGTAAATTTTATTAGCAACTGCTCGTTTTGACTACTAGT

ACAACATTGCATAAT;

SEQ ID NO: 8, attR,
CCTCTTGAACTCTAAATTTGCAATGTTGTCCTTGTTGCTTTTACAACAGA

TTTACTACAATCCGAA;

SEQ ID NO: 9, attP,
CCTCTTGAACTCTAAATTTGCAATGTTGTCCTTGTTGCTTTGACTACTAG

TACAACATTGCATAAT;

-continued
SEQ ID NO: 10, attB,
TGTATACTTACAGTAAATTTTATTAGCAACTGCTCGTTTTTACAACAGAT

TTACTACAATCCGAA).

Using the identified attR and attL sites, the bacterial attB and phage attP sites were extrapolated in WORiC and WOSuziC (FIG. 20 and sequences below).

(SEQ ID NO: 11, attL,
TTATCTGGCAATCCAACAATATTGACTGCTAGTACAACATTGCAT;

SEQ ID NO: 12, attR,
TTGCAATGTTGTCCTTGTTGCTTTAAAAGCTGGAATACCATTTGCC;

SEQ ID NO: 13, attP,
TTGCAATGTTGTCCTTGTTGCTTTGACTGCTAGTACAACATTGCAT;

SEQ ID NO: 14, attB,
TTATCTGGCAATCCAACAATATTAAAAGCTGGAATACCATTTGCC).

In contrast to families 1 and 2, a novel form of integration for Family 3 was identified. These are transposase-associated phages. Only Family 3 prophages are flanked by transposable elements (TEs)—either these TEs represent the preferred integration site for Family 3 or they function to move the prophage around, such as in the transposable phage Mu (FIG. 21). Utilizing the flanking transposase sequences may allow for higher-efficiency recombination assays. Like phage Mu, the flanking tranposases utilize DDE chemistry.

Finally, a computational technique for predicting exact prophage genome was developed (i.e., the phage integrated in *Wolbachia* chromosome) for Family 1 and 2 phages. In general, the active phage recombinase sequence is spliced during chromosomal integration. By performing a BLAST of the individual 5' and 3' segments of the recombinase, one can determine prophage WO genomic boundaries (FIG. 22).

The protocols disclosed herein overcome the challenges described above by incorporating two novel elements:

1. Dendrimers are repetitively branched macromolecules that can be used in both drug delivery and transfection. DNA and dendrimers form a complex that is readily engulfed by cells via nonspecific endocytosis. Highly condensed within the dendrimer complex, the DNA is protected from nuclease degradation. Dendrimer complexes have been utilized to transfer plasmids among *Chlamydia* (Gerard H C, et. al. Nanomedicine. 2013; 9(7):996-1008; Kannan R M, et. al. Microb Pathog. 2013; 65:29-35). They have also been utilized in the transformation of Anaplasma using the Himar1 transposase, although random insertion likely disrupted genes necessary for bacterial fitness (Oki A T, et. al. Microbes Infect. 2015; 17(11-12):817-22). Stable transformation was not achieved.

2. Phage WO is a temperate bacteriophage that infects most arthropod-associated *Wolbachia*. *Phage WO integrates its genome into the Wolbachia chromosome via a large serine recombinase*. This recombinase family (Smith M C, et. al. Biochem Soc Trans. 2010; 38(2): 388-94) does not require host-associated factors and facilitates the unidirectional integration into specific recognition (att) sites (FIG. 10). Disclosed herein are two phage WO recombinases and their specific att sites. In addition, phage WO particles can be utilized as vectors, similar to the plasmid-based shuttle vectors of *Rickettsia* and *Chlamydia* (Burkhardt N Y, et. al. PloS one. 2011; 6(12):e29511; Wang Y, et. al. PLoS pathogens. 2011; 7(9):e1002258) and lambda-based cloning vector (Chauthaiwale V M, et. al. Microbiol Rev. 1992; 56(4):577-91).
3. The phiC31 large serine recombinase is widely used to deliver transgenes to eukaryotic cells. Because many eukaryotic genomes (including humans and *Drosophila* (Bateman J R, et. al. Genetics. 2006; 173(2):769-77; Thyagarajan B, et. al. Mol Cell Biol. 2001; 21(12): 3926-34)) contain a sequence similar to the phiC31 attP, plasmids harboring the attB site have been constructed to incorporate transgenes. This technique bypasses the low efficiency rates of homologous recombination to generate abundant, stable transformants. Within the obligate intracellular bacteria niche, *Wolbachia* are the ideal candidates for phage-mediated transformation because they naturally harbor a temperate phage with a similar large serine recombinase. By combining this novel biology with recent advances in dendrimer nanotechnology, DNA can safely be transferred to intracellular bacteria and readily incorporated into the genome in a site specific, irreversible manner.

Phage WO-Mediated Transformation of *Wolbachia* within Eukaryotic Host Cells
1. Generate desired plasmid construct with phage WO attP site, promoter, transgene(s), and selectable marker(s).
2. Generate expression plasmid with phage WO recombinase gene. (Note: Alternatively, introduce purified recombinase protein)
3. Complex G4 dendrimers with plasmid DNA by vortexing components in sterile water and incubating at room temperature.
4. Resuspend dendrimer complex in Schneider's *Drosophila* media lacking FBS or glutamine.
5. Overlay dendrimer solution onto confluent *Wolbachia*-infected insect cells and incubate.
6. Wash cells and add Schneider's with 10% FBS.
7. After 24 hours, maintain cultures in the presence of antibiotic (i.e., tetracycline).

Phage WO-mediated transformation of host-free *Wolbachia*
1. Purify *Wolbachia* (Gamston C, Rasgon J. J Vis Exp. 2007; (5):223; Iturbe-Ormaetxe I, et. al. J Microbiol Methods. 2011; 84(1):134-6; Rasgon J L, et. al. Appl Environ Microbiol. 2006; 72(11):6934-7) and suspend in Schneider's *Drosophila* media lacking FBS or glutamine.
2. Gently mix with dendrimer complex and incubate at room temperature.
3. Grow host cells (i.e., *Drosophila* S2) to ~80% confluence.
4. Remove media without disturbing cell monolayer.
5. Add 2 ml of suspended *Wolbachia*/dendrimer complex onto cell monolayer.
6. Centrifuge plates at 2,500×g for 1 hour at 15° C.
7. Allow cells to sit overnight.
8. Wash cells and add Schneider's with 10% FBS.
9. After 24 hours, maintain cultures in the presence of antibiotic (i.e., tetracycline).

Phage WO Particles as Genetic Shuttle Vectors
1. Synthesize a phage WO backbone containing only the recombinase and essential phage genes. Insert gene(s) of interest to be incorporated into *Wolbachia* chromosome.
2. Infect *Wolbachia* cells with phage/transgene construct by one of the following methods:
    b. Grow *Wolbachia*-infected host cells to ~80% confluence and add synthetic phage particles.
    c. Purify *Wolbachia* cells, add synthetic phage and re-infect host cells.
    d. Inject insect abdomens (or embryos) with synthetic phage particles.

Transfer of Phage WO Particles to Naïve *Wolbachia* Hosts
1. Purify phage WO particles from donor *Wolbachia* strain
2. Transfer phage particles to recipient *Wolbachia* using one of the following methods:
    a. Grow *Wolbachia*-infected host cells to ~80% confluence and add purified phage particles.
    b. Purify *Wolbachia* cells, add purified phage and re-infect host cells.
    c. Inject insect abdomens (or embryos) with suspended phage particles.

REFERENCES

1. Brelsfoard C L, Dobson S L. *Wolbachia*-based strategies to control insect pests and disease vectors. Asia-Pacific Journal of Molecular Biology and Biotechnology. 2009; 17(3):55-63.
2. Slatko B E, Taylor M J, Foster J M. The *Wolbachia* endosymbiont as an anti-filarial nematode target. Symbiosis. 2010; 51(1):55-65.
3. Frank K, Heald R D. The emerging role of *Wolbachia* species in heartworm disease. Compend Contin Educ Vet. 2010; 32(4):E4.
4. Iturbe-Ormaetxe I, Howie J, O'Neill S L, editors. Development of *Wolbachia* transformation by homologous recombination Progress report meeting for the Grand Challenges in Human Health Grant; 2007; Heron Island, Queensland, Australia
5. Felsheim R F, Chavez A S, Palmer G H, Crosby L, Barbet A F, Kurtti T J, et al. Transformation of *Anaplasma marginale*. Veterinary parasitology. 2010; 167(2-4):167-74.
6. Rachek L I, Tucker A M, Winkler H H, Wood D O. Transformation of *Rickettsia prowazekii* to rifampin resistance. Journal of bacteriology. 1998; 180(8):2118-24.
7. Suhan M L, Chen S Y, Thompson H A. Transformation of *Coxiella burnetii* to ampicillin resistance. Journal of bacteriology. 1996; 178(9):2701-8.
8. Thiem S. A Genetic manipulation system for *Wolbachia* in mosquitoes. Michigan State University: USDA; 2014-2019.
9. Oki A T, Seidman D, Lancina M G, 3rd, Mishra M K, Kannan R M, Yang H, et al. Dendrimer-enabled transformation of *Anaplasma phagocytophilum*. Microbes Infect. 2015; 17(11-12):817-22.
10. Gerard H C, Mishra M K, Mao G, Wang S, Hali M, Whittum-Hudson J A, et al. Dendrimer-enabled DNA delivery and transformation of *Chlamydia pneumoniae*. Nanomedicine. 2013; 9(7):996-1008.
11. Kannan R M, Gerard H C, Mishra M K, Mao G, Wang S, Hali M, et al. Dendrimer-enabled transformation of *Chlamydia trachomatis*. Microb Pathog. 2013; 65:29-35.
12. Smith M C, Brown W R, McEwan A R, Rowley P A. Site-specific recombination by phiC31 integrase and other large serine recombinases. Biochem Soc Trans. 2010; 38(2):388-94.
13. Burkhardt N Y, Baldridge G D, Williamson P C, Billingsley P M, Heu C C, Felsheim R F, et al. Development of shuttle vectors for transformation of diverse *Rickettsia* species. PloS one. 2011; 6(12):e29511.
14. Wang Y, Kahane S, Cutcliffe L T, Skilton R J, Lambden P R, Clarke I N. Development of a transformation system for *Chlamydia trachomatis*: restoration of glycogen biosynthesis by acquisition of a plasmid shuttle vector. PLoS pathogens. 2011; 7(9):e1002258.
15. Chauthaiwale V M, Therwath A, Deshpande V V. Bacteriophage lambda as a cloning vector. Microbiol Rev. 1992; 56(4):577-91.
16. Bateman J R, Lee A M, Wu C T. Site-specific transformation of *Drosophila* via phiC31 integrase-mediated cassette exchange. Genetics. 2006; 173(2):769-77.
17. Thyagarajan B, Olivares E C, Hollis R P, Ginsburg D S, Calos M P. Site-specific genomic integration in mammalian cells mediated by phage phiC31 integrase. Mol Cell Biol. 2001; 21(12):3926-34.
18. Gamston C, Rasgon J. Maintaining *Wolbachia* in cell-free medium. J Vis Exp. 2007; (5):223.
19. Iturbe-Ormaetxe I, Woolfit M, Rances E, Duplouy A, O'Neill S L. A simple protocol to obtain highly pure *Wolbachia* endosymbiont DNA for genome sequencing. J Microbiol Methods. 2011; 84(1):134-6.
20. Rasgon J L, Gamston C E, Ren X. Survival of *Wolbachia pipientis* in cell-free medium. Appl Environ Microbiol. 2006; 72(11):6934-7.

Example 3. Phage WO Applications for Anti-*Wolbachia* Therapies and Treatment of Filarial Nematode Parasites

*Wolbachia* occur in most disease-causing species of filarial nematodes (i.e., human river blindness, human lymphatic filariasis, pet heartworm), where both host reproduction and bacterial viability are dependent upon each other (Frank K, Heald R D. Compend Contin Educ Vet. 2010; 32(4):E4; Slatko B E, et al. Symbiosis. 2010; 51(1):55-65). Thus, elimination of *Wolbachia* can halt the worm's life cycle. Moreover, *Wolbachia* are shed from the nematode's hypodermis and drive the major human immune responses that contribute to disease pathogenesis (Tamarozzi F, et al. Clin Microbiol Rev. 2011; 24(3):459-68). Thus, there is an urgent need for new anti-*Wolbachia* therapeutics that can simultaneously sterilize the worms and reduce the disease pathology. Success in eliminating nematode infections with doxycycline treatments for six weeks in Ghana was a breakthrough (Hoerauf A, et al. Trop Med Int Health. 2000; 5(4):275-9) and significant advances in veterinary care have been made due to the incorporation of doxycycline in heartworm treatment regimens (Kramer L, Genchi C. Veterinary parasitology. 2014; 206(1-2):1-4; McCall J W, et al. Veterinary parasitology. 2008; 158(3):204-14). The primary challenges are:
1. Antibiotic treatment is unrealistic due to the lengthy regime
2. Potential for evolution of widespread antibiotic resistance in the endogenous microbiota
3. Restrictions against use in children and pregnant women
4. A history of doxycycline shortages The Anti-*Wolbachia* Consortium was established in 2007 and funded by the Bill & Melinda Gates Foundation. It has developed an extensive library of drug and compounds with anti-*Wolbachia* activity, most notably minocycline, as well as identified essential *Wolbachia* genes that could be candidates for future drug targets (Johnston K L, et al. Int J Parasitol Drugs Drug Resist. 2014; 4(3):278-86; Sharma R, et al. Sci Rep. 2016; 6:23458; Taylor M J, et al. Parasitology. 2014; 141(1):119-27). To our knowledge, there have been no discoveries of a drug specific to only *Wolbachia*.

The methods disclosed herein overcome the challenges described above by utilizing a *Wolbachia*-specific predator, phage WO. Phage WO is a temperate bacteriophage of arthropod-associated *Wolbachia* and is absent from the mutualistic filarial nematode-associated strains, presumably due to its anti-bacterial cost. It exists as a prophage incorporated in the *Wolbachia* genome, but can enter a lytic phase that leads to the degradation of bacterial DNA, a detached inner membrane and release of phage particles into the eukaryotic extracellular matrix (Bordenstein S R, et al. PLoS pathogens. 2006; 2(5):e43). Phage WO encodes both a lytic cassette and eukaryotic association module (EAM) to lyse bacterial cells and interact with the eukaryotic environment. The application of phage WO in phage therapy protocols circumvents the challenges associated with antibiotics and provides a natural, *Wolbachia*-specific bactericidal agent (Abedon S T, et al. Bacteriophage. 2011; 1(2):66-85; Summers W C. Annu Rev Microbiol. 2001; 55:437-51).

Methods

*Wolbachia* can be targeted by either the direct administration of phage WO particles or the application of phage-encoded antibacterial peptides. Phage WO encodes a robust arsenal of anti-*Wolbachia* peptides, including a well-described toxin-antitoxin system (RelBE, gwv_443 and gwv_444) and a proposed lytic cassette [ankyrin repeat protein (gwv_1107), hypothetical protein (gwv_1106), phospholipase D (gwv_1105) and patatin (gwv_1104)]. Additional anti-*Wolbachia* peptides are encoded in the EAM region of the phage genome and vary among haplotypes.

Phage WO as *Wolbachia*-Specific Phage Therapy

In order to obtain pure phage preps and readily scale-up production, phage particles can be purified from cell lines rather than animal hosts.

1. Generate insect cell line with desired phage WO-containing *Wolbachia*, either through establishment of a novel cell line or transinfection into a recipient cell line (such as *Drosophila* S2 cells). *Wolbachia* strains with well-studied active phage WO particles include wVitA and wCauB.

2. Maintain and grow cells to desired volume.

3. Purify phage WO particles from cell culture by homogenization, treatment with sodium chloride and RNase A, polyethylene glycol (PEG) precipitation, chloroform treatment, ultracentrifugation, and buffer suspension.

4. Administer phage composition to subject suffering from filarial nematode infection. Administration can be considered and monitored by the physician/veterinarian and includes, but is not limited to, topical (eye drops), oral, intravenous, intramuscular, intracardiac, and subcutaneous delivery.

Phage WO Peptides as Anti-*Wolbachia* Agents

1. Clone the anti-*Wolbachia* phage gene or portions of the gene into an expression vector
2. Purify the protein or associated peptide
3. Stabilize the protein/peptide in desired buffer or purify into a crystalline product
4. Delivery systems for the protein/peptide may span enteric coating or encapsulation with pH-sensitive polymers or mucoadhesive polymers, co-administration of protease inhibitors, incorporation of absorption enhancers, modification of the physicochemical properties of the macromolecules, and/or site-specific delivery to the afflicted tissues. Other delivery options include nanoparticles, lipid carriers, such as liposomes, nano-aggregates using amphiphilic polymers, complex coacervation of oppositely charged polyelectrolytes, and inorganic porous particles (Choonara B F, et al.

Biotechnol Adv. 2014; 32(7):1269-82; Park J W, et al. Curr Pharm Des. 2015; 21(22):3097-110; Shaji J, Patole V. Indian J Pharm Sci. 2008; 70(3):269-77).

5. Administer protein/peptide with or without delivery system to subject suffering from filarial nematode infection. Administration can be considered and monitored by the physician/veterinarian and includes, but is not limited to, topical (eye drops), oral, intravenous, intramuscular, intracardiac, site-specific delivery to afflicted tissue, and/or subcutaneous delivery.

REFERENCES

1. Frank K, Heald R D. The emerging role of *Wolbachia* species in heartworm disease. Compend Contin Educ Vet. 2010; 32(4):E4.
2. Slatko B E, Taylor M J, Foster J M. The *Wolbachia* endosymbiont as an anti-filarial nematode target. Symbiosis. 2010; 51(1):55-65.
3. Tamarozzi F, Halliday A, Gentil K, Hoerauf A, Pearlman E, Taylor M J. Onchocerciasis: the role of *Wolbachia* bacterial endosymbionts in parasite biology, disease pathogenesis, and treatment. Clin Microbiol Rev. 2011; 24(3):459-68.
4. Hoerauf A, Volkmann L, Nissen-Paehle K, Schmetz C, Autenrieth I, Buttner D W, et al. Targeting of *Wolbachia* endobacteria in Litomosoides sigmodontis: comparison of tetracyclines with chloramphenicol, macrolides and ciprofloxacin. Trop Med Int Health. 2000; 5(4):275-9.
5. Kramer L, Genchi C. Where are we with *Wolbachia* and doxycycline: an in-depth review of the current state of our knowledge. Veterinary parasitology. 2014; 206(1-2):1-4.
6. McCall J W, Genchi C, Kramer L, Guerrero J, Dzimianski M T, Supakomdej P, et al. Heartworm and *Wolbachia*: therapeutic implications. Veterinary parasitology. 2008; 158(3):204-14.
7. Johnston K L, Ford L, Umareddy I, Townson S, Specht S, Pfarr K, et al. Repurposing of approved drugs from the human pharmacopoeia to target *Wolbachia* endosymbionts of onchocerciasis and lymphatic filariasis. Int J Parasitol Drugs Drug Resist. 2014; 4(3):278-86.
8. Sharma R, Jayoussi G A, Tyrer H E, Gamble J, Hayward L, Guimaraes A F, et al. Minocycline as a re-purposed anti-*Wolbachia* macrofilaricide: superiority compared with doxycycline regimens in a murine infection model of human lymphatic filariasis. Sci Rep. 2016; 6:23458.
9. Taylor M J, Hoerauf A, Townson S, Slatko B E, Ward S A. Anti-*Wolbachia* drug discovery and development: safe macrofilaricides for onchocerciasis and lymphatic filariasis. Parasitology. 2014; 141(1):119-27.
10. Bordenstein S R, Marshall M L, Fry A J, Kim U, Wernegreen J J. The tripartite associations between bacteriophage, *Wolbachia*, and arthropods. PLoS pathogens. 2006; 2(5):e43.
11. Abedon S T, Kuhl S J, Blasdel B G, Kutter E M. Phage treatment of human infections. Bacteriophage. 2011; 1(2): 66-85.
12. Summers W C. Bacteriophage therapy. Annu Rev Microbiol. 2001; 55:437-51. doi: 10.1146/annurev.micro.55.1.437.
13. Choonara B F, Choonara Y E, Kumar P, Bijukumar D, du Toit L C, Pillay V. A review of advanced oral drug delivery technologies facilitating the protection and absorption of protein and peptide molecules. Biotechnol Adv. 2014; 32(7):1269-82.
14. Park J W, Kim S J, Kwag D S, Kim S, Park J, Youn Y S, et al. Multifunctional Delivery Systems for Advanced oral Uptake of Peptide/Protein Drugs. Curr Pharm Des. 2015; 21(22):3097-110.
15. Shaji J, Patole V. Protein and Peptide drug delivery: oral approaches. Indian J Pharm Sci. 2008; 70(3):269-77.

Example 4. Phage WO-Encoded Pesticides and Anti-Filarial Products

In this example, arthropod pests and filarial nematode parasites are targeted using phage WO peptides. The primary challenges facing the treatment of filarial diseases and arthropod pest applications are:
1. Off-target effects of anti-filarial drugs and pesticides
2. A history of ivermectin shortages (anti-filarial)
3. Development of pesticide resistance The concept of phage therapy to target bacterial pathogens is nearly a century old and has achieved great success in the Soviet Union and Eastern Europe. Phage WO is unique in that it not only infects its bacterial host, *Wolbachia*, but is also housed within *Wolbachia*'s arthropod host. Therefore, it must contend with both cellular environments. This is the first phage to encode a defined eukaryotic association module; the recent sequencing of phage WO's complete genome revealed a novel array of eukaryotic association genes involved in innate immunity, programmed cell death, secretion of virulence factors and toxicity (Bordenstein S R, Bordenstein S R. Nature Communications. 2016 Oct. 11; 7:13155).

One major commonality among many crop pests and filarial nematodes is the bacterium *Wolbachia*. *Wolbachia* is an obligate intracellular endosymbiont that infects about 40% of all terrestrial arthropods (Zug R, Hammerstein P. PLoS one. 2012; 7(6):e38544) as well as most filarial nematode species (Taylor M J, et al. Adv Parasitol. 2005; 60:245-84). Most strains of pest-associated *Wolbachia* act as reproductive parasites and harbor phage WO whereas nematode-associated *Wolbachia* act as mutualists and are phage-free. The absence of phage from filarial nematode *Wolbachia* could be due to the anti-eukaryotic genes necessary for phage WO's tripartite (i.e., phage within a bacteria within a eukaryote) lifestyle (Bordenstein S R, et al. PLoS pathogens. 2006; 2(5):e43). Phage WO houses a robust arsenal of eukaryotic-association genes. Located adjacent to the phage tail/patatin region, these genes encode ABC insecticidal toxins, the black widow latrotoxin-CTD, programmed cell death NACHT and NB-ARC, ubiquitination (OTU, PRANC) and sumoylation (Peptidase_C48) associated domains, deaminases, and large ankyrin and tetratricopeptide repeats (TPRs). Many of these genes are specific to the phage WO genome and are eukaryotic in origin. These phage-encoded peptides present a novel source of pesticides/insecticides and anti-filarial drugs.

Methods

Phage WO Peptides as Anti-Filarial Drugs
1. Clone the phage gene or portions of the gene into an expression vector
2. Purify the protein/peptide
3. Stabilize the protein/peptide in desired buffer or purify into a crystalline product.

Delivery systems for the protein/peptide may span enteric coating or encapsulation with pH-sensitive polymers or mucoadhesive polymers, co-administration of protease inhibitors, incorporation of absorption enhancers, modification of the physicochemical properties of the macromolecules, and/or site-specific delivery to the afflicted tissues.

Other delivery options include nanoparticles, lipid carriers, such as liposomes, nano-aggregates using amphiphilic polymers, complex coacervation of oppositely charged polyelectrolytes, and inorganic porous particles (Choonara B F, et al. Biotechnol Adv. 2014; 32(7):1269-82; Park J W, et al. Curr Pharm Des. 2015; 21(22):3097-110; Shaji J, Patole V. Indian J Pharm Sci. 2008; 70(3):269-77).

4. Administer protein/peptide with or without delivery system composition to subject suffering from filarial nematode infection. Administration should be considered and monitored by the physician/veterinarian and includes, but is not limited to, topical (eye drops), oral, intravenous, intramuscular, intracardiac, site-specific delivery to afflicted tissue, and/or subcutaneous delivery.

Phage WO Peptides as Pesticide Agents

1. Clone the phage gene or portions of the gene into an expression vector
2. Purify the protein/peptide
3. Stabilize the protein/peptide in desired buffer or purify into a crystalline product
4. Deliver the protein/peptide with or without delivery system (pesticide) to the biological target. Methods include, but are not limited to, household sprays, seed treatments and crop applications (spray, droplet, aerial)

REFERENCES

1. Bordenstein S R, Bordenstein S R. Eukaryotic association module in phage W O genomes from *Wolbachia*. 2016 Oct. 11; 7:13155
2. Zug R, Hammerstein P. Still a host of hosts for *Wolbachia*: analysis of recent data suggests that 40% of terrestrial arthropod species are infected. PloS one. 2012; 7(6): e38544.
3. Taylor M J, Bandi C, Hoerauf A. *Wolbachia* bacterial endosymbionts of filarial nematodes. Adv Parasitol. 2005; 60:245-84.
4. Bordenstein S R, Marshall M L, Fry A J, Kim U, Wernegreen J J. The tripartite associations between bacteriophage, *Wolbachia*, and arthropods. PLoS pathogens. 2006; 2(5):e43.
5. Choonara B F, Choonara Y E, Kumar P, Bijukumar D, du Toit L C, Pillay V. A review of advanced oral drug delivery technologies facilitating the protection and absorption of protein and peptide molecules. Biotechnol Adv. 2014; 32(7):1269-82.
6. Park J W, Kim S J, Kwag D S, Kim S, Park J, Youn Y S, et al. Multifunctional Delivery Systems for Advanced oral Uptake of Peptide/Protein Drugs. Curr Pharm Des. 2015; 21(22):3097-110.
7. Shaji J, Patole V. Protein and Peptide drug delivery: oral approaches. Indian J Pharm Sci. 2008; 70(3):269-77.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A WO phage transformation system, said system comprising:
   a) a first DNA vector comprising a gene encoding a protein with WO phage integrase activity operably linked to a first promoter active in a host cell, wherein the protein with WO phage integrase activity is a serine recombinase comprising an amino acid sequence at least 60% identical to SEQ ID NO: 2, and
   b) a second DNA vector comprising an attachment site (attP) recognized by the WO phage integrase protein, wherein the attachment site (attP) comprises a sequence at least 60% identical to SEQ ID NO: 5, SEQ ID NO: 9, or SEQ ID NO: 13.

2. The system of claim 1, wherein the second DNA vector further comprises a heterologous gene.

3. The system of claim 2, wherein the second DNA vector further comprises a heterologous gene operably linked to a second promoter active in the host cell.

4. The system of claim 1, wherein the second DNA vector further comprises a selectable marker.

5. The system of claim 4, wherein the selectable marker is a tetracycline resistance marker.

6. The system of claim 3, wherein the first promoter or the second promoter is a *Wolbachia* surface protein (wsp) promoter.

7. The system of claim 1, further comprising complex G4 dendrimers.

8. A WO phage vector, said vector comprising:
   a) a gene encoding a protein with WO phage integrase activity operably linked to a first promoter active in a host cell, wherein the protein with WO phage integrase activity is a serine recombinase comprising an amino acid sequence at least 60% identical to SEQ ID NO: 2, and
   b) an attachment site (attP) recognized by the WO phage integrase protein, wherein the attachment site (attP) comprises a sequence at least 60% identical to SEQ ID NO: 5, SEQ ID NO: 9, or SEQ ID NO: 13, and
   c) a heterologous gene.

9. The vector of claim 8, wherein the heterologous gene is operably linked to a second promoter active in the host cell.

10. The vector of claim 8, wherein the vector further comprises a selectable marker.

11. The vector of claim 10, wherein the selectable marker is a tetracycline resistance marker.

12. The vector of claim 8, wherein the protein with WO phage integrase activity is a serine recombinase comprising the amino acid sequence of SEQ ID NO: 2.

13. The vector of claim 9, wherein the first promoter or the second promoter is a *Wolbachia* surface protein (wsp) promoter.

14. A method for the genetic modification of a DNA of a *Wolbachia* cell comprising in its genome a first attachment site (attB) recognized by a protein with WO phage integrase activity, comprising introducing the WO phage transformation system according to claim 1 into the cell.

15. A method for the genetic modification of a DNA of a *Wolbachia* cell comprising in its genome a first attachment site (attB) recognized by a protein with WO phage integrase activity, comprising introducing the WO phage vector according to claim 8 into the cell.

16. A WO phage transformation system, said system comprising:
   a) a protein with WO phage integrase activity, wherein the protein with WO phage integrase activity is a serine recombinase comprising an amino acid sequence at least 60% identical to SEQ ID NO: 2, and
   b) a DNA vector comprising an attachment site (attP) recognized by the WO phage integrase protein, wherein the attachment site (attP) comprises a sequence at least 60% identical to SEQ ID NO: 5, SEQ ID NO: 9, or SEQ ID NO: 13.

17. The system of claim 16, wherein the DNA vector further comprises a heterologous gene.

18. The system of claim 17, wherein the DNA vector further comprises the heterologous gene operably linked to a promoter active in a host cell.

* * * * *

SEQUENCE LISTING

```
<160> NUMBER OF SEQ ID NOS: 18

<210> SEQ ID NO 1
<211> LENGTH: 1536
<212> TYPE: DNA
<213> ORGANISM: Artificial Sequence
<220> FEATURE:
<223> OTHER INFORMATION: synthetic construct

<400> SEQUENCE: 1
ttgaatgagt atgaatttaa ggatgatggg cttagtgggt ggagtttaga acgtgaaggt      60
ttagatgcat tacgtgataa agtaggagaa gatcaaattg ataaaattta tattcattca     120
cctgaccgac tatcaagaaa atctgcacat caaatgatat tacttgatga atttgaaaaa     180
gcaggagtag aagtaatatt cttaaatcat aagactgaaa ataatccaga gtctaaattg     240
ttattaggaa tgcaaggatt agtggcagaa tatgagtgta caaagattat ggaacgtagt     300 cgtagggggaa aactccatag agcaaaaaaa ggctgtgtaa gtgtaattgg cattgcacct     360
tttggttata atcgtataaa gcatgtagat agagaaaaga caaagtttga aataaatgaa     420
gaggaagcaa aaatagtaaa gcagatgttc atgtgggtag ggcaagagag aataagtata     480
agggaagtgg tacgtagact aagagataag tcaattagaa caagaactgg aaagaaggtg     540
tggtgtccaa taataatttg gaagttatta agaaatccag catataaagg acaagcagcg     600
tttggtaaat taaagagggt tgaaagaaga gaaagaaata aacaaaaggt ttctatctgt     660
cgcacagatg aggacagctg gatttatata ccagtaccaa aaatagttga tgaagggtta     720
tttaataaag tacaaaagca actggatgaa aatagaaaaa gagcaaggat acagagagag     780
ggaggaaaaa agaaatatct attacaaggt ctagttgtgt gtcaaaactg tggatatgcg     840
tatagtggtg cacaatgtgg agttgaggga aagaagttta gctattatcg ctgtagtagt     900
```

```
actatacgta ttactgatgg tagggagaag tgtactaata aattggtccg tacagatatg      960
ttagaaacag ctatatggga aaaggtgaaa aatttactaa aaaacccaga gataataaaa     1020
aatgagtatc accgtagaat tgcagaaaat aaaaatgatg aatcatcaga taagaagttt     1080
gcaagaaggg aaaatcaaat aaaacaaggc atcgaaaagt taatggaaga ctattatagt     1140
caagaaaatg taggagataa aggatatata agtaaggaag aatttaaaca gacgatgaaa     1200
agaatgaggg aacgcttaag agggatagaa gaagagaaga aaaaggtagc tgatcaaaaa     1260
gcaatagaga agggaatgaa ccttatcatc aacagtataa agagtcttta ttccagtgta     1320
aaatctaatt tggaacagct agattggcaa actaagcgtg gcatcattaa agcattagta     1380
gaacgaattc aaattggtta tgaccaggta gaagtggcgt ttagaatcga gaaccagca      1440 cagggtggag agattttaa tttgcaacat tgtactggac gtcataacag tgaagctatt      1500
gtatttgctt tcgccaatct gcagattaaa aggtaa                              1536
```

```
<210> SEQ ID NO 2
<211> LENGTH: 511
<212> TYPE: PRT
<213> ORGANISM: Artificial Sequence
<220> FEATURE:
<223> OTHER INFORMATION: synthetic construct

<400> SEQUENCE: 2

Met Asn Glu Tyr Glu Phe Lys Asp Asp Gly Leu Ser Gly Trp Ser Leu
1               5                   10                  15

Glu Arg Glu Gly Leu Asp Ala Leu Arg Asp Lys Val Gly Glu Asp Gln
            20                  25                  30

Ile Asp Lys Ile Tyr Ile His Ser Pro Asp Arg Leu Ser Arg Lys Ser
        35                  40                  45

Ala His Gln Met Ile Leu Leu Asp Glu Phe Glu Lys Ala Gly Val Glu
    50                  55                  60

Val Ile Phe Leu Asn His Lys Thr Glu Asn Asn Pro Glu Ser Lys Leu
65                  70                  75                  80

Leu Leu Gly Met Gln Gly Leu Val Ala Glu Tyr Glu Cys Thr Lys Ile
                85                  90                  95

Met Glu Arg Ser Arg Arg Gly Lys Leu His Arg Ala Lys Lys Gly Cys
            100                 105                 110

Val Ser Val Ile Gly Ile Ala Pro Phe Gly Tyr Asn Arg Ile Lys His
        115                 120                 125

Val Asp Arg Glu Lys Thr Lys Phe Glu Ile Asn Glu Glu Glu Ala Lys
    130                 135                 140

Ile Val Lys Gln Met Phe Met Trp Val Gly Gln Glu Arg Ile Ser Ile
145                 150                 155                 160

Arg Glu Val Val Arg Arg Leu Arg Asp Lys Ser Ile Arg Thr Arg Thr
                165                 170                 175

Gly Lys Lys Val Trp Cys Pro Ile Ile Trp Lys Leu Leu Arg Asn
            180                 185                 190

Pro Ala Tyr Lys Gly Gln Ala Ala Phe Gly Lys Leu Lys Arg Val Glu
        195                 200                 205

Arg Arg Glu Arg Asn Lys Gln Lys Val Ser Ile Cys Arg Thr Asp Glu
    210                 215                 220

Asp Ser Trp Ile Tyr Ile Pro Val Pro Lys Ile Val Asp Glu Gly Leu
225                 230                 235                 240

Phe Asn Lys Val Gln Lys Gln Leu Asp Glu Asn Arg Lys Arg Ala Arg
```

245                 250                 255
Ile Gln Arg Glu Gly Gly Lys Lys Tyr Leu Leu Gln Gly Leu Val
            260                 265                 270

Val Cys Gln Asn Cys Gly Tyr Ala Tyr Ser Gly Ala Gln Cys Gly Val
        275                 280                 285

Glu Gly Lys Lys Phe Ser Tyr Arg Cys Ser Thr Ile Arg Ile
    290                 295                 300

Thr Asp Gly Arg Glu Lys Cys Thr Asn Lys Leu Val Arg Thr Asp Met
305                 310                 315                 320

Leu Glu Thr Ala Ile Trp Glu Lys Val Lys Asn Leu Leu Lys Asn Pro
                325                 330                 335

Glu Ile Ile Lys Asn Glu Tyr His Arg Arg Ile Ala Glu Asn Lys Asn
                340                 345                 350

Asp Glu Ser Ser Asp Lys Lys Phe Ala Arg Arg Glu Asn Gln Ile Lys
            355                 360                 365

Gln Gly Ile Glu Lys Leu Met Glu Asp Tyr Tyr Ser Gln Glu Asn Val
    370                 375                 380

Gly Asp Lys Gly Tyr Ile Ser Lys Glu Glu Phe Lys Gln Thr Met Lys
385                 390                 395                 400

Arg Met Arg Glu Arg Leu Arg Gly Ile Glu Glu Lys Lys Val
                405                 410                 415

Ala Asp Gln Lys Ala Ile Glu Lys Gly Met Asn Leu Ile Ile Asn Ser
            420                 425                 430

Ile Lys Ser Leu Tyr Ser Ser Val Lys Ser Asn Leu Glu Gln Leu Asp
                435                 440                 445

Trp Gln Thr Lys Arg Gly Ile Ile Lys Ala Leu Val Glu Arg Ile Gln
    450                 455                 460

Ile Gly Tyr Asp Gln Val Glu Val Ala Phe Arg Ile Glu Glu Pro Ala
465                 470                 475                 480

Gln Gly Gly Glu Ile Phe Asn Leu Gln His Cys Thr Gly Arg His Asn
                485                 490                 495

Ser Glu Ala Ile Val Phe Ala Phe Ala Asn Leu Gln Ile Lys Arg
            500                 505                 510

<210> SEQ ID NO 3
<211> LENGTH: 47
<212> TYPE: DNA
<213> ORGANISM: Artificial Sequence
<220> FEATURE:
<223> OTHER INFORMATION: synthetic construct

<400> SEQUENCE: 3
gcaaatacaa tagcttcact gttatgacgt ccagtacaat gttgcaa        47

<210> SEQ ID NO 4
<211> LENGTH: 49
<212> TYPE: DNA
<213> ORGANISM: Artificial Sequence
<220> FEATURE:
<223> OTHER INFORMATION: synthetic construct

<400> SEQUENCE: 4
tttttgtaac attgttatac acatcatgat aaggggctg gcggagttt        49

<210> SEQ ID NO 5
<211> LENGTH: 49
<212> TYPE: DNA
<213> ORGANISM: Artificial Sequence
<220> FEATURE:
<223> OTHER INFORMATION: synthetic construct

<400> SEQUENCE: 5
tttttgtaac attgttatac acatcatgac gtccagtaca atgttgcaa        49

<210> SEQ ID NO 6
<211> LENGTH: 47
<212> TYPE: DNA
<213> ORGANISM: Artificial Sequence
<220> FEATURE:
<223> OTHER INFORMATION: synthetic construct

<400> SEQUENCE: 6
gcaaatacaa tagcttcact gttatgataa gggggctggc ggagttt          47

<210> SEQ ID NO 7
<211> LENGTH: 65
<212> TYPE: DNA
<213> ORGANISM: Artificial Sequence
<220> FEATURE:
<223> OTHER INFORMATION: synthetic construct

<400> SEQUENCE: 7
tgtatactta cagtaaattt tattagcaac tgctcgtttt gactactagt acaacattgc   60
ataat                                                              65

<210> SEQ ID NO 8
<211> LENGTH: 66
<212> TYPE: DNA
<213> ORGANISM: Artificial Sequence
<220> FEATURE:
<223> OTHER INFORMATION: synthetic construct

<400> SEQUENCE: 8
cctcttgaac tctaaatttg caatgttgtc cttgttgctt tgactactag tacaacattg   60
cataat                                                             66

<210> SEQ ID NO 9
<211> LENGTH: 66
<212> TYPE: DNA
<213> ORGANISM: Artificial Sequence
<220> FEATURE:
<223> OTHER INFORMATION: synthetic construct

<400> SEQUENCE: 9
cctcttgaac tctaaatttg caatgttgtc cttgttgctt tgactactag tacaacattg   60
cataat                                                             66

<210> SEQ ID NO 10
<211> LENGTH: 65
<212> TYPE: DNA
<213> ORGANISM: Artificial Sequence
<220> FEATURE:
<223> OTHER INFORMATION: synthetic construct

<400> SEQUENCE: 10
tgtatactta cagtaaattt tattagcaac tgctcgtttt tacaacagat ttactacaat   60
ccgaa                                                              65

<210> SEQ ID NO 11
<211> LENGTH: 45
<212> TYPE: DNA

```
<213> ORGANISM: Artificial Sequence
<220> FEATURE:
<223> OTHER INFORMATION: synthetic construct

<400> SEQUENCE: 11
ttatctggca atccaacaat attgactgct agtacaacat tgcat            45

<210> SEQ ID NO 12
<211> LENGTH: 46
<212> TYPE: DNA
<213> ORGANISM: Artificial Sequence
<220> FEATURE:
<223> OTHER INFORMATION: synthetic construct

<400> SEQUENCE: 12
ttgcaatgtt gtccttgttg ctttaaaagc tggaatacca tttgcc           46

<210> SEQ ID NO 13
<211> LENGTH: 46
<212> TYPE: DNA
<213> ORGANISM: Artificial Sequence
<220> FEATURE:
<223> OTHER INFORMATION: synthetic construct

<400> SEQUENCE: 13
ttgcaatgtt gtccttgttg ctttgactgc tagtacaaca ttgcat           46

<210> SEQ ID NO 14
<211> LENGTH: 45
<212> TYPE: DNA
<213> ORGANISM: Artificial Sequence
<220> FEATURE:
<223> OTHER INFORMATION: synthetic construct

<400> SEQUENCE: 14
ttatctggca atccaacaat attaaaagct ggaataccat ttgcc            45

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
cgaagaacca gcacagggtg g                                      21

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
gctggaagag ggcatctgca tc                                     22

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
tcgtgactgc cctattgctg ct                                     22
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
atgcggccaa agctgggtgt                                              20
```